United States Patent
Smolyar

(10) Patent No.: US 7,148,050 B2
(45) Date of Patent: Dec. 12, 2006

(54) REGULATION OF HUMAN PROTEIN KINASE-LIKE PROTEIN

(75) Inventor: Alex Smolyar, Brookline, MA (US)

(73) Assignee: Bayer Healthcare AG, Leverkusen (DE)

( * ) Notice: Subject to any disclaimer, the term of this patent is extended or adjusted under 35 U.S.C. 154(b) by 177 days.

(21) Appl. No.: 10/471,762

(22) PCT Filed: Mar. 15, 2002

(86) PCT No.: PCT/EP02/02887

§ 371 (c)(1),
(2), (4) Date: Apr. 13, 2004

(87) PCT Pub. No.: WO02/081704

PCT Pub. Date: Oct. 17, 2002

(65) Prior Publication Data

US 2004/0171539 A1  Sep. 2, 2004

Related U.S. Application Data

(60) Provisional application No. 60/337,124, filed on Dec. 10, 2001, provisional application No. 60/326,458, filed on Oct. 3, 2001, provisional application No. 60/324,053, filed on Sep. 24, 2001, provisional application No. 60/276,055, filed on Mar. 16, 2001.

(51) Int. Cl.
*C12N 9/12* (2006.01)
*C12N 15/00* (2006.01)
*C12N 1/20* (2006.01)
*C07H 21/04* (2006.01)
*C07K 1/00* (2006.01)
*C12Q 1/68* (2006.01)

(52) U.S. Cl. ............ 435/194; 530/350; 435/320.1; 435/252.3; 435/6; 536/243.2

(58) Field of Classification Search ......... 435/194, 435/6, 320.1, 325, 252.3; 536/23.2; 530/356
See application file for complete search history.

(56) References Cited

U.S. PATENT DOCUMENTS 5,635,177 A  6/1997 Goeddel et al.

2004/0053394 A1 * 3/2004 Gururajan et al. ....... 435/252.3

FOREIGN PATENT DOCUMENTS

| WO | WO 01 29564 | 4/2001 |
| WO | WO 01 66594 | 9/2001 |
| WO | WO 02 33099 | 4/2002 |

OTHER PUBLICATIONS

Hanks et al.: "Protein kinases 6. The eukaryotic protein kinse superfamily: kinase (catalytic) domain structure and classification"; FASEB Journal; May 1995; 9 (8); 576-96.
Hanks et al.: "Protein Kinase Catalytic Domain Sequence Database: Identification of Conserved Features of Primary Structure and Classification of Family Members"; Methods in Enzymology; vol. 200; 1991; pp. 38-62.
Database EMBL Online!; Sep. 29, 2000; Sugano et al.: "Homo sapiens cDNA: FLJ23119 fis clone LNG07978"; Database accession No. Ak026772; XP002222894.
Nagase et al.: "Prediction of the coding sequences of unidentified human genes XX. The complete sequences of 100 new cDNA clones from brain which code for large proteins in vitro"; DNA Research; 8 (2); Apr. 27,2001; 85-95; XP002943489.
Dorow et al.: "Indentification of a new family of human epithelial protein kinases containing two leucine/isoleucine-zipper domains"; European Journal of Biochemistry; 213 (2); 1993; 701-710; XP001084152.
Hanes et al.: "Characterization by cDNA cloning of two new human protein kinases. Evidence by sequence comparison of a new family of mammalian protein kinases"; Journal of Molecular Biology; vol. 224;1994; 665-672; XP002064038.
Taylor et al.: "How do protein kinases discriminate between serine/threonine and tyrosine? Structural insights from the insulin receptor protein-tyrosine kinase"; FASEB Journal; 9(131); 1995; 1255-1266; XP001109316.
Strausberg et al.: "Generation and initial analysis of more than 15,000 full-length human and mouse cDNA sequences"; PROC NATL ACAD SCI USA; 2002; 99 (26); 16899-903 [PubMed/12477932].

* cited by examiner

*Primary Examiner*—Maryam Monshipouri
(74) *Attorney, Agent, or Firm*—Banner & Witcoff, Ltd.

(57) ABSTRACT

Reagents that regulate human protein kinase-like protein and reagents which bind to human protein kinase-like gene products can play a role in preventing, ameliorating, or correcting dysfunctions or diseases including, but not limited to, cancer, CNS disorders, COPD, obesity, diabetes, and cardiovascular disorders.

18 Claims, 14 Drawing Sheets

Fig. 1

```
atgaccgact tcccggccag gctcttcctg gagaacagca
agctggagca cagcgaggac gagggcagcg tcctgggcca
gggcggcagt ggcaccgtca tctaccgggc ccggtaccag
ggccagcctg tggccgtcaa gcgcttccac atcaaaaaat
tcaagaactt tgctaacgta ccggcagaca ccatgctgag
gcacctgcgg gccaccgatg ccatgaagaa cttctccgag
ttccggcagg aggccagcat gctgcacgcg ctgcagcacc
cctgcatcgt ggcgctcatc ggcatcagca tccacccgct
ctgcttcgcc ctggagctcg cgccgctcag cagcctcaac
accgtgctgt ccgagaacgc cagagattct tcctttatac
ccctgggaca catgctcacc caaaaaatag cctaccagat
cgcctcgggc ctggcctacc tgcacaagaa aaacatcatc
ttctgtgacc tgaagtcgga caacattctg gtgtggtccc
ttgacgtcaa ggagcacatc aacatcaagc tatctgacta
cgggatttcg aggcagtcat tccatgaggg cgccctaggc
gtggagggca ctcctggcta ccaggcccca gagatcaggc
ctcgcattgt atatgatgag aaggtagata tgttctccta
tggaatggtg ctctacgagt tgctgtcagg acagcgccct
gcactgggcc accaccagct ccagattgcc aagaagctgt
ccaagggcat ccgcccggtt ctggggcagc cggaggaagt
gcagttccgg cgactgcagg cgctcatgat ggagtgctgg
gacactaagc cagagaag
```

Fig. 2

```
MTDFPARLFL ENSKLEHSED EGSVLGQGGS GTVIYRARYQ
GQPVAVKRFH IKKFKNFANV PADTMLRHLR ATDAMKNFSE
FRQEASMLHA LQHPCIVALI GISIHPLCFA LELAPLSSLN
TVLSENARDS SFIPLGHMLT QKIAYQIASG LAYLHKKNII
FCDLKSDNIL VWSLDVKEHI NIKLSDYGIS RQSFHEGALG
VEGTPGYQAP EIRPRIVYDE KVDMFSYGMV LYELLSGQRP
ALGHHQLQIA KKLSKGIRPV LGQPEEVQFR RLQALMMECW DTKPEK
```

Fig. 3

```
AELTLEEIIGIGGFGKVYRAFWIGDEVAVKAARHDPDEDISQTIENVRQEAKL
FAMLKHPNIIALRGVCLKEPNLCLVMEFARGGPLNRVLSGKRIPPDILVNWAV
QIARGMNYLHDEAIVPIIHRDLKSSNILILQKVENGDLSNKILKITDFGLARE
WHRTTKMSAAGTYAWMAPEVIRASMFSKGSDVWSYGVLLWELLTGEVPFRGID
GLRVAYGVAMNKLALPIPSTCPEPFAKLMEDCWNPDPHSRPSFTNILDQLTTI
EESGFFEMPKDSFHCLQDNWKHEIQEMFDQLRAKEKELRTWEEELTRAALQQK
NQEELLRRREQELAEREIDILERELNIIIHQLCQEKPRVKKRKGKFRKSRLAQ
PVLPFPHGHSRCPGGTGSSWGGQ
```

Fig. 4

CACGAGGCTGGTCCCTGAACTGTTCATGACCGACTTCCCGGCCAGGCTCTTCC
TGGAGAACAGCAAGCTGGAGCACAGCGAGGACGAGGGCAGCGTCCTGGGCCAG
GGCGGCAGTGGCACCGTCATCTACCGGGCCCGGTACCAGGGCCAGCCTGTGGC
CGTCAAGCGCTTCCACATCAAAAAATTCAAGAACTTTGCTAACGTACCGGCAG
ACACCATGCTGAGGCACCTGCGGGCCACCGATGCCATGAAGAACTTCTCCGAG
TTCCGGCAGGAGGCCAGCATGCTGCACGCGCTGCAGCACCCCTGCATCGTGGC
GCTCATCGGCATCAGCATCCACCCGCTCTGCTTCGCCCTGGAGCTCGCGCCGC
TCAGCAGCCTCAACACCGTGCTGTCCGAGAACGCCAGAGATTCTTCCTTTATA
CCCCTGGGACACATGCTCACCCAAAAAATAGCCTACCAGATCGCCTCGG

Fig. 5

CACGAGGCTGGTCCCTGAACTGTTCATGACCGACTTCCCGGCCAGGCTCTTCC
TGGAGAACAGCAAGCTGGAGCACAGCGAGGACGAGGGCAGCGTCCTGGGCCAG
GGCGGCAGTGGCACCGTCATCTACCGGGCCCGGTACCAGGGCCAGCCTGTGGC
CGTCAAGCGCTTCCACATCAAAAAATTCAAGAACTTTGCTAACGTACCGGCAG
ACACCATGCTGAGGCACCTGCGGGCCACCGATGCCATGAAGAACTTCTCCGAG
TTCCGGCAGGAGGCCAGCATGCTGCACGCGCTGCAGCACCCCTGCATCGTGGC
GCTCATCGGCATCAGCATCCACCCGCTCTGCTTCGCCCTGGAGCTCGCGCCGC
TCAGCAGCCTCAACACCGTGCTGTCCGAGAACGCCAGAGATTCTTCCTTTATA
CCCCTGGGACACATGCTCACCCAAAAAATA

Fig. 6

CTCTTCCTGTGAGAACAGCAAGCTGGAGCACAGCGAGGACGAGGGCAGCGTCC
TGGGCCACGGCGGCAGTGGCACCGTCATCTACCGGGCCCGGTACCAGGGCCAG
CCTGTGGCCGTCAAGCGCTTCCACATCAAAAAATTCAAGAACTTTGCTAACGT
ACCGGCAGACACCATGCTGAGGCACCTGCGGGCCACCGATGCCATGAAGAACT
TCTCCGAGTTCCGGCAGGAGGCCAGCATGCTGCACGCGCTGCAGCACCCCTGC
ATCGTGGCGCTCATCGGCATCAGCATCCACCCGACTCTGCTTCGCCCTGGAGC
TCGCGCCGCTCAGCAGCCTCAACACCGTGCTGTCCGAGAACGCCAGAGATTCT
TCCTTTATACCCCTGGGACACATGCTCACCCAAAAAATAGCCTACCAGATCGC
CTCGGGCCTGGCCTACCTGCACAAGAAAAACATCATCTTCTGTGACCTGAAGT
CGGACAACATTCTGGTGTGGTCCCTTGACGTCAAGGAGCACATCAACATCAAG
CTATCTGACTACGGGATTTCGAGGCAGTCATTCCATGAGGGCGCCCTAGGCGT
GGAGGGCACTCCTGGCTACCAGGCCCCAGAGATCAGGCCTCGCATTGTATATG
ATGAGAAGGTAGCATATGTCTCCTATGGAATGGTGCTCTACGAGTTGCTGTCA
GGACAGGGGCCTGCATTGGGCCACCAACAGCTTCCGATTGCCAAGAGGTGTCC
AAGGCATCCGCCCGGTACTGAGGACAGCCGGAAGGAACTGCAATCCGGCGATG
CATGGCTCATTATTGAGATGCTGGGAAACTATAATCAAGCGAACGGAGCACTG
TGGCCCTATACGTAGGTAGCCCCAATTAGACGACCCTCACATTATGAACCAAT
CGGTAATAAACGTGTACGTGCGGGACTAGCAGCCACCTATAACACACAGCCAC
GGCCACCTGGGCTGTGATGCATACAAGACGCTCAAACACGCGGGTCACAGAAA
GCCTCATCGAGTCGCATCCACCCGAGAGAGTAGCGCCGCCGAACTAGTATAGA
CGGTAT

Fig. 7

CACGAGGAAAAAATTCAAGAACTTTGCTAACGTACCGGCAGACACCATGCTGA
GGCACCTGCGGGCCACCGATGCCATGAAGAACTTCTCCGAGTTCCGGCAGGAG
GCCAGCATGCTGCACGCGCTGCAGCACCCCTGCATCGTGGCGCTCATCGGCAT
CAGCATCCACCCGCTCTGCTTCGCCCTGGAGCTCGCGCCGCTCAGCAGCCTCA
ACACCGTGCTGTCCGAGAACGCCAGAGATTCTTCCTTTATACCCCTGGGACAC
ATGCTCACCCAAAAAATAGCCTACCAGATCGCCTCGGGCCTGGCCTACCTGCA
CAAGAAAAACATCATCTTCTGTGACCTGAAGTCGGACAACATTCTGGTGTGGT
CCCTTGACGTCAAGGAGCACATCAACATCAAGCTATCTGACTACGGGATTTCG
AGGCAGTCATTCCATGAGGGCGCCCTANGCGTGGAGGGCACTCCTGG

Fig. 8

CCCCTTAATGATTTTGCACAGGCCCCAAAGCAATGCTGTCTTACCTGCGTGCT
CAGCTGCGGAAAGCGGAAAAGTGCAAGCTGATGAAGATGATCATCGTGGGTCc
ccgcgccagggcaagtccaccctcctggagatcttacagacggggagggccc
cccaggtggtgcatggagaggccaccatcaggaccaccaagtgggagctccag
aggccggctggctcaagagccaaggttgagtccgtggagttcaacgtctggga
catcggggaccggccagcatggccactgtcaaccagtgcttcttcacggaca
aggccctgtacgtggtggtctggaacctggcgctgggggaggaggccgtggcc
aacctccagttctggctgctcaacatcgaggccaaggcccaaacgccgtggt
gctggtggtcgggacgcacctggatttaattgaagccaagttccgtgtggaaa
ggattgcaacgctgcgtgcctatgtgctggcactctgccgctcccctccggc
tccagggccacaggcttcccagacatcaccttcaaacacttacatgagatttc
ctgcaagagcctggaaggtcaggaagggctgcgacagctgattttccacgtca
cgtgcagcatgaaggacgtgggcagcaccatcggctgccagcgactggcaggg
cggctgatccccaggagctacctgagcctgcaggaggccgtgctggcagagca
gcagcgccgcagccgggacgacgacgtgcagtacctgacggacaggcagctgg
agcagctggtggagcagacgcccgacaacgacatcaaggactacgaggacctg
cagtcagccatcagcttcctcatagaaaccggcaccctgctccatttcccgga
caccagccacggcctgaggaacctctacttcctcgaccctatttggctctcg
aatgtctgcagaggatctttaatattaagggctctcggtcagtggccaagaat
ggggtgatcagagcagaagacctcaggatgctgctggtggggactggcttcac
gcagcagacggaagagcagtacttccagttcctggccaagtttgagatcgccc
tgcccgtcgccaatgacagctacctcctgccccatctccttccatctaaacct
ggcctggacaccacggtatgcggcacccacagccaacaccattcagagggt
atttaagatgagcttcgttcccgttggcttctggcaaaggtttatagcacgga
tgctgatcagcctggcggagatggacctgcagcttttgaaaacaagaagaat
actaaaagcaggaacaggaaagtcaccatttacagttttacaggaaaccagag
aaatcgctgtagcacattcagagtgaaaagaaatcagaccatctattggcagg
aagggctcctggtcacttttgatgggggctacctcagtgtggaatcttccgac
gtgaactggaaaaagaagaaaagcggaggaatgaaaattgtttgccaatcaga
agtgagggacttctcagccatggctttcatcacggaccacgtcaattccttga
ttgatcagtggtttcccgccctgacggccacagagagcgacgggacgccactc
atggagcagtacgtgccctgcccggtctgcgagacagcctgggcccagcacac
ggaccccagtgagaaatcagaggatgtgcagtacttcgacatggaagactgtg
tcctgacggccatcgagcgggacttcatctcctgcccagacacccggacctc
cccgtgccgctgcaggagctggtccctgaactgttcatgaccgacttcccggc
caggctcttcctggagaacagcaagctggagcacagcgaggacgagggcagcg
tcctgggccagggcggcagtggcaccgtcatctaccgggcccggtaccagggc
cagcctgtggccgtcaagcgcttccacatcaaaaaattcaagaactttgctaa
cgtaccggcagacaccatgctgaggcacctgcgggccaccgatgccatgaaga
acttctccgagttccggcaggaggccagcatgctgcacgcgctgcagcacccc
tgcatcgtggcgctcatcggcatcagcatccaccgctctgcttcgccctgga
gctcgcgccgctcagcagcctcaacaccgtgctgtccgagaacgccagagatt
cttcctttatacccctgggacacatgctcacccaaaaaatagcctaccagatc
gcctcgggcctggcctacctgcacaagaaaaacatcatcttctgtgacctgaa
gtcggacaacattctggtgtggtcccttgacgtcaaggagcacatcaacatca
agctatctgactacgggattcgaggcagtcattccatgagggcgccctaggc
gtggagggcactcctggctaccaggcccagagatcaggcctcgcattgtata
tgatgagaaggtagatatgttctcctatggaatggtgctctacgagttgctgt
caggacagcgccctgcactgggccaccaccagctccagattgccaagaagctg
tccaagggcatccgcccggtctggggcagccggaggaagtgcagttccggcg
actgcaggcgctcatgatggagtgctgggacactaagccagagaagcgaccgc
tggccctgtcggtggtgagccagatgaaggacccgacttttgccaccttcatg
tatgaactgtgctgtgggaagcagacagccttcttctcatcccagggccagga

Fig. 8 (continued)

```
gtacaccgtggtgttttgggatggaaaagaggagtccaggaactacacggtgg
tgaacacagagaagggcctcatggaggtgcagaggatgtgctgccctgggatg
aaggtgagctgccagctccaggtccagagatccctgtggacagccaccgagga
ccagaaaatctacatctacaccctcaagggcatgtgcccttaaacacacccc
aacaggccttggatactccagctgtcgtcacctgcttcttggccgtgcctgtt
attaaaaagaattcctacctggtcttagcgggcctcgccgatgggcttgtggc
tgtgtttcccgtggtgcggggcaccccaaaggacagctgctcctacctgtgct
cacacacagccaacaggtccaagttcagcatcgcggatgaagacgcacggcag
aaccCctacccagtgaaggccatggaggtggtcaacagcggctctgaggtctg
gtacagcaatgggccgggcctccttgtcatcgactgtgcctccctggagatct
gcaggcggctggagccctacatggcccctccatggttacgtcagtcgtgtgc
agctctgagggcagaggggaggaggtcgtctggtgcctggatgacaaggccaa
ctccttggtgatgtaccactccaccacctaccagctgtgtgcccggtacttct
gcggggtccccagcccctcagggacatgtttccgtgcggcccttggacacg
gaaccccggcagccagccacacggccaacccaaaggtgcctgaggggactc
catcgcggacgtgagcatcatgtacagtgaggagctgggcacgcagatcctga
tccaccaggaatcactcactgactactgctccatgtcctcctactcctcatcc
ccaccccgccaggctgccaggtcccctcaagcctcccagctcccagcaag
ttcttccagtgtgcctttctccaccgactgcgaggactcagacatgctacata
cgcccggtgctgcctccgacaggtctgagcatgacctgaccccatggacggg
gagaccttcagccagcacctgcaggccgtgaagatcctcgccgtcagagacct
catttgggtccccaggcgcggtggagatgttatcgtcattggcctggagaagg
attctgaagcccagcggggccgagtcattgccgtcttaaaagcccgagagctg
actccgcatggggtgctggtggatgctgccgtggtggcaaaggacactgttgt
gtgcacctttgaaaatgaaaacacagagtggtgcctggccgtctggaggggct
ggggcgccagggagttcgacatttctaccagtcctacgaggagctgggccgg
ctggaggcttgcactcgcaagagaaggtaattcctgtggaatgactgtcacac
atcagagctggctggcccggggctgcagcctgaccCctctgccatcggcctct
agttctccaaggacctagaagacagatggagttctcccctgaactccttgctg
ctaagaagtgctgagaagttactcgcctggcggtggctccagggttctctggt
tctctggagcagagttctctgaatacccCatccccaactgctgattttacag
ccccagggaagacagtggtatcaggctgggagcggcctcctctggcctccccc
atcagtttgcaggagcaggggtgcaggatcctgttctgagctgggtcaaacaa
agcagggccgggccttcctgccatcccaggtctcagatggaattacactaga
ggccctccgctgggaagcacttgaggtagggcaggagggggctgtgacccct
gcccttccccgccagagacctcgggctctcagcacattccacaggctcctga
gtccccgaggcctggccagcttgggcaagcaagatcagatgtctctgtgtt
cgggaaggtctccgtgtgggaaagcccttggggatcccgggtgaggagtgtt
gccccatccagagaatgaatgagttcctttaagtgccaccgccagcaagccca
gaggcacacagtccgagtgcaccgcttagcctttacattcctctccaccgac
aaaaggaaggggaaactcaatcagcaggacttcagaaagggccttgtgtttat
agctttgtcaagtaaatttggacgcagctggagcacaggccctgtttgtttgc
acataataatcttgtttatcactttaaaaaattcagtaatatctcagcagtca
ggcttctggttgtgaaatcacattgtatgggatttataccaaattatgtattt
gctaaacattcactgcacacgtgtacagcggagtacgaaaggaacgttgtcc
acagggatttatggatacaacagcaaacattttataaactatgcacatgcat
tacacacatgcacacacatatgcacacacatgtgcaaacatagccactttttt
gtcaagagttaccctttggggctccttaaaccagaatggagtttgaaagaga
gatcatactccagctgaagtttgttgacccttttctaaaattaaaaagatcaa
atttagtatttgctggatatgcagggagatgagactcttttaatctcaaaata
aacagattctttcaag
```

Fig. 9

MLSYLRAQLRKAEKCKLMKMIIVGPPRQGKSTLLEILQTGRAPQVVHGEATIR
TTKWELQRPAGSRAKVESVEFNVWDIGGPASMATVNQCFFTDKALYVVVWNLA
LGEEAVANLQFWLLNIEAKAPNAVVLVVGTHLDLIEAKFRVERIATLRAYVLA
LCRSPSGSRATGFPDITFKHLHEISCKSLEGQEGLRQLIFHVTCSMKDVGSTI
GCQRLAGRLIPRSYLSLQEAVLAEQQRRSRDDDVQYLTDRQLEQLVEQTPDND
IKDYEDLQSAISFLIETGTLLHFPDTSHGLRNLYFLDPIWLSECLQRIFNIKG
SRSVAKNGVIRAEDLRMLLVGTGFTQQTEEQYFQFLAKFEIALPVANDSYLLP
HLLPSKPGLDTHGMRHPTANTIQRVFKMSFVPVGFWQRFIARMLISLAEMDLQ
LFENKKNTKSRNRKVTIYSFTGNQRNRCSTFRVKRNQTIYWQEGLLVTFDGGY
LSVESSDVNWKKKKSGGMKIVCQSEVRDFSAMAFITDHVNSLIDQWFPALTAT
ESDGTPLMEQYVPCPVCETAWAQHTDPSEKSEDVQYFDMEDCVLTAIERDFIS
CPRHPDLPVPLQELVPELFMTDFPARLFLENSKLEHSEDEGSVLGQGGSGTVI
YRARYQGQPVAVKRFHIKKFKNFANVPADTMLRHLRATDAMKNFSEFRQEASM
LHALQHPCIVALIGISIHPLCFALELAPLSSLNTVLSENARDSSFIPLGHMLT
QKIAYQIASGLAYLHKKNIIFCDLKSDNILVWSLDVKEHINIKLSDYGISRQS
FHEGALGVEGTPGYQAPEIRPRIVYDEKVDMFSYGMVLYELLSGQRPALGHHQ
LQIAKKLSKGIRPVLGQPEEVQFRRLQALMMECWDTKPEKRPLALSVVSQMKD
PTFATFMYELCCGKQTAFFSSQGQEYTVVFWDGKEESRNYTVVNTEKGLMEVQ
RMCCPGMKVSCQLQVQRSLWTATEDQKIYIYTLKGMCPLNTPQQALDTPAVVT
CFLAVPVIKKNSYLVLAGLADGLVAVFPVVRGTPKDSCSYLCSHTANRSKFSI
ADEDARQNPYPVKAMEVVNSGSEVWYSNGPGLLVIDCASLEICRRLEPYMAPS
MVTSVVCSSEGRGEEVVWCLDDKANSLVMYHSTTYQLCARYFCGVPSPLRDMF
PVRPLDTEPPAASHTANPKVPEGDSIADVSIMYSEELGTQILIHQESLTDYCS
MSSYSSSPPRQAARSPSSLPSSPASSSSVPFSTDCEDSDMLHTPGAASDRSEH
DLTPMDGETFSQHLQAVKILAVRDLIWVPRRGGDVIVIGLEKDSEAQRGRVIA
VLKARELTPHGVLVDAAVVAKDTVVCTFENENTEWCLAVWRGWGAREFDIFYQ
SYEELGRLEACTRKRR

Fig. 10

```
CAAAGCAATGCTGTCTTACCTGCGTGCTCAGCTGCGGAAAGCGGAAAAGTGCA
AGCTGATGAAGATGATCATCGTGGGTCCCCCGCGCCAGGGCAAGTCCACCCTC
CTGGAGATCTTACAGACGGGGAGGGCCCCCAGGTGGTGCATGGAGAGGCCAC
CATCAGGACCACCAAGTGGGAGCTCCAGAGGCCGGCTGGCTCAAGAGCCAAGG
TTGAGTCCGTGGAGTTCAACGTCTGGGACATCGGGGGACCGGCCAGCATGGCC
ACTGTCAACCAGTGCTTCTTCACGGACAAGGCCCTGTACGTGGTGGTCTGGAA
CCTGGCGCTGGGGGAGGAGGCCGTGGCCAACCTCCAGTTCTGGCTGCTAACA
TCGAGGCCAAGGCCCCAAACGCCGTGGTGCTGGTGGTCGGGACGCACCTGGAT
TTAATTGAAGCCAAGTTCCGTGTGGAAGGATTGCAACGCTGCGTGCCTATGT
GCTGGCACTCTGCCGCTCCCCCTCCGGCTCCAGGGCCACAGGCTTCCCAGACA
TCACCTTCAAACACTTACATGAGATTTCCTGCAAGAGCCTGGAAGGTCAGGAA
GGGCTGCGACAGCTGATTTTCCACGTCACGTGCAGCATGAAGGACGTGGGCAG
CACCATCGGCTGCCAGCGACTGGCAGGGCGGCTGATCCCCAGGAGCTACCTGA
GCCTGCAGGAGGCCGTGCTGGCAGAGCAGCAGCGCCGCAGCCGGGACGACGAC
GTGCAGTACCTGACGGACAGGCAGCTGGAGCAGCTGGTGGAGCAGACGCCCGA
CAACGACATCAAGGACTACGAGGACCTGCAGTCAGCCATCAGCTTCCTCATAG
AAACCGGCACCCTGCTCCATTTCCCGGACACCAGCCACGGCCTGAGGAACCTC
TACTTCCTCGACCCTATTTGGCTCTCCGAATGTCTGCAGAGGATCTTTAATAT
TAAGGGCTCTCGGTCAGTGGCCAAGAATGGGGTGATCAGAGCAGAAGACCTCA
GGATGCTGCTGGTGGGGACTGGCTTCACGCAGCAGACGGAAGAGCAGTACTTC
CAGTTCCTGGCCAAGTTTGAGATCGCCCTGCCCGTCGCCAATGACAGCTACCT
CCTGCCCCATCTCCTTCCATCTAAACCTGGCCTGGACACCCACGGTATGCGGC
ACCCCACAGCCAACACCATTCAGAGGGTATTTAAGATGAGCTTCGTTCCCGTT
GGCTTCTGGCAAAGGTTTATAGCACGGATGCTGATCAGCCTGGCGGAGATGGA
CCTGCAGCTTTTTGAAAACAAGAAGAATACTAAAAGCAGGAACAGGAAAGTCA
CCATTTACAGTTTTACAGGAAACCAGAGAAATCGCTGTAGCACATTCAGAGTG
AAAAGAAATCAGACCATCTATTGGCAGGAAGGGCTCCTGGTCACTTTTGATGG
GGGCTACCTCAGTGTGGAATCTTCCGACGTGAACTGGAAAAAGAAGAAAAGCG
GAGGAATGAAAATTGTTTGCCAATCAGAAGTGAGGGACTTCTCAGCCATGGCT
TTCATCACGGACCACGTCAATTCCTTGATTGATCAGTGGTTTCCCGCCCTGAC
AGCCACAGAGAGCGACGGGACGCCACTCATGGAGCAGTACGTGCCCTGCCCGG
TCTGCGAGACAGCCTGGGCCCAGCACACGGACCCCAGTGAGAAATCAGAGGAT
GTGCAGTACTTCGACATGGAAGACTGTGTCCTGACGGCCATCGAGCGGGACTT
CATCTCCTGCCCCAGACACACCCGGACCTCCCCGTGCCGCTGCAGGAGCTGGTCC
CTGAACTGTTCATGACCGACTTCCCGGCCAGGCTCTTCCTGGAGAACAGCAAG
CTGGAGCACAGCGAGGACGAGGGCAGCGTCCTGGGCCAGGGCGGCAGTGGCAC
CGTCATCTACCGGGCCCGGTACCAGGGCCAGCCTGTGGCCGTCAAGCGCTTCC
ACATCAAAAAATTCAAGAACTTTGCTAACGTACCGGCAGACACCATGCTGAGG
CACCTGCGGGCCACCGATGCCATGAAGAACTTCTCCGAGTTCCGGCAGGAGGC
CAGCATGCTGCACGCGCTGCAGCACCCCTGCATCGTGGCGCTCATCGGCATCA
GCATCCACCCGCTCTGCTTCGCCCTGGAGCTCGCGCCGCTCAGCAGCCTCAAC
ACCGTGCTGTCCGAGAACGCCAGAGATTCTTCCTTTATACCCCTGGGACACAT
GCTCACCCAAAAAATAGCCTACCAGATCGCCTCGGGCCTGGCCTACCTGCACA
AGAAAAACATCATCTTCTGTGACCTGAAGTCGGACAACATTCTGGTGTGGTCC
CTTGACGTCAAGGAGCACATCAACATCAAGCTATCTGACTACGGGATTTCGAG
GCAGTCATTCCATGAGGGCGCCCTAGGCGTGGAGGGCACTCCTGGCTACCAGG
CCCCAGAGATCAGGCCTCGCATTGTATATGATGAGAAGGTAGATATGTTCTCC
TATGGAATGGTGCTCTACGAGTTGCTGTCAGGACAGCGCCCTGCACTGGGCCA
CCACCAGCTCCAGATTGCCAAGAAGCTGTCCAAGGGCATCCGCCCGGTTCTGG
GGCAGCCGGAGGAAGTGCAGTTCCGGCGACTGCAGGCGCTCATGATGGAGTGC
TGGGACACTAAGCCAGAGAAGCGACCGCTGGCCCTGTCGGTGGTGAGCCAGAT
GAAGGACCCGACTTTTGCCACCTTCATGTATGAACTGTGCTGTGGGAAGCAGA
CAGCCTTCTTCTCATCCCAGGGCCAGGAGTACACCGTGGTGTTTTGGGATGGA
```

Fig. 10 (continued)

```
AAAGAGGAGTCCAGGAACTACACGGTGGTGAACACAGAGAAGGGCCTCATGGA
GGTGCAGAGGATGTGCTGCCCTGGGATGAAGGTGAGCTGCCAGCTCCAGGTCC
AGAGATCCCTGTGGACAGCCACCGAGGACCAGAAAATCTACATCTACACCCTC
AAGGGCATGTGCCCCTTAAACACACCCCAACAGGCCTTGGATACTCCAGCTGT
CGTCACCTGCTTCTTGGCCGTGCCTGTTATTAAAAAGAATTCCTACCTGGTCT
TAGCGGGCCTCGCCGATGGGCTTGTGGCTGTGTTTCCCGTGGTGCGGGGCACC
CCAAAGGACAGCTGCTCCTACCTGTGCTCACACACAGCCAACAGGTCCAAGTT
CAGCATCGCGGATGAAGACGCACGGCAGAACCCCTACCCAGTGAAGGCCATGG
AGGTGGTCAACAGCGGCTCTGAGGTCTGGTACAGCAATGGGCCGGGCCTCCTT
GTCATCGACTGTGCCTCCCTGGAGATCTGCAGGCGGCTGGAGCCCTACATGGC
CCCCTCCATGGTTACGTCAGTCGTGTGCAGCTCTGAGGGCAGAGGGGAGGAGG
TCGTCTGGTGCCTGGATGACAAGGCCAACTCCTTGGTGATGTACCACTCCACC
ACCTACCAGCTGTGTGCCCGGTACTTCTGCGGGGTCCCCAGCCCCCTCAGGGA
CATGTTTCCCGTGCGGCCCTTGGACACGGAACCCCCGGCAGCCAGCCACACGG
CCAACCCAAAGGTGCCTGAGGGGGACTCCATCGCGGACGTGAGCATCATGTAC
AGTGAGGAGCTGGGCACGCAGATCCTGATCCACCAGGAATCACTCACTGACTA
CTGCTCCATGTCCTCCTACTCCTCATCCCCACCCCGCCAGGCTGCCAGGTCCC
CCTCAAGCCTCCCCAGCTCCCCAGCAAGTTCTTCCAGTGTGCCTTTCTCCACC
GACTGCGAGGACTCAGACATGCTACATACGCCCGGTGCTGCCTCCGACAGGTC
TGAGCATGACCTGACCCCCATGGACGGGGAGACCTTCAGCCAGCACCTGCAGG
CCGTGAAGATCCTCGCCGTCAGAGACCTCATTTGGGTCCCCAGGCGCGGTGGA
GATGTTATCGTCATTGGCCTGGAGAAGGATTCTGAAGCCCAGCGGGGCCGAGT
CATTGCCGTCTTAAAAGCCCGAGAGCTGACTCCGCATGGGGTGCTGGTGGATG
CTGCCGTGGTGGCAAAGGACACTGTTGTGCACCTTTGAAAATGAAAACACA
GAGTGGTGCCTGGCCGTCTGGAGGGGCTGGGGCGCCAGGGAGTTCGACATTTT
CTACCAGTCCTACGAGGAGCTGGGCCGGCTGGAGGCTTGCACTCGCAAGAGAA
GGTAATTCCTGTGGAATGACTGTCACACA
```

Fig. 11

BLASTP - alignment of 423 against swiss|P80192|M3K9_HUMAN

MITOGEN-ACTIVATED PROTEIN KINASE KINASE KINASE 9 (EC 2.7.1.-) (MIXED LINEAGE KINASE 1) (FRAGMENT).

This hit is scoring at : 5e-23 (expectation value)
Alignment length (overlap) : 287
Identities : 31 %
Scoring matrix : BLOSUM62 (used to infer consensus pattern)
Database searched : nrdb_1_;

```
                          bind ATP
Q:  24 VLGQGGSGTVIYRARYQGQPVAVKRFHIKKFKNFANVPADTMLRHLRATDAMKNFSEFRQ
       ::G GG G.V YRA.: G..VAVK.                    .RH .D.:...RQ
H:   8 IIGIGGFGKV-YRAFWIGDEVAVKA--------------------ARHDPDEDISQTIENVRQ active site residue
       EASMLHALQHPCIVALIGISIHP--LCFALELAPLSSLNTVLSENARDSSFIPLGHMLTQ
       EA.:..L:HP I:AL G:.:..  LC..:E.A ..LN.VLS.:       IP .::.
       EAKLFAMLKHPNIIALRGVCLKEPNLCLVMEFARGGPLNRVLSGKR-----IPPDILVNW KIAYQIASGLAYLHKKNI---IFCDLKSDNILVWSL----DVKEHINIKLSDYGISRQSF
       A.QIA.G: YLH.:  YLH.:   I  I. DLKS.NIL:    D:...I :K::D:G::R:.
       -AVQIARGMNYLHDEAIVPIIHRDLKSSNILILQKVENGDLSNKI-LKITDFGLAREWH HEGALGVEGTPGYQAPEIRPRIVYDEKVDMFSYGMVLYELLSGQRPALGHHQLQIA----
       .:...GT..:APE:. .:APE:  :::.   D::SYG::L:ELL:G: P  G  L::A
       RTTKMSAAGTYAWMAPEVIRASMFSKGSDVWSYGVLLWELLTGEVPFFRGIDGLRVAYGVA -KKLSKGIRPVLGQPEEVQFRRLQALMMECWDTKPEKRP              284
        KL: I  ..:P             ..LM :CW:...P..RP
       MNKLALPIPSTCPEP---------FAKLMEDCWNPDPHSRP            249
```

Fig. 12

HMMPFAM - alignment of 423 against pfam|hmm|pkinase

Eukaryotic protein kinase domain

```
This hit is scoring at : 161.2                     E=2.6e-42
Scoring matrix : BLOSUM62 (used to infer consensus pattern)

Q:  19 EDEGSVLGQGGSGTViYRARYQ-GQPVAVKRFHIKKFKnfanvpadtmlrhlratdamkn
        :  LG:G. G.V Y:A::: G: VAVK
H:   1 yelleklGeGsfGkV.ykakhktgkivAvKilkkesls..........

fsefRQEASMLHALQHPCIVALIGISI---HPLCFALELAPLSSLNTVLSENArdssfiP
        :E..:L..L.HP IV.L:G:      L  .:E..:.L .:L..N.        P
       ...lrEiqilkrlsHpNIvrllgvfedtddhlylvmEymeggGdLfdylrrng......p LGHMLTQKIAYQIASGLAYLHKKNIIFCDLKSDNILVWSLdvkehINIKLSDYGISRQSf
       L..:KIA.QI..GL.YLH...I:. DLK.:NIL:          :K::D:G::R
       lsekeakkialQilrGleYLHsngivHRDLKpeNILlden......gtvKiaDFGLArll.

hEGALGVEGTPGYQ-APEI--RPrIVYDEKVDMFSYGMVLYELLSG------------
       E       GTP Y. APE:    .  Y..KVD::S.G::LYELL:G
       .eklttfvGTpwYmmAPEvileg.rgysskvDvWSlGviLyElltggplfpgadlpaftg --------QRPALGH------HQLQIAKKLSKG-IRPVLGQPEEvqfrrLQALMME
         :P      .    :    .  L: ::K  .       .EE       L:L::
       gdevdqliifvlklPfsdelpktridpleelfrikkrrlplpsncSee......lkdLlkk CWDTKPEK    286
C :..P.K
cLnkDPsk    262
```

REGULATION OF HUMAN PROTEIN KINASE-LIKE PROTEIN

This application is a National Stage application of co-pending PCT application PCT/EP02/02887 filed Mar. 15, 2002, which was published in English under PCT Article 21(2) on Oct. 17, 2002, which claims the benefit of U.S. provisional application Ser. No. 60/276,055 filed Mar. 16, 2001, Ser. No. 60/324,053 filed Sep. 24, 2001, Ser. No. 60/326,458 filed Oct. 3, 2001, and Ser. No. 60/337,124 filed Dec. 10, 2001. These applications are incorporated herein by reference in their entireties.

TECHNICAL FIELD OF THE INVENTION

The invention relates to the regulation of a human protein kinase-like protein.

BACKGROUND OF THE INVENTION

Protein kinases play critical roles in the regulation of biochemical and morphological changes associated with cellular growth and division. D'Urso et al., *Science* 250, 786–91, 1990; Birchmeier et al., *Bioessays* 15, 185–89, 1993); U.S. Pat. No. 6,200,770. They serve as growth factor receptors and signal transducers and have been implicated in cellular transformation and malignancy. Hunter et al., *Cell* 70, 375–87, 1992; Posada et al., *Mol. Biol. Cell* 3, 583–92, 1992; Hunter et al., *Cell* 79, 573–82, 1994. For example, protein kinases have been shown to participate in the transmission of signals from growth-factor receptors (Sturgill et al., *Nature* 344, 715–18, 1988; Gomez et al., *Nature* 353, 170–73, 1991), control of entry of cells into mitosis (Nurse et al., *Nature* 344, 503–08, 1990; Maller, *Curr. Opin. Cell Biol.* 3, 269–75, 1991), and regulation of actin bundling (Husain-Chishti et al., *Nature* 334, 718–21, 1988).

Protein kinases can be divided into two main groups based on either amino acid sequence similarity or specificity for either serine/threonine or tyrosine residues. A small number of dual-specificity kinases are structurally like the serine/threonine-specific group. Within the broad classification, kinases can be further sub-divided into families whose members share a higher degree of catalytic domain amino acid sequence identity and also have similar biochemical properties. Most protein kinase family members also share structural features outside the kinase domain that reflect their particular cellular roles. These include regulatory domains that control kinase activity or interaction with other proteins. Hanks et al., *Science* 241, 42–52, 1988).

There is a need in the art to identify protein kinase-like proteins, which can be regulated to provide therapeutic effects.

SUMMARY OF THE INVENTION

It is an object of the invention to provide reagents and methods of regulating a human protein kinase-like protein. This and other objects of the invention are provided by one or more of the embodiments described below.

One embodiment of the invention is a proteine kinase-like protein polypeptide comprising an amino acid sequence selected from the group consisting of:
amino acid sequences which are at least about 35% identical to the amino acid sequence shown in SEQ ID NO: 2;
the amino acid sequence shown in SEQ ID NO: 2;
amino acid sequences which are at least about 35% identical to the amino acid sequence shown in SEQ ID NO: 9 and;
the amino acid sequence shown in SEQ ID NO:9.

Yet another embodiment of the invention is a method of screening for agents which decrease extracellular matrix degradation. A test compound is contacted with a proteine kinase-like protein polypeptide comprising an amino acid sequence selected from the group consisting of:
amino acid sequences which are at least about 35% identical to the amino acid sequence shown in SEQ ID NO: 2;
the amino acid sequence shown in SEQ ID NO: 2;
amino acid sequences which are at least about 50% identical to the amino acid sequence shown in SEQ ID NO: 9 and;
the amino acid sequence shown in SEQ ID NO:9.

Binding between the test compound and the proteine kinase-like protein polypeptide is detected. A test compound which binds to the proteine kinase-like protein polypeptide is thereby identified as a potential agent for decreasing extracellular matrix degradation. The agent can work by decreasing the activity of the proteine kinase-like protein.

Another embodiment of the invention is a method of screening for agents which decrease extracellular matrix degradation. A test compound is contacted with a polynucleotide encoding a proteine kinase-like protein polypeptide, wherein the polynucleotide comprises a nucleotide sequence selected from the group consisting of:
nucleotide sequences which are at least about 50% identical to the nucleotide sequence shown in SEQ ID NO: 1;
the nucleotide sequence shown in SEQ ID NO: 1;
nucleotide sequences which are at least about 50% identical to the nucleotide sequence shown in SEQ ID NO: 8;
the nucleotide sequence shown in SEQ ID NO: 8;
nucleotide sequences which are at least about 50% identical to the nucleotide sequence shown in SEQ ID NO: 10; and
the nucleotide sequence shown in SEQ ID NO: 10.

Binding of the test compound to the polynucleotide is detected. A test compound which binds to the polynucleotide is identified as a potential agent for decreasing extracellular matrix degradation. The agent can work by decreasing the amount of the proteine kinase-like protein through interacting with the proteine kinase-like protein mRNA.

Another embodiment of the invention is a method of screening for agents which regulate extracellular matrix degradation. A test compound is contacted with a proteine kinase-like protein polypeptide comprising an amino acid sequence selected from the group consisting of:
amino acid sequences which are at least about 35% identical to the amino acid sequence shown in SEQ ID NO: 2;
the amino acid sequence shown in SEQ ID NO: 2;
amino acid sequences which are at least about 35% identical to the amino acid sequence shown in SEQ ID NO: 9 and;
the amino acid sequence shown in SEQ ID NO:9.

A proteine kinase-like protein activity of the polypeptide is detected. A test compound which increases proteine kinase-like protein activity of the polypeptide relative to proteine kinase-like protein activity in the absence of the test compound is thereby identified as a potential agent for increasing extracellular matrix degradation. A test compound which decreases proteine kinase-like protein activity of the polypeptide relative to proteine kinase-like protein activity in the absence of the test compound is thereby identified as a potential agent for decreasing extracellular matrix degradation.

Even another embodiment of the invention is a method of screening for agents which decrease extracellular matrix degradation. A test compound is contacted with a proteine kinase-like protein product of a polynucleotide which comprises a nucleotide sequence selected from the group consisting of:

nucleotide sequences which are at least about 50% identical to the nucleotide sequence shown in SEQ ID NO: 1;
the nucleotide sequence shown in SEQ ID NO: 1;
nucleotide sequences which are at least about 50% identical to the nucleotide sequence shown in SEQ ID NO: 8;
the nucleotide sequence shown in SEQ ID NO: 8;
nucleotide sequences which are at least about 50% identical to the nucleotide sequence shown in SEQ ID NO: 10; and
the nucleotide sequence shown in SEQ ID NO:10.

Binding of the test compound to the proteine kinase-like protein product is detected. A test compound which binds to the proteine kinase-like protein product is thereby identified as a potential agent for decreasing extracellular matrix degradation.

Still another embodiment of the invention is a method of reducing extracellular matrix degradation. A cell is contacted with a reagent which specifically binds to a polynucleotide encoding a proteine kinase-like protein polypeptide or the product encoded by the polynucleotide, wherein the polynucleotide comprises a nucleotide sequence selected from the group consisting of:
nucleotide sequences which are at least about 50% identical to the nucleotide sequence shown in SEQ ID NO: 1;
the nucleotide sequence shown in SEQ ID NO: 1;
nucleotide sequences which are at least about 50% identical to the nucleotide sequence shown in SEQ ID NO: 8;
the nucleotide sequence shown in SEQ ID NO: 8;
nucleotide sequences which are at least about 50% identical to the nucleotide sequence shown in SEQ ID NO: 10; and
the nucleotide sequence shown in SEQ ID NO: 10.

Proteine kinase-like protein activity in the cell is thereby decreased.

The invention thus provides a human protein kinase-like protein that can be used to identify test compounds that may act, for example, as activators or inhibitors at the enzyme's active site. Human protein kinase-like protein and fragments thereof also are useful in raising specific antibodies that can block the enzyme and effectively reduce its activity.

BRIEF DESCRIPTION OF THE DRAWINGS

FIG. 1 shows the DNA-sequence encoding a proteine kinase-like protein Polypeptide (SEQ ID NO:1).
FIG. 2 shows the amino acid sequence deduced from the DNA-sequence of FIG. 1 (SEQ ID NO:2).
FIG. 3 shows the amino acid sequence of the protein identified by swiss|P80192|M3K9_HUMAN (SEQ ID NO:3).
FIG. 4 shows the DNA-sequence encoding a proteine kinase-like protein Polypeptide (SEQ ID NO:4).
FIG. 5 shows the DNA-sequence encoding a proteine kinase-like protein Polypeptide (SEQ ID NO:5).
FIG. 6 shows the DNA-sequence encoding a proteine kinase-like protein Polypeptide (SEQ ID NO:6).
FIG. 7 shows the DNA-sequence encoding a proteine kinase-like protein Polypeptide (SEQ ID NO:7).
FIG. 8 shows the DNA-sequence encoding a proteine kinase-like protein Polypeptide (SEQ ID NO:8).
FIG. 9 shows the amino acid sequence deduced from the DNA-sequence of FIG. 8 (SEQ ID NO:9).
FIG. 10 shows the DNA-sequence encoding a proteine kinase-like protein Polypeptide (SEQ ID NO:10).
FIG. 11 shows the BLASTP—alignment of 423 (SEQ ID NO:2) against swiss|P80192|M3K9_HUMAN (SEQ ID NO:3).
FIG. 12 shows the HMMPFAM—alignment of 423 (SEQ ID NO:2) against pfam|hmm|pkinase.

DETAILED DESCRIPTION OF THE INVENTION

Figure 13:
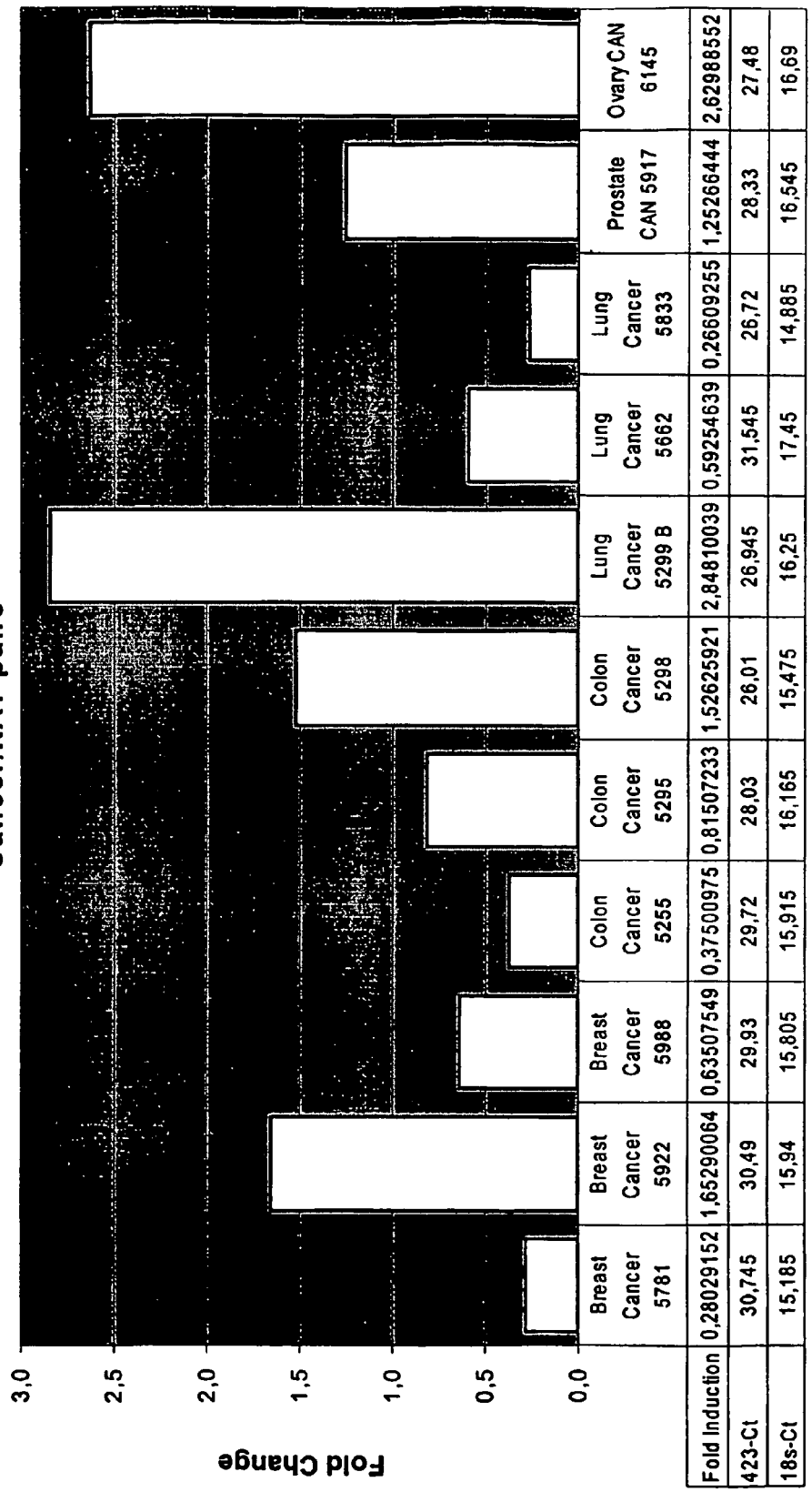
FIG. 13 shows the relative expression of human protein kinase-like protein mRNA in cancer cells and tissue.

The invention relates to an isolated polynucleotide from the group consisting of:
a) a polynucleotide encoding a proteine kinase-like protein polypeptide comprising an amino acid sequence selected from the group consisting of:
   amino acid sequences which are at least about 35% identical to the amino acid sequence shown in SEQ ID NO: 2;
   the amino acid sequence shown in SEQ ID NO: 2;
   amino acid sequences which are at least about 35% identical to the amino acid sequence shown in SEQ ID NO: 9 and;
   the amino acid sequence shown in SEQ ID NO:9.
b) a polynucleotide comprising the sequence of SEQ ID NOS: 1, 8 or 10;
c) a polynucleotide which hybridizes under stringent conditions to a polynucleotide specified in (a) and (b) and encodes a proteine kinase-like protein polypeptide;
d) a polynucleotide the sequence of which deviates from the polynucleotide sequences specified in (a) to (c) due to the degeneration of the genetic code and encodes a proteine kinase-like protein polypeptide; and
e) a polynucleotide which represents a fragment, derivative or allelic variation of a polynucleotide sequence specified in (a) to (d) and encodes a proteine kinase-like protein polypeptide.

Furthermore, it has been discovered by the present applicant that a novel protein kinase-like protein, particularly a human protein kinase-like protein, can be used in therapeutic methods to treat cancer, a CNS disorder, COPD, obesity, diabetes, or a cardiovascular disorder.

Human protein kinase-like protein comprises the amino acid sequence shown in SEQ ID NOS:2 and 9. A coding sequence for human protein kinase-like protein is shown in SEQ ID NOS: 1, 8 and 10. This sequence is located on chromosome 15. Related ESTs (SEQ ID NOS:4–7) are expressed in lymphoma and germinal center B cells.

Human protein kinase-like protein is 31% identical over 287 amino acids to swiss|P80192|M3K9_HUMAN (SEQ ID NO:3) (FIG. 1). Pfam homology search results support the identification of this protein as a eukaryotic protein kinase. Its likely function as a tyrosine kinase class m protein also is supported by the results of a BLOCKS database search. Consensus patterns are underlined in FIG. 1; the active site Asp residue and the ATP-binding Lys residue are highlighted in bold.

Human protein kinase-like protein of the invention is expected to be useful for the same purposes as previously identified protein kinase-like protein enzymes. Human protein kinase-like protein is believed to be useful in therapeutic methods to treat disorders such as cancer, CNS disorders, COPD, obesity, diabetes, and cardiovascular disorders.

Human protein kinase-like protein also can be used to screen for human protein kinase-like protein activators and inhibitors.

Polypeptides

Human protein kinase-like polypeptides according to the invention comprise at least 6, 10, 15, 20, 25, 50, 75, 100, 125, 150, 175, 200, 225, 250, 275, or 286 contiguous amino acids selected from the amino acid sequence shown in SEQ ID NO:2 or a biologically active variant thereof, as defined below. Human protein kinase-like polypeptides according to the invention comprise at least 6, 10, 15, 20, 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, 1275, 1300, 1325, 1350, 1375 or 1394 contiguous amino acids selected from the amino acid sequence shown in SEQ ID NO:9 or a biologically active variant thereof, as defined below. A protein kinase-like polypeptide of the invention therefore can be a portion of a protein kinase-like protein, a full-length protein kinase-like protein, or a fusion protein comprising all or a portion of a protein kinase-like protein.

Biologically Active Variants

Human protein kinase-like polypeptide variants which are biologically active, e.g., retain enzymatic activity, also are human protein kinase-like polypeptides. Preferably, naturally or non-naturally occurring human protein kinase-like polypeptide variants have amino acid sequences which are at least about 32, 35, 40, 45, 50, 55, 60, 65, or 70, preferably about 75, 80, 85, 90, 96, 96, 98, or 99% identical to the amino acid sequence shown in SEQ ID NOS:2 and 9 or a fragment thereof. Percent identity between a putative human protein kinase-like polypeptide variant and an amino acid sequence of SEQ ID NO:2 or 9 is determined by conventional methods. See, for example, Altschul et al., *Bull. Math. Bio.* 48:603 (1986), and Henikoff & Henikoff, *Proc. Natl. Acad. Sci. USA* 89:10915 (1992). Briefly, two amino acid sequences are aligned to optimize the alignment scores using a gap opening penalty of 10, a gap extension penalty of 1, and the "BLOSUM62" scoring matrix of Henikoff & Henikoff, 1992.

Those skilled in the art appreciate that there are many established algorithms available to align two amino acid sequences. The "FASTA" similarity search algorithm of Pearson & Lipman is a suitable protein alignment method for examining the level of identity shared by an amino acid sequence disclosed herein and the amino acid sequence of a putative variant. The FASTA algorithm is described by Pearson & Lipman, *Proc. Nat'l Acad. Sci. USA* 85:2444 (1988), and by Pearson, *Meth. Enzymol.* 183:63 (1990). Briefly, FASTA first characterizes sequence similarity by identifying regions shared by the query sequence (e.g., SEQ ID NO: 2 or 9) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman & Wunsch, *J. Mol. Biol.*48: 444 (1970); Sellers, *SIAM J. Appl. Math.*26:787 (1974)), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, *Meth. Enzymol.* 183:63 (1990).

FASTA can also be used to determine the sequence identity of nucleic acid molecules using a ratio as disclosed above. For nucleotide sequence comparisons, the ktup value can range between one to six, preferably from three to six, most preferably three, with other parameters set as default.

Variations in percent identity can be due, for example, to amino acid substitutions, insertions, or deletions. Amino acid substitutions are defined as one for one amino acid replacements. They are conservative in nature when the substituted amino acid has similar structural and/or chemical properties. Examples of conservative replacements are substitution of a leucine with an isoleucine or valine, an aspartate with a glutamate, or a threonine with a serine.

Amino acid insertions or deletions are changes to or within an amino acid sequence. They typically fall in the range of about 1 to 5 amino acids. Guidance in determining which amino acid residues can be substituted, inserted, or deleted without abolishing biological or immunological activity of a human protein kinase-like polypeptide can be found using computer programs well known in the art, such as DNASTAR software.

The invention additionally, encompasses protein kinase-like polypeptides that are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications can be carried out by known techniques including, but not limited, to specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The protein kinase-like polypeptides may also be modified with a detectable label, such as an enzymatic, fluorescent, isotopic or affinity label to allow for detection and isolation of the protein.

The invention also provides chemically modified derivatives of protein kinase-like polypeptides that may provide additional advantages such as increased solubility, stability and circulating time of the polypeptide, or decreased immunogenicity (see U.S. Pat. No. 4,179,337). The chemical moieties for derivitization can be selected from water soluble polymers such as polyethylene glycol, ethylene glycol/propylene glycol copolymers, carboxymethylcellulose, dextran, polyvinyl alcohol, and the like. The polypeptides can be modified at random or predetermined positions within the molecule and can include one, two, three, or more attached chemical moieties.

Whether an amino acid change or a polypeptide modification results in a biologically active protein kinase-like polypeptide can readily be determined by assaying for enzymatic activity, as described for example, in U.S. Pat. No. 6,194,186.

Fusion Proteins

Fusion proteins are useful for generating antibodies against protein kinase-like polypeptide amino acid sequences and for use in various assay systems. For example, fusion proteins can be used to identify proteins that interact with portions of a protein kinase-like polypeptide. Protein affinity chromatography or library-based assays for protein-protein interactions, such as the yeast two-hybrid or phage display systems, can be used for this purpose. Such methods are well known in the art and also can be used as drug screens.

A protein kinase-like polypeptide fusion protein comprises two polypeptide segments fused together by means of a peptide bond. The first polypeptide segment comprises at least 6, 10, 15, 20, 25, 50, 75, 100, 125, 150, 175, 200, 225, 250, 275, or 286 contiguous amino acids of SEQ D NOS:2 or of a biologically active variant, such as those described above. The first polypeptide segment comprises at least 6, 10, 15, 20, 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, 1000, 1025, 1050, 1075, 1100, 1125, 1150, 1175, 1200, 1225, 1250, 1275, 1300, 1325, 1350, 1375 or 1394 contiguous amino acids of SEQ ID NOS:2 or of a biologically active variant, such as those described above. The first polypeptide segment also can comprise full-length protein kinase-like protein.

The second polypeptide segment can be a full-length protein or a protein fragment. Proteins commonly used in fusion protein construction include 13-galactosidase, P-glucuronidase, green fluorescent protein (GFP), autofluorescent proteins, including blue fluorescent protein (BFP), glutathione-S-transferase (GST), luciferase, horseradish peroxidase (HRP), and chloramphenicol acetyltransferase (CAT). Additionally, epitope tags are used in fusion protein constructions, including histidine (His) tags, FLAG tags, influenza hemagglutinin (HA) tags, Myc tags, VSV-G tags, and thioredoxin (Trx) tags. Other fusion constructions can include maltose binding protein (MBP), S-tag, Lex a DNA binding domain (DBD) fusions, GALA DNA binding domain fusions, and herpes simplex virus (HSV) BP16 protein fusions. A fusion protein also can be engineered to contain a cleavage site located between the protein kinase-like polypeptide-encoding sequence and the heterologous protein sequence, so that the protein kinase-like polypeptide can be cleaved and purified away from the heterologous moiety.

A fusion protein can be synthesized chemically, as is known in the art. Preferably, a fusion protein is produced by covalently linking two polypeptide segments or by standard procedures in the art of molecular biology. Recombinant DNA methods can be used to prepare fusion proteins, for example, by making a DNA construct which comprises coding sequences selected from SEQ ID NOS: 1, 8 and 10 in proper reading frame with nucleotides encoding the second polypeptide segment and expressing the DNA construct in a host cell, as is known in the art. Many kits for constructing fusion proteins are available from companies such as Promega Corporation (Madison, Wis.), Stratagene (La Jolla, Calif.), CLONTECH (Mountain View, Calif.), Santa Cruz Biotechnology (Santa Cruz, Calif.), MBL International Corporation (MIC; Watertown, Mass.), and Quantum Biotechnologies (Montreal, Canada; 1-888-DNA-KITS).

Identification of Species Homologs

Species homologs of human protein kinase-like polypeptide can be obtained using protein kinase-like polypeptide polynucleotides (described below) to make suitable probes or primers for screening cDNA expression libraries from other species, such as mice, monkeys, or yeast, identifying cDNAs which encode homologs of protein kinase-like polypeptide, and expressing the cDNAs as is known in the art.

Polynucleotides

A protein kinase-like polynucleotide can be single- or double-stranded and comprises a coding sequence or the complement of a coding sequence for a protein kinase-like polypeptide. A coding sequence for human protein kinase-like protein is shown in SEQ ID NOS: 1, 8 and 10.

Degenerate nucleotide sequences encoding human protein kinase-like polypeptides, as well as homologous nucleotide sequences which are at least about 50, 55, 60, 65, 70, preferably about 75, 90, 96, 98, or 99% identical to the nucleotide sequence shown in SEQ ID NOS: 1, 8 and 10 or its complement also are protein kinase-like polynucleotides. Percent sequence identity between the sequences of two polynucleotides is determined using computer programs such as ALIGN which employ the FASTA algorithm, using an affine gap search with a gap open penalty of −12 and a gap extension penalty of −2. Complementary DNA (cDNA) molecules, species homologs, and variants of protein kinase-like polynucleotides that encode biologically active protein kinase-like polypeptides also are protein kinase-like polynucleotides. Polynucleotide fragments comprising at least 8, 9, 10, 11, 12, 15, 20, or 25 contiguous nucleotides of SEQ ID NOS: 1, 8 and 10 or its complement also are protein kinase-like polynucleotides. These fragments can be used, for example, as hybridization probes or as antisense oligonucleotides.

Identification of Polynucleotide Variants and Homologs

Variants and homologs of the protein kinase-like polynucleotides described above also are protein kinase-like polynucleotides. Typically, homologous protein kinase-like polynucleotide sequences can be identified by hybridization of candidate polynucleotides to known protein kinase-like polynucleotides under stringent conditions, as is known in the art. For example, using the following wash conditions—2×SSC (0.3 M NaCl, 0.03 M sodium citrate, pH 7.0), 0.1% SDS, room temperature twice, 30 minutes each; then 2×SSC, 0.1% SDS, 50° C. once, 30 minutes; then 2×SSC, room temperature twice, 10 minutes each—homologous sequences can be identified which contain at most about 25–30% basepair mismatches. More preferably, homologous nucleic acid strands contain 15–25% basepair mismatches, even more preferably 5–15% basepair mismatches.

Species homologs of the protein kinase-like polynucleotides disclosed herein also can be identified by making suitable probes or primers and screening cDNA expression libraries from other species, such as mice, monkeys, or yeast. Human variants of protein kinase-like polynucleotides can be identified, for example, by screening human cDNA expression libraries. It is well known that the $T_m$ of a double-stranded DNA decreases by 1–1.5° C. with every 1% decrease in homology (Bonner et al., *J. Mol. Biol.* 81, 123 (1973). Variants of human protein kinase-like polynucleotides or protein kinase-like polynucleotides of other species can therefore be identified by hybridizing a putative homologous protein kinase-like polynucleotide with a polynucleotide having a nucleotide sequence of SEQ ID NOS: 1, 8 and 10 or the complement thereof to form a test hybrid. The melting temperature of the test hybrid is compared with the melting temperature of a hybrid comprising polynucleotides having perfectly complementary nucleotide sequences, and the number or percent of basepair mismatches within the test hybrid is calculated.

Nucleotide sequences which hybridize to protein kinase-like polynucleotides or their complements following stringent hybridization and/or wash conditions also are protein kinase-like polynucleotides. Stringent wash conditions are well known and understood in the art and are disclosed, for example, in Sambrook et al., MOLECULAR CLONING: A LABORATORY MANUAL, 2d ed., 1989, at pages 9.50–9.51.

Typically, for stringent hybridization conditions a combination of temperature and salt concentration should be chosen that is approximately 12–20° C. below the calculated $T_m$ of the hybrid under study. The $T_m$ of a hybrid between a protein kinase-like polynucleotide having a nucleotide sequence shown in SEQ ID NOS: 1, 8 and 10 or the complement thereof and a polynucleotide sequence which is at least about 50, preferably about 75, 90, 96, or 98% identical to one of those nucleotide sequences can be calculated, for example, using the equation of Bolton and McCarthy, *Proc. Natl. Acad. Sci. U.S.A.* 48, 1390 (1962):

$$T_m = 81.5° C. - 16.6(\log_{10}[Na^+]) - 0.41(\% G+C) - 0.63(\% formamide) - 600/l,$$

where l=the length of the hybrid in basepairs.

Stringent wash conditions include, for example, 4×SSC at 65° C., or 50% formamide, 4×SSC at 42° C., or 0.5×SSC, 0.1% SDS at 65° C. Highly stringent wash conditions include, for example, 0.2×SSC at 65° C.

Preparation of Polynucleotides

A protein kinase-like polynucleotide can be isolated free of other cellular components such as membrane components, proteins, and lipids. Polynucleotides can be made by a cell and isolated using standard nucleic acid purification techniques, or synthesized using an amplification technique, such as the polymerase chain reaction (PCR), or by using an automatic synthesizer. Methods for isolating polynucleotides are routine and are known in the art. Any such technique for obtaining a polynucleotide can be used to obtain isolated protein kinase-like polynucleotides. For example, restriction enzymes and probes can be used to isolate polynucleotide fragments, which comprise protein kinase-like protein nucleotide sequences. Isolated polynucleotides are in preparations that are free or at least 70, 80, or 90% free of other molecules.

Human protein kinase-like cDNA molecules can be made with standard molecular biology techniques, using protein kinase-like mRNA as a template. Human protein kinase-like cDNA molecules can thereafter be replicated using molecular biology techniques known in the art and disclosed in manuals such as Sambrook et al. (1989). An amplification technique, such as PCR, can be used to obtain additional copies of polynucleotides of the invention, using either human genomic DNA or cDNA as a template.

Alternatively, synthetic chemistry techniques can be used to synthesize protein kinase-like polynucleotides. The degeneracy of the genetic code allows alternate nucleotide sequences to be synthesized which will encode a protein kinase-like polypeptide having, for example, an amino acid sequence shown in SEQ ID NOS:2 and 9 or a biologically active variant thereof.

Extending Polynucleotides

The partial sequence disclosed herein can be used to identify the corresponding full length gene from which it was derived. The partial sequence can be nick-translated or end-labeled with $^{32}P$ using polynucleotide kinase using labeling methods known to those with skill in the art (BASIC METHODS IN MOLECULAR BIOLOGY, Davis et al., eds., Elsevier Press, N.Y., 1986). A lambda library prepared from human tissue can be directly screened with the labeled sequences of interest or the library can be converted en masse to pBluescript (Stratagene Cloning Systems, La Jolla, Calif. 92037) to facilitate bacterial colony screening (see Sambrook et al., MOLECULAR CLONING: A LABORATORY MANUAL, Cold Spring Harbor Laboratory Press (1989, pg. 1.20).

Both methods are well known in the art. Briefly, filters with bacterial colonies containing the library in pBluescript or bacterial lawns containing lambda plaques are denatured, and the DNA is fixed to the filters. The filters are hybridized with the labeled probe using hybridization conditions described by Davis et al., 1986. The partial sequences, cloned into lambda or pBluescript, can be used as positive controls to assess background binding and to adjust the hybridization and washing stringencies necessary for accurate clone identification. The resulting autoradiograms are compared to duplicate plates of colonies or plaques; each exposed spot corresponds to a positive colony or plaque. The colonies or plaques are selected, expanded and the DNA is isolated from the colonies for further analysis and sequencing.

Positive cDNA clones are analyzed to determine the amount of additional sequence they contain using PCR with one primer from the partial sequence and the other primer from the vector. Clones with a larger vector-insert PCR product than the original partial sequence are analyzed by restriction digestion and DNA sequencing to determine whether they contain an insert of the same size or similar as the mRNA size determined from Northern blot Analysis.

Once one or more overlapping cDNA clones are identified, the complete sequence of the clones can be determined, for example after exonuclease III digestion (McCombie et al., *Methods* 3, 33–40, 1991). A series of deletion clones are generated, each of which is sequenced. The resulting overlapping sequences are assembled into a single contiguous sequence of high redundancy (usually three to five overlapping sequences at each nucleotide position), resulting in a highly accurate final sequence.

Various PCR-based methods can be used to extend the nucleic acid sequences disclosed herein to detect upstream sequences such as promoters and regulatory elements. For example, restriction-site PCR uses universal primers to retrieve unknown sequence adjacent to a known locus (Sarkar, *PCR Methods Applic.* 2, 318–322, 1993). Genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR also can be used to amplify or extend sequences using divergent primers based on a known region (Triglia et al., *Nucleic Acids Res.* 16, 8186, 1988). Primers can be designed using commercially available software, such as OLIGO 4.06 Primer Analysis software (National Biosciences Inc., Plymouth, Minn.), to be 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template.

Another method which can be used is capture PCR, which involves PCR amplification of DNA fragments adjacent to a known sequence in human and yeast artificial chromosome DNA (Lagerstrom et al., *PCR Methods Applic.* 1, 111–119, 1991). In this method, multiple restriction enzyme digestions and ligations also can be used to place an engineered double-stranded sequence into an unknown fragment of the DNA molecule before performing PCR.

Another method which can be used to retrieve unknown sequences is that of Parker et al., *Nucleic Acids Res.* 19, 3055–3060, 1991). Additionally, PCR, nested primers, and PROMOTERFINDER libraries (CLONTECH, Palo Alto, Calif) can be used to walk genomic DNA (CLONTECH, Palo Alto, Calif.). This process avoids the need to screen libraries and is useful in finding intron/exon junctions.

When screening for full-length cDNAs, it is preferable to use libraries that have been size-selected to include larger cDNAs. Randomly-primed libraries are preferable, in that they will contain more sequences which contain the 5' regions of genes. Use of a randomly primed library may be especially preferable for situations in which an oligo d(T) library does not yield a full-length cDNA. Genomic libraries can be useful for extension of sequence into 5' non-transcribed regulatory regions.

Commercially available capillary electrophoresis systems can be used to analyze the size or confirm the nucleotide sequence of PCR or sequencing products. For example, capillary sequencing can employ flowable polymers for electrophoretic separation, four different fluorescent dyes (one for each nucleotide) that are laser activated, and detection of the emitted wavelengths by a charge coupled device camera. Output/light intensity can be converted to electrical signal using appropriate software (e.g. GENOTYPER and Sequence NAVIGATOR, Perkin Elmer), and the entire process from loading of samples to computer analysis and electronic data display can be computer controlled. Capillary electrophoresis is especially preferable for the sequencing of small pieces of DNA that might be present in limited amounts in a particular sample.

Obtaining Polypeptides

Human protein kinase-like polypeptides can be obtained, for example, by purification from human or other cells, by expression of protein kinase-like polynucleotides, or by direct chemical synthesis.

Protein Purification

Human protein kinase-like polypeptides can be purified from any cell that expresses the polypeptide, including host cells that have been transfected with protein kinase-like protein expression constructs. A purified protein kinase-like polypeptide is separated from other compounds that normally associate with the protein kinase-like polypeptide in the cell, such as certain proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis. A preparation of purified protein kinase-like polypeptides is at least 80% pure; preferably, the preparations are 90%, 95%, or 99% pure. Purity of the preparations can be assessed by any means known in the art, such as SDS-polyacrylamide gel electrophoresis.

Expression of Polynucleotides

To express a protein kinase-like polynucleotide, the polynucleotide can be inserted into an expression vector that contains the necessary elements for the transcription and translation of the inserted coding sequence. Methods that are well known to those skilled in the art can be used to construct expression vectors containing sequences encoding protein kinase-like polypeptides and appropriate transcriptional and translational control elements. These methods include in vitro recombinant DNA techniques, synthetic techniques, and in vivo genetic recombination. Such techniques are described, for example, in Sambrook et al. (1989) and in Ausubel et al., CURRENT PROTOCOLS IN MOLECULAR BIOLOGY, John Wiley & Sons, New York, N.Y., 1989.

A variety of expression vector/host systems can be utilized to contain and express sequences encoding a protein kinase-like polypeptide. These include, but are not limited to, microorganisms, such as bacteria transformed with recombinant bacteriophage, plasmid, or cosmid DNA expression vectors; yeast transformed with yeast expression vectors, insect cell systems infected with virus expression vectors (e.g., baculovirus), plant cell systems transformed with virus expression vectors (e.g., cauliflower mosaic virus, CaMV; tobacco mosaic virus, TMV) or with bacterial expression vectors (e.g., Ti or pBR322 plasmids), or animal cell systems.

The control elements or regulatory sequences are those non-translated regions of the vector—enhancers, promoters, 5' and 3' untranslated regions—which interact with host cellular proteins to carry out transcription and translation. Such elements can vary in their strength and specificity. Depending on the vector system and host utilized, any number of suitable transcription and translation elements, including constitutive and inducible promoters, can be used. For example, when cloning in bacterial systems, inducible promoters such as the hybrid lacZ promoter of the BLUESCRIPT phagemid (Stratagene, LaJolla, Calif.) or pSPORT1 plasmid (Life Technologies) and the like can be used. The baculovirus polyhedrin promoter can be used in insect cells. Promoters or enhancers derived from the genomes of plant cells (e.g., heat shock, RUBISCO, and storage genes) or from plant viruses (e.g., viral promoters or leader sequences) can be cloned into the vector. In mammalian cell systems, promoters from mammalian genes or from mammalian viruses are preferable. If it is necessary to generate a cell line that contains multiple copies of a nucleotide sequence encoding a protein kinase-like polypeptide, vectors based on SV40 or EBV can be used with an appropriate selectable marker.

Bacterial and Yeast Expression Systems

In bacterial systems, a number of expression vectors can be selected depending upon the use intended for the protein kinase-like polypeptide. For example, when a large quantity of a protein kinase-like polypeptide is needed for the induction of antibodies, vectors which direct high level expression of fusion proteins that are readily purified can be used. Such vectors include, but are not limited to, multifunctional *E. coli* cloning and expression vectors such as BLUESCRIPT (Stratagene). In a BLUESCRIPT vector, a sequence encoding the protein kinase-like polypeptide can be ligated into the vector in frame with sequences for the amino-terminal Met and the subsequent 7 residues of β-galactosidase so that a hybrid protein is produced. pIN vectors (Van Heeke & Schuster, *J. Biol. Chem.* 264, 5503–5509, 1989) or pGEX vectors (Promega, Madison, Wis.) also can be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems can be designed to include heparin, thrombin, or factor Xa protease cleavage sites so that the cloned polypeptide of interest can be released from the GST moiety at will.

In the yeast *Saccharomyces cerevisiae*, a number of vectors containing constitutive or inducible promoters such as alpha factor, alcohol oxidase, and PGH can be used. For reviews, see Ausubel et al. (1989) and Grant et al., *Methods Enzymol.* 153, 516–544, 1987.

Plant and Insect Expression Systems

If plant expression vectors are used, the expression of sequences encoding protein kinase-like polypeptides can be driven by any of a number of promoters. For example, viral promoters such as the 35S and 19S promoters of CaMV can be used alone or in combination with the omega leader sequence from TMV (Takamatsu, *EMBO J.* 6, 307–311, 1987). Alternatively, plant promoters such as the small subunit of RUBISCO or heat shock promoters can be used (Coruzzi et al., *EMBO J.* 3, 1671–1680, 1984; Broglie et al., *Science* 224, 838–843, 1984; Winter et al., *Results Probl. Cell Differ.* 17, 85–105, 1991). These constructs can be introduced into plant cells by direct DNA transformation or by pathogen-mediated transfection. Such techniques are described in a number of generally available reviews (e.g., Hobbs or Murray, in McGraw Hill Yearbook of Science and Technology, McGraw Hill, New York, N.Y., pp. 191–196, 1992).

An insect system also can be used to express a protein kinase-like polypeptide. For example, in one such system *Autographa californica* nuclear polyhedrosis virus (AcNPV) is used as a vector to express foreign genes in *Spodoptera frugiperda* cells or in *Trichoplusia* larvae. Sequences encoding protein kinase-like polypeptides can be cloned into a non-essential region of the virus, such as the polyhedrin gene, and placed under control of the polyhedrin promoter. Successful insertion of protein kinase-like polypeptides will render the polyhedrin gene inactive and produce recombinant virus lacking coat protein. The recombinant viruses can then be used to infect *S. frugiperda* cells or *Trichoplusia* larvae in which protein kinase-like polypeptides can be expressed (Engelhard et al., *Proc. Nat. Acad. Sci.* 91, 3224–3227, 1994).

Mammalian Expression Systems

A number of viral-based expression systems can be used to express protein kinase-like polypeptides in mammalian host cells. For example, if an adenovirus is used as an expression vector, sequences encoding protein kinase-like polypeptides can be ligated into an adenovirus transcription/translation complex comprising the late promoter and tripartite leader sequence. Insertion in a non-essential E1 or E3 region of the viral genome can be used to obtain a viable virus that is capable of expressing a protein kinase-like polypeptide in infected host cells (Logan & Shenk, *Proc. Natl. Acad. Sci.* 81, 3655–3659, 1984). If desired, transcription enhancers, such as the Rous sarcoma virus (RSV) enhancer, can be used to increase expression in mammalian host cells.

Human artificial chromosomes (HACs) also can be used to deliver larger fragments of DNA than can be contained and expressed in a plasmid. HACs of 6M to 10M are constructed and delivered to cells via conventional delivery methods (e.g., liposomes, polycationic amino polymers, or vesicles).

Specific initiation signals also can be used to achieve more efficient translation of sequences encoding protein kinase-like polypeptides. Such signals include the ATG initiation codon and adjacent sequences. In cases where sequences encoding a protein kinase-like polypeptide, its initiation codon, and upstream sequences are inserted into the appropriate expression vector, no additional transcriptional or translational control signals may be needed. However, in cases where only coding sequence, or a fragment thereof, is inserted, exogenous translational control signals (including the ATG initiation codon) should be provided. The initiation codon should be in the correct reading frame to ensure translation of the entire insert. Exogenous translational elements and initiation codons can be of various origins, both natural and synthetic. The efficiency of expression can be enhanced by the inclusion of enhancers which are appropriate for the particular cell system which is used (see Scharf et al., *Results Probl. Cell Differ.* 20, 125–162, 1994).

Host Cells

A host cell strain can be chosen for its ability to modulate the expression of the inserted sequences or to process the expressed protein kinase-like polypeptide in the desired fashion. Such modifications of the polypeptide include, but are not limited to, acetylation, carboxylation, glycosylation, phosphorylation, lipidation, and acylation. Post-translational processing which cleaves a "prepro" form of the polypeptide also can be used to facilitate correct insertion, folding and/or function. Different host cells that have specific cellular machinery and characteristic mechanisms for post-translational activities (e.g., CHO, HeLa, MDCK, HEK293, and WI38), are available from the American Type Culture Collection (ATCC; 10801 University Boulevard, Manassas, Va. 20110-2209) and can be chosen to ensure the correct modification and processing of the foreign protein.

Stable expression is preferred for long-term, high-yield production of recombinant proteins. For example, cell lines which stably express protein kinase-like polypeptides can be transformed using expression vectors which can contain viral origins of replication and/or endogenous expression elements and a selectable marker gene on the same or on a separate vector. Following the introduction of the vector, cells can be allowed to grow for 1–2 days in an enriched medium before they are switched to a selective medium. The purpose of the selectable marker is to confer resistance to selection, and its presence allows growth and recovery of cells which successfully express the introduced protein kinase-like protein sequences. Resistant clones of stably transformed cells can be proliferated using tissue culture techniques appropriate to the cell type. See, for example, Animal Cell Culture, R. I. Freshney, ed., 1986.

Any number of selection systems can be used to recover transformed cell lines.

These include, but are not limited to, the herpes simplex virus thymidine kinase (Wigler et al., *Cell* 11, 223–32, 1977) and adenine phosphoribosyltransferase (Lowy et al., *Cell* 22, 817–23, 1980) genes which can be employed in tk⁻ or aprt⁻ cells, respectively. Also, antimetabolite, antibiotic, or herbicide resistance can be used as the basis for selection. For example, dhfr confers resistance to methotrexate (Wigler et al., Proc. Natl. Acad. Sci. 77, 3567–70, 1980), npt confers resistance to the aminoglycosides, neomycin and G-418 (Colbere-Garapin et al., *J. Mol. Biol.* 150, 1–14, 1981), and als and pat confer resistance to chlorsulfuron and phosphinotricin acetyltransferase, respectively (Murray, 1992, supra). Additional selectable genes have been described. For example, trpB allows cells to utilize indole in place of tryptophan, or hisD, which allows cells to utilize histinol in place of histidine (Hartman & Mulligan, Proc. Natl. Acad. Sci. 85, 8047–51, 1988). Visible markers such as anthocyanins, β-glucuronidase and its substrate GUS, and luciferase and its substrate luciferin, can be used to identify transformants and to quantify the amount of transient or stable protein expression attributable to a specific vector system (Rhodes et al., *Methods Mol. Biol.* 55, 121–131, 1995).

Detecting Expression

Although the presence of marker gene expression suggests that the protein kinase-like polynucleotide is also present, its presence and expression may need to be confirmed. For example, if a sequence encoding a protein kinase-like polypeptide is inserted within a marker gene sequence, transformed cells containing sequences that encode a protein kinase-like polypeptide can be identified by the absence of marker gene function. Alternatively, a marker gene can be placed in tandem with a sequence encoding a protein kinase-like polypeptide under the control of a single promoter. Expression of the marker gene in response to induction or selection usually indicates expression of the protein kinase-like polynucleotide.

Alternatively, host cells which contain a protein kinase-like polynucleotide and which express a protein kinase-like polypeptide can be identified by a variety of procedures known to those of skill in the art. These procedures include, but are not limited to, DNA-DNA or DNA-RNA hybridizations and protein bioassay or immunoassay techniques that include membrane, solution, or chip-based technologies for the detection and/or quantification of nucleic acid or protein. For example, the presence of a polynucleotide sequence encoding a protein kinase-like polypeptide can be detected by DNA-DNA or DNA-RNA hybridization or amplification using probes or fragments or fragments of polynucleotides encoding a protein kinase-like polypeptide. Nucleic acid amplification-based assays involve the use of oligonucleotides selected from sequences encoding a protein kinase-like polypeptide to detect transformants that contain a protein kinase-like polynucleotide.

A variety of protocols for detecting and measuring the expression of a protein kinase-like polypeptide, using either polyclonal or monoclonal antibodies specific for the polypeptide, are known in the art. Examples include enzyme-linked immunosorbent assay (ELISA), radioimmunoassay (RIA), and fluorescence activated cell sorting (FACS). A two-site, monoclonal-based immunoassay using monoclonal antibodies reactive to two non-interfering epitopes on a protein kinase-like polypeptide can be used, or a competitive binding assay can be employed. These and other assays are described in Hampton et al., SEROLOGICAL METHODS: A LABORATORY MANUAL, APS Press, St. Paul, Minn., 1990) and Maddox et al., *J. Exp. Med.* 158, 1211–1216, 1983).

A wide variety of labels and conjugation techniques are known by those skilled in the art and can be used in various nucleic acid and amino acid assays. Means for producing labeled hybridization or PCR probes for detecting sequences related to polynucleotides encoding protein kinase-like polypeptides include oligolabeling, nick translation, end-labeling, or PCR amplification using a labeled nucleotide. Alternatively, sequences encoding a protein kinase-like polypeptide can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Pharmacia Biotech, Promega, and US Biochemical). Suitable reporter molecules or labels which can be used for ease of detection include radionuclides, enzymes, and fluorescent, chemiluminescent, or chromogenic agents, as well as substrates, cofactors, inhibitors, magnetic particles, and the like.

Expression and Purification of Polypeptides

Host cells transformed with nucleotide sequences encoding a protein kinase-like polypeptide can be cultured under conditions suitable for the expression and recovery of the protein from cell culture. The polypeptide produced by a transformed cell can be secreted or contained intracellularly depending on the sequence and/or the vector used. As will be understood by those of skill in the art, expression vectors containing polynucleotides which encode protein kinase-like polypeptides can be designed to contain signal sequences which direct secretion of soluble protein kinase-like polypeptides through a prokaryotic or eukaryotic cell membrane or which direct the membrane insertion of membrane-bound protein kinase-like polypeptide.

As discussed above, other constructions can be used to join a sequence encoding a protein kinase-like polypeptide to a nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). Inclusion of cleavable linker sequences such as those specific for Factor Xa or enterokinase (Invitrogen, San Diego, Calif.) between the purification domain and the protein kinase-like polypeptide also can be used to facilitate purification. One such expression vector provides for expression of a fusion protein containing a protein kinase-like polypeptide and 6 histidine residues preceding a thioredoxin or an enterokinase cleavage site. The histidine residues facilitate purification by IMAC (immobilized metal ion affinity chromatography, as described in Porath et al., *Prot. Exp. Purif.* 3, 263–281, 1992), while the enterokinase cleavage site provides a means for purifying the protein kinase-like polypeptide from the fusion protein. Vectors that contain fusion proteins are disclosed in Kroll et al., *DNA Cell Biol.* 12,441–453,1993.

Chemical Synthesis

Sequences encoding a protein kinase-like polypeptide can be synthesized, in whole or in part, using chemical methods well known in the art (see Caruthers et al., *Nucl. Acids Res. Symp. Ser.* 215–223, 1980; Horn et al. *Nucl. Acids Res. Symp. Ser.* 225–232, 1980). Alternatively, a protein kinase-like polypeptide itself can be produced using chemical methods to synthesize its amino acid sequence, such as by direct peptide synthesis using solid-phase techniques (Merrifield, *J. Am. Chem. Soc.* 85, 2149–2154, 1963; Roberge et al., *Science* 269, 202–204, 1995). Protein synthesis can be performed using manual techniques or by automation. Automated synthesis can be achieved, for example, using Applied Biosystems 431A Peptide Synthesizer (Perkin Elmer). Optionally, fragments of protein kinase-like polypeptides can be separately synthesized and combined using chemical methods to produce a full-length molecule.

The newly synthesized peptide can be substantially purified by preparative high performance liquid chromatography (e.g., Creighton, PROTEINS: STRUCTURES AND MOLECULAR PRINCIPLES, WH Freeman and Co., New York, N.Y., 1983). The composition of a synthetic protein kinase-like polypeptide can be confirmed by amino acid analysis or sequencing (e.g., the Edman degradation procedure; see Creighton, supra). Additionally, any portion of the amino acid sequence of the protein kinase-like polypeptide can be altered during direct synthesis and/or combined using chemical methods with sequences from other proteins to produce a variant polypeptide or a fusion protein.

Production of Altered Polypeptides

As will be understood by those of skill in the art, it may be advantageous to produce protein kinase-like polypeptide-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life that is longer than that of a transcript generated from the naturally occurring sequence.

The nucleotide sequences disclosed herein can be engineered using methods generally known in the art to alter protein kinase-like polypeptide-encoding sequences for a variety of reasons, including but not limited to, alterations which modify the cloning, processing, and/or expression of the polypeptide or mRNA product. DNA shuffling by random fragmentation and PCR reassembly of gene fragments and synthetic oligonucleotides can be used to engineer the nucleotide sequences. For example, site-directed mutagenesis can be used to insert new restriction sites, alter glycosylation patterns, change codon preference, produce splice variants, introduce mutations, and so forth.

Antibodies

Any type of antibody known in the art can be generated to bind specifically to an epitope of a protein kinase-like polypeptide. "Antibody" as used herein includes intact immunoglobulin molecules, as well as fragments thereof, such as Fab, F(ab')$_2$, and Fv, which are capable of binding an epitope of a protein kinase-like polypeptide.

Typically, at least 6, 8, 10, or 12 contiguous amino acids are required to form an epitope. However, epitopes which involve non-contiguous amino acids may require more, e.g., at least 15, 25, or 50 amino acids.

An antibody which specifically binds to an epitope of a protein kinase-like polypeptide can be used therapeutically, as well as in immunochemical assays, such as Western blots, ELISAs, radioimmunoassays, immunohistochemical assays, immunoprecipitations, or other immunochemical assays known in the art. Various immunoassays can be used to identify antibodies having the desired specificity. Numerous protocols for competitive binding or immunoradiometric assays are well known in the art. Such immunoassays typically involve the measurement of complex formation between an immunogen and an antibody that specifically binds to the immunogen.

Typically, an antibody which specifically binds to a protein kinase-like polypeptide provides a detection signal at least 5-, 10-, or 20-fold higher than a detection signal provided with other proteins when used in an immunochemical assay. Preferably, antibodies which specifically bind to protein kinase-like polypeptides do not detect other proteins in immunochemical assays and can immunoprecipitate a protein kinase-like polypeptide from solution.

Human protein kinase-like polypeptides can be used to immunize a mammal, such as a mouse, rat, rabbit, guinea pig, monkey, or human, to produce polyclonal antibodies. If desired, a protein kinase-like polypeptide can be conjugated to a carrier protein, such as bovine serum albumin, thyroglobulin, and keyhole limpet hemocyanin. Depending on the host species, various adjuvants can be used to increase the immunological response. Such adjuvants include, but are not limited to, Freund's adjuvant, mineral gels (e.g., aluminum hydroxide), and surface active substances (e.g. lysolecithin, pluronic polyols, polyanions, peptides, oil emulsions, keyhole limpet hemocyanin, and dinitrophenol). Among adjuvants used in humans, BCG (bacilli Calmette-Guerin) and *Corynebacterium parvum* are especially useful.

Monoclonal antibodies that specifically bind to a protein kinase-like polypeptide can be prepared using any technique which provides for the production of antibody molecules by continuous cell lines in culture. These techniques include, but are not limited to, the hybridoma technique, the human B-cell hybridoma technique, and the EBV-hybridoma technique (Kohler et al., *Nature* 256, 495–497, 1985; Kozbor et al., *J. Immunol. Methods* 81, 31–42, 1985; Cote et al., *Proc. Natl. Acad. Sci.* 80, 2026–2030, 1983; Cole et al., *Mol. Cell Biol.* 62, 109–120, 1984).

In addition, techniques developed for the production of "chimeric antibodies," the splicing of mouse antibody genes to human antibody genes to obtain a molecule with appropriate antigen specificity and biological activity, can be used (Morrison et al., *Proc Natl. Acad. Sci.* 81, 6851–6855, 1984; Neuberger et al., *Nature* 312, 604–608, 1984; Takeda et al., *Nature* 314, 452–454, 1985). Monoclonal and other antibodies also can be "humanized" to prevent a patient from mounting an immune response against the antibody when it is used therapeutically. Such antibodies may be sufficiently similar in sequence to human antibodies to be used directly in therapy or may require alteration of a few key residues. Sequence differences between rodent antibodies and human sequences can be minimized by replacing residues which differ from those in the human sequences by site directed mutagenesis of individual residues or by grating of entire complementarity determining regions. Alternatively, humanized antibodies can be produced using recombinant methods, as described in GB2188638B. Antibodies that specifically bind to a protein kinase-like polypeptide can contain antigen binding sites which are either partially or fully humanized, as disclosed in U.S. Pat. No. 5,565,332.

Alternatively, techniques described for the production of single chain antibodies can be adapted using methods known in the art to produce single chain antibodies that specifically bind to protein kinase-like polypeptides. Antibodies with related specificity, but of distinct idiotypic composition, can be generated by chain shuffling from random combinatorial immunoglobin libraries (Burton, *Proc. Natl. Acad. Sci.* 88, 11120–23, 1991).

Single-chain antibodies also can be constructed using a DNA amplification method, such as PCR, using hybridoma cDNA as a template (Thirion et al., 1996, *Eur. J. Cancer Prev.* 5, 507–11). Single-chain antibodies can be mono- or bispecific, and can be bivalent or tetravalent. Construction of tetravalent, bispecific single-chain antibodies is taught, for example, in Coloma & Morrison, 1997, *Nat. Biotechnol.* 15, 159–63. Construction of bivalent, bispecific single-chain antibodies is taught in Mallender & Voss, 1994, *J. Biol. Chem.* 269, 199–206.

A nucleotide sequence encoding a single-chain antibody can be constructed using manual or automated nucleotide synthesis, cloned into an expression construct using standard recombinant DNA methods, and introduced into a cell to express the coding sequence, as described below. Alternatively, single-chain antibodies can be produced directly using, for example, filamentous phage technology (Verhaar et al., 1995, *Int. J. Cancer* 61, 497–501; Nicholls et al., 1993, *J. Immunol. Meth.* 165, 81–91).

Antibodies which specifically bind to protein kinase-like polypeptides also can be produced by inducing in vivo production in the lymphocyte population or by screening immunoglobulin libraries or panels of highly specific binding reagents as disclosed in the literature (Orlandi et al., *Proc. Natl. Acad. Sci.* 86, 3833–3837, 1989; Winter et al., *Nature* 349, 293–299, 1991).

Other types of antibodies can be constructed and used therapeutically in methods of the invention. For example, chimeric antibodies can be constructed as disclosed in WO 93/03151. Binding proteins which are derived from immunoglobulins and which are multivalent and multispecific, such as the "diabodies" described in WO 94/13804, also can be prepared.

Antibodies according to the invention can be purified by methods well known in the art. For example, antibodies can be affinity purified by passage over a column to which a protein kinase-like polypeptide is bound. The bound antibodies can then be eluted from the column using a buffer with a high salt concentration.

Antisense Oligonucleotides

Antisense oligonucleotides are nucleotide sequences that are complementary to a specific DNA or RNA sequence. Once introduced into a cell, the complementary nucleotides combine with natural sequences produced by the cell to form complexes and block either transcription or translation. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotide molecules can be provided in a DNA construct and introduced into a cell as described above to decrease the level of protein kinase-like gene products in the cell.

Antisense oligonucleotides can be deoxyribonucleotides, ribonucleotides, or a combination of both. Oligonucleotides can be synthesized manually or by an automated synthesizer, by covalently linking the 5' end of one nucleotide with the 3' end of another nucleotide with non-phosphodiester internucleotide linkages such alkyl-phosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, *Meth. Mol. Biol.* 20, 1–8, 1994; Sonveaux, *Meth. Mol. Biol.* 26, 1–72, 1994; Uhlmann et al., *Chem. Rev.* 90, 543–583,1990.

Modifications of protein kinase-like gene expression can be obtained by designing antisense oligonucleotides that will form duplexes to the control, 5', or regulatory regions of the protein kinase-like gene. Oligonucleotides derived from the transcription initiation site, e.g., between positions –10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or chaperons. Therapeutic advances using triplex DNA have been described in the literature (e.g., Gee et al., in Huber & Carr, MOLECULAR AND IMMUNOLOGIC APPROACHES, Futura Publishing Co., Mt. Kisco, N.Y., 1994). An antisense oligonucleotide also can be designed to block translation of mRNA by preventing the transcript from binding to ribosomes.

Precise complementarity is not required for successful complex formation between an antisense oligonucleotide and the complementary sequence of a protein kinase-like polynucleotide. Antisense oligonucleotides which comprise, for example, 2, 3, 4, or 5 or more stretches of contiguous nucleotides which are precisely complementary to a protein kinase-like polynucleotide, each separated by a stretch of contiguous nucleotides which are not complementary to adjacent protein kinase-like protein nucleotides, can provide sufficient targeting specificity for protein kinase-like mRNA. Preferably, each stretch of complementary contiguous nucleotides is at least 4, 5, 6, 7, or 8 or more nucleotides in length. Non-complementary intervening sequences are preferably 1, 2, 3, or 4 nucleotides in length. One skilled in the art can easily use the calculated melting point of an antisense-sense pair to determine the degree of mismatching which will be tolerated between a particular antisense oligonucleotide and a particular protein kinase-like polynucleotide sequence.

Antisense oligonucleotides can be modified without affecting their ability to hybridize to a protein kinase-like polynucleotide. These modifications can be internal or at one or both ends of the antisense molecule. For example, internucleoside phosphate linkages can be modified by adding cholesteryl or diamine moieties with varying numbers of carbon residues between the amino groups and terminal ribose. Modified bases and/or sugars, such as arabinose instead of ribose, or a 3',5'-substituted oligonucleotide in which the 3' hydroxyl group or the 5' phosphate group are substituted, also can be employed in a modified antisense oligonucleotide. These modified oligonucleotides can be prepared by methods well known in the art. See, e.g., Agrawal et al., *Trends Biotechnol.* 10, 152–158, 1992; Uhlmann et al., *Chem. Rev.* 90, 543–584, 1990; Uhlmann et al., *Tetrahedron. Lett.* 215, 3539–3542, 1987.

Ribozymes

Ribozymes are RNA molecules with catalytic activity. See, e.g., Cech, *Science* 236, 1532–1539; 1987; Cech, *Ann. Rev. Biochem.* 59, 543–568; 1990, Cech, *Curr. Opin. Struct. Biol.* 2, 605–609; 1992, Couture & Stinchcomb, *Trends Genet.* 12, 510–515, 1996. Ribozymes can be used to inhibit gene function by cleaving an RNA sequence, as is known in the art (e.g., Haseloff et al., U.S. Pat. No. 5,641,673). The mechanism of ribozyme action involves sequence-specific hybridization of the ribozyme molecule to complementary target RNA, followed by endonucleolytic cleavage. Examples include engineered hammerhead motif ribozyme molecules that can specifically and efficiently catalyze endonucleolytic cleavage of specific nucleotide sequences.

The coding sequence of a protein kinase-like polynucleotide can be used to generate ribozymes that will specifically bind to mRNA transcribed from the protein kinase-like polynucleotide. Methods of designing and constructing ribozymes which can cleave other RNA molecules in trans in a highly sequence specific manner have been developed and described in the art (see Haseloff et al. *Nature* 334, 585–591, 1988). For example, the cleavage activity of ribozymes can be targeted to specific RNAs by engineering a discrete "hybridization" region into the ribozyme. The hybridization region contains a sequence complementary to the target RNA and thus specifically hybridizes with the target (see, for example, Gerlach et al., EP 321,201).

Specific ribozyme cleavage sites within a protein kinase-like protein RNA target can be identified by scanning the target molecule for ribozyme cleavage sites which include the following sequences: GUA, GUU, and GUC. Once identified, short RNA sequences of between 15 and 20 ribonucleotides corresponding to the region of the target RNA containing the cleavage site can be evaluated for secondary structural features which may render the target inoperable. Suitability of candidate protein kinase-like protein RNA targets also can be evaluated by testing accessibility to hybridization with complementary oligonucleotides using ribonuclease protection assays. Longer complementary sequences can be used to increase the affinity of the hybridization sequence for the target. The hybridizing and cleavage regions of the ribozyme can be integrally related such that upon hybridizing to the target RNA through the complementary regions, the catalytic region of the ribozyme can cleave the target.

Ribozymes can be introduced into cells as part of a DNA construct. Mechanical methods, such as microinjection, liposome-mediated transfection, electroporation, or calcium phosphate precipitation, can be used to introduce a ribozyme-containing DNA construct into cells in which it is desired to decrease protein kinase-like protein expression. Alternatively, if it is desired that the cells stably retain the DNA construct, the construct can be supplied on a plasmid and maintained as a separate element or integrated into the genome of the cells, as is known in the art. A ribozyme-encoding DNA construct can include transcriptional regulatory elements, such as a promoter element, an enhancer or UAS element, and a transcriptional terminator signal, for controlling transcription of ribozymes in the cells.

As taught in Haseloff et al., U.S. Pat. No. 5,641,673, ribozymes can be engineered so that ribozyme expression will occur in response to factors that induce expression of a target gene. Ribozymes also can be engineered to provide an additional level of regulation, so that destruction of mRNA occurs only when both a ribozyme and a target gene are induced in the cells.

Differentially Expressed Genes

Described herein are methods for the identification of genes whose products interact with human protein kinase-like protein. Such genes may represent genes that are differentially expressed in disorders including, but not limited to, cancer, CNS disorders, COPD, obesity, diabetes, and cardiovascular disorders Further, such genes may represent genes that are differentially regulated in response to manipulations relevant to the progression or treatment of such diseases. Additionally, such genes may have a temporally modulated expression, increased or decreased at different stages of tissue or organism development. A differentially expressed gene may also have its expression modulated under control versus experimental conditions. In addition, the human protein kinase-like gene or gene product may itself be tested for differential expression.

The degree to which expression differs in a normal versus a diseased state need only be large enough to be visualized via standard characterization techniques such as differential display techniques. Other such standard characterization techniques by which expression differences may be visualized include but are not limited to, quantitative RT (reverse transcriptase), PCR, and Northern analysis.

Identification of Differentially Expressed Genes

To identify differentially expressed genes total RNA or, preferably, mRNA is isolated from tissues of interest. For example, RNA samples are obtained from tissues of experimental subjects and from corresponding tissues of control subjects. Any RNA isolation technique that does not select against the isolation of mRNA may be utilized for the purification of such RNA samples. See, for example, Ausubel et al., ed., CURRENT PROTOCOLS IN MOLECULAR BIOLOGY, John Wiley & Sons, Inc. New York, 1987–1993. Large numbers of tissue samples may readily be processed using techniques well known to those of skill in the art, such as, for example, the single-step RNA isolation process of Chomczynski, U.S. Pat. No. 4,843,155.

Transcripts within the collected RNA samples that represent RNA produced by differentially expressed genes are identified by methods well known to those of skill in the art. They include, for example, differential screening (Tedder et al., *Proc. Natl. Acad. Sci. U.S.A.* 85, 208–12, 1988), subtractive hybridization (Hedrick et al., Nature 308, 149–53; Lee et al., Proc. Natl. Acad. Sci. U.S.A. 88, 2825, 1984), and, preferably, differential display (Liang & Pardee, *Science* 257, 967–71, 1992; U.S. Pat. No. 5,262,311).

The differential expression information may itself suggest relevant methods for the treatment of disorders involving the human protein kinase-like protein. For example, treatment may include a modulation of expression of the differentially expressed genes and/or the gene encoding the human protein kinase-like protein. The differential expression information may indicate whether the expression or activity of the differentially expressed gene or gene product or the human protein kinase-like gene or gene product are up-regulated or down-regulated.

Screening Methods

The invention provides assays for screening test compounds that bind to or modulate the activity of a protein kinase-like polypeptide or a protein kinase-like polynucleotide. A test compound preferably binds to a protein kinase-like polypeptide or polynucleotide. More preferably, a test compound decreases or increases enzyme activity by at least about 10, preferably about 50, more preferably about 75, 90, or 100% relative to the absence of the test compound.

Test Compounds

Test compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, test compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. The biological library approach is limited to polypeptide libraries, while the other four approaches are applicable to polypeptide, non-peptide oligomer, or small molecule libraries of compounds. See Lam, *Anticancer Drug Des.* 12, 145, 1997.

Methods for the synthesis of molecular libraries are well known in the art (see, for example, DeWitt et al., *Proc. Natl.*

Acad. Sci. U.S.A. 90, 6909, 1993; Erb et al. Proc. Natl. Acad. Sci. U.S.A. 91, 11422, 1994; Zuckermann et al., J. Med. Chem. 37, 2678, 1994; Cho et al., Science 261, 1303, 1993; Carell et al., Angew. Chem. Int. Ed. Engl. 33, 2059, 1994; Carell et al., Angew. Chem. Int. Ed. Engl. 33, 2061; Gallop et al., J. Med. Chem. 37, 1233, 1994). Libraries of compounds can be presented in solution (see, e.g., Houghten, BioTechniques 13, 412–421, 1992), or on beads (Lam, Nature 354, 82–84, 1991), chips (Fodor, Nature 364, 555–556, 1993), bacteria or spores (Ladner, U.S. Pat. No. 5,223,409), plasmids (Cull et al., Proc. Natl. Acad. Sci. U.S.A. 89, 1865–1869, 1992), or phage (Scott & Smith, Science 249, 386–390, 1990; Devlin, Science 249, 404–406, 1990); Cwirla et al., Proc. Natl. Acad. Sci. 97, 6378–6382, 1990; Felici, J. Mol. Biol. 222, 301–310, 1991; and Ladner, U.S. Pat. No. 5,223,409).

High Throughput Screening

Test compounds can be screened for the ability to bind to protein kinase-like polypeptides or polynucleotides or to affect protein kinase-like protein activity or protein kinase-like gene expression using high throughput screening. Using high throughput screening, many discrete compounds can be tested in parallel so that large numbers of test compounds can be quickly screened. The most widely established techniques utilize 96-well microfiter plates. The wells of the microtiter plates typically require assay volumes that range from 50 to 500 µl. In addition to the plates, many instruments, materials, pipettors, robotics, plate washers, and plate readers are commercially available to fit the 96-well format.

Alternatively, "free format assays," or assays that have no physical barrier between samples, can be used. For example, an assay using pigment cells (melanocytes) in a simple homogeneous assay for combinatorial peptide libraries is described by Jayawickreme et al., Proc. Natl. Acad. Sci. U.S.A. 19, 1614–18 (1994). The cells are placed under agarose in petri dishes, then beads that carry combinatorial compounds are placed on the surface of the agarose. The combinatorial compounds are partially released the compounds from the beads. Active compounds can be visualized as dark pigment areas because, as the compounds diffuse locally into the gel matrix, the active compounds cause the cells to change colors.

Another example of a free format assay is described by Chelsky, "Strategies for Screening Combinatorial Libraries: Novel and Traditional Approaches," reported at the First Annual Conference of The Society for Biomolecular Screening in Philadelphia, Pa. (Nov. 7–10, 1995). Chelsky placed a simple homogenous enzyme assay for carbonic anhydrase inside an agarose gel such that the enzyme in the gel would cause a color change throughout the gel. Thereafter, beads carrying combinatorial compounds via a photolinker were placed inside the gel and the compounds were partially released by UV-light. Compounds that inhibited the enzyme were observed as local zones of inhibition having less color change.

Yet another example is described by Salmon et al., Molecular Diversity 2, 57–63 (1996). In this example, combinatorial libraries were screened for compounds that had cytotoxic effects on cancer cells growing in agar.

Another high throughput screening method is described in Beutel et al., U.S. Pat. No. 5,976,813. In this method, test samples are placed in a porous matrix. One or more assay components are then placed within, on top of, or at the bottom of a matrix such as a gel, a plastic sheet, a filter, or other form of easily manipulated solid support. When samples are introduced to the porous matrix they diffuse sufficiently slowly, such that the assays can be performed without the test samples running together.

Binding Assays

For binding assays, the test compound is preferably a small molecule that binds to and occupies, for example, the active site of the protein kinase-like polypeptide, such that normal biological activity is prevented. Examples of such small molecules include, but are not limited to, small peptides or peptide-like molecules.

In binding assays, either the test compound or the protein kinase-like polypeptide can comprise a detectable label, such as a fluorescent, radioisotopic, chemiluminescent, or enzymatic label, such as horseradish peroxidase, alkaline phosphatase, or luciferase. Detection of a test compound that is bound to the protein kinase-like polypeptide can then be accomplished, for example, by direct counting of radio-emmission, by scintillation counting, or by determining conversion of an appropriate substrate to a detectable product.

Alternatively, binding of a test compound to a protein kinase-like polypeptide can be determined without labeling either of the interactants. For example, a microphysiometer can be used to detect binding of a test compound with a protein kinase-like polypeptide. A microphysiometer (e.g., Cytosensor™) is an analytical instrument that measures the rate at which a cell acidifies its environment using a light-addressable potentiometric sensor (LAPS). Changes in this acidification rate can be used as an indicator of the interaction between a test compound and a protein kinase-like polypeptide (McConnell et al., Science 257, 1906–1912, 1992).

Determining the ability of a test compound to bind to a protein kinase-like polypeptide also can be accomplished using a technology such as real-time Bimolecular Interaction Analysis (BIA) (Sjolander & Urbaniczky, Anal. Chem. 63, 2338–2345, 1991, and Szabo et al., Curr. Opin. Struct. Biol. 5, 699–705, 1995). BIA is a technology for studying bio-specific interactions in real time, without labeling any of the interactants (e.g., BIAcore™). Changes in the optical phenomenon surface plasmon resonance (SPR) can be used as an indication of real-time reactions between biological molecules.

In yet another aspect of the invention, a protein kinase-like polypeptide can be used as a "bait protein" in a two-hybrid assay or three-hybrid assay (see, e.g., U.S. Pat. No. 5,283,317; Zervos et al., Cell 72, 223–232, 1993; Madura et al., J. Biol. Chem. 268, 12046–12054, 1993; Bartel et al., BioTechniques 14, 920–924, 1993; Iwabuchi et al., Oncogene 8, 1693–1696, 1993; and Brent WO94/10300), to identify other proteins which bind to or interact with the protein kinase-like polypeptide and modulate its activity.

The two-hybrid system is based on the modular nature of most transcription factors, which consist of separable DNA-binding and activation domains. Briefly, the assay utilizes two different DNA constructs. For example, in one construct, polynucleotide encoding a protein kinase-like polypeptide can be fused to a polynucleotide encoding the DNA binding domain of a known transcription factor (e.g., GAL-4). In the other construct a DNA sequence that encodes an unidentified protein ("prey" or "sample") can be fused to a polynucleotide that codes for the activation domain of the known transcription factor. If the "bait" and the "prey" proteins are able to interact in vivo to form an protein-dependent complex, the DNA-binding and activation domains of the transcription factor are brought into close proximity. This proximity allows transcription of a reporter gene (e.g., LacZ), which is operably linked to a transcriptional regulatory site responsive to the transcription factor. Expression of the reporter gene can be detected, and cell colonies containing the functional transcription factor can be isolated and used to obtain the DNA sequence encoding the protein that interacts with the protein kinase-like polypeptide.

It may be desirable to immobilize either the protein kinase-like polypeptide (or polynucleotide) or the test compound to facilitate separation of bound from unbound forms of one or both of the interactants, as well as to accommodate automation of the assay. Thus, either the protein kinase-like polypeptide (or polynucleotide) or the test compound can be bound to a solid support. Suitable solid supports include, but are not limited to, glass or plastic slides, tissue culture plates, microtiter wells, tubes, silicon chips, or particles such as beads (including, but not limited to, latex, polystyrene, or glass beads). Any method known in the art can be used to attach the enzyme polypeptide (or polynucleotide) or test compound to a solid support, including use of covalent and non-covalent linkages, passive absorption, or pairs of binding moieties attached respectively to the polypeptide (or polynucleotide) or test compound and the solid support. Test compounds are preferably bound to the solid support in an array, so that the location of individual test compounds can be tracked. Binding of a test compound to a protein kinase-like polypeptide (or polynucleotide) can be accomplished in any vessel suitable for containing the reactants. Examples of such vessels include microtiter plates, test tubes, and microcentrifuge tubes.

In one embodiment, the protein kinase-like polypeptide is a fusion protein comprising a domain that allows the protein kinase-like polypeptide to be bound to a solid support. For example, glutathione-S-transferase fusion proteins can be adsorbed onto glutathione sepharose beads (Sigma Chemical, St. Louis, Mo.) or glutathione derivatized microtiter plates, which are then combined with the test compound or the test compound and the non-adsorbed protein kinase-like polypeptide; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing proteins or polynucleotides on a solid support also can be used in the screening assays of the invention. For example, either a protein kinase-like polypeptide (or polynucleotide) or a test compound can be immobilized utilizing conjugation of biotin and streptavidin. Biotinylated protein kinase-like polypeptides (or polynucleotides) or test compounds can be prepared from biotin-NHS(N-hydroxysuccinimide) using techniques well known in the art (e.g., biotinylation kit, Pierce Chemicals, Rockford, Ill.) and immobilized in the wells of streptavidin-coated 96 well plates (Pierce Chemical). Alternatively, antibodies which specifically bind to a protein kinase-like polypeptide, polynucleotide, or a test compound, but which do not interfere with a desired binding site, such as the active site of the protein kinase-like polypeptide, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to the protein kinase-like polypeptide or test compound, enzyme-linked assays which rely on detecting an activity of the protein kinase-like polypeptide, and SDS gel electrophoresis under non-reducing conditions.

Screening for test compounds which bind to a protein kinase-like polypeptide or polynucleotide also can be carried out in an intact cell. Any cell which comprises a protein kinase-like polypeptide or polynucleotide can be used in a cell-based assay system. A protein kinase-like polynucleotide can be naturally occurring in the cell or can be introduced using techniques such as those described above. Binding of the test compound to a protein kinase-like polypeptide or polynucleotide is determined as described above.

Enzyme Assays

Test compounds can be tested for the ability to increase or decrease the protein kinase activity of a human protein kinase-like polypeptide. Protein kinase activity can be measured, for example, as described in U.S. Pat. No. 6,194,186

Enzyme assays can be carried out after contacting either a purified protein kinase-like polypeptide, a cell membrane preparation, or an intact cell with a test compound. A test compound that decreases a protein kinase activity of a protein kinase-like polypeptide by at least about 10, preferably about 50, more preferably about 75, 90, or 100% is identified as a potential therapeutic agent for decreasing protein kinase-like protein activity. A test compound which increases a protein kinase activity of a human protein kinase-like polypeptide by at least about 10, preferably about 50, more preferably about 75, 90, or 100% is identified as a potential therapeutic agent for increasing human protein kinase-like protein activity.

Gene Expression

In another embodiment, test compounds that increase or decrease protein kinase-like gene expression are identified. A protein kinase-like polynucleotide is contacted with a test compound, and the expression of an RNA or polypeptide product of the protein kinase-like polynucleotide is determined. The level of expression of appropriate mRNA or polypeptide in the presence of the test compound is compared to the level of expression of mRNA or polypeptide in the absence of the test compound. The test compound can then be identified as a modulator of expression based on this comparison. For example, when expression of mRNA or polypeptide is greater in the presence of the test compound than in its absence, the test compound is identified as a stimulator or enhancer of the mRNA or polypeptide expression. Alternatively, when expression of the mRNA or polypeptide is less in the presence of the test compound than in its absence, the test compound is identified as an inhibitor of the mRNA or polypeptide expression.

The level of protein kinase-like mRNA or polypeptide expression in the cells can be determined by methods well known in the art for detecting mRNA or polypeptide. Either qualitative or quantitative methods can be used. The presence of polypeptide products of a protein kinase-like polynucleotide can be determined, for example, using a variety of techniques known in the art, including immunochemical methods such as radioimmunoassay, Western blotting, and immunohistochemistry. Alternatively, polypeptide synthesis can be determined in vivo, in a cell culture, or in an in vitro translation system by detecting incorporation of labeled amino acids into a protein kinase-like polypeptide.

Such screening can be carried out either in a cell-free assay system or in an intact cell. Any cell that expresses a protein kinase-like polynucleotide can be used in a cell-based assay system. The protein kinase-like polynucleotide can be naturally occurring in the cell or can be introduced using techniques such as those described above. Either a primary culture or an established cell line, such as CHO or human embryonic kidney 293 cells, can be used.

Pharmaceutical Compositions

The invention also provides pharmaceutical compositions that can be administered to a patient to achieve a therapeutic effect. Pharmaceutical compositions of the invention can comprise, for example, a protein kinase-like polypeptide, protein kinase-like polynucleotide, ribozymes or antisense oligonucleotides, antibodies which specifically bind to a protein kinase-like polypeptide, or mimetics, activators, or inhibitors of a protein kinase-like polypeptide activity. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically-acceptable carriers comprising excipients and auxiliaries that facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof, such as sodium alginate.

Dragee cores can be used in conjunction with suitable coatings, such as concentrated sugar solutions, which also can contain gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings for product identification or to characterize the quantity of active compound, i.e., dosage.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also can contain suitable stabilizers or agents that increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee-making, levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation can be a lyophilized powder which can contain any or all of the following: 1–50 mM histidine, 0.1%–2% sucrose, and 2–7% mannitol, at a pH range of 4.5 to 5.5, that is combined with buffer prior to use.

Further details on techniques for formulation and administration can be found in the latest edition of REMINGTON'S PHARMACEUTICAL SCENCES (Maack Publishing Co., Easton, Pa.). After pharmaceutical compositions have been prepared, they can be placed in an appropriate container and labeled for treatment of an indicated condition. Such labeling would include amount, frequency, and method of administration.

Therapeutic Indications and Methods

Human protein kinase-like protein can be regulated to treat cancer, CNS disorders, COPD, obesity, diabetes, and cardiovascular disorders.

Cancer

Cancer is a disease fundamentally caused by oncogenic cellular transformation. There are several hallmarks of transformed cells that distinguish them from their normal counterparts and underlie the pathophysiology of cancer. These include uncontrolled cellular proliferation, unresponsiveness to normal death-inducing signals (immortalization), increased cellular motility and invasiveness, increased ability to recruit blood supply through induction of new blood vessel formation (angiogenesis), genetic instability, and dysregulated gene expression. Various combinations of these aberrant physiologies, along with the acquisition of drug-resistance frequently lead to an intractable disease state in which organ failure and patient death ultimately ensue.

Most standard cancer therapies target cellular proliferation and rely on the differential proliferative capacities between transformed and normal cells for their efficacy. This approach is hindered by the facts that several important normal cell types are also highly proliferative and that cancer cells frequently become resistant to these agents. Thus, the therapeutic indices for traditional anti-cancer therapies rarely exceed 2.0.

The advent of genomics-driven molecular target identification has opened up the possibility of identifying new cancer-specific targets for therapeutic intervention that will provide safer, more effective treatments for cancer patients. Thus, newly discovered tumor-associated genes and their products can be tested for their role(s) in disease and used as tools to discover and develop innovative therapies. Genes playing important roles in any of the physiological processes outlined above can be characterized as cancer targets.

Genes or gene fragments identified through genomics can readily be expressed in one or more heterologous expression systems to produce functional recombinant proteins. These proteins are characterized in vitro for their biochemical properties and then used as tools in high-throughput molecular screening programs to identify chemical modulators of their biochemical activities. Activators and/or inhibitors of target protein activity can be identified in this manner and subsequently tested in cellular and in vivo disease models for anti-cancer activity. Optimization of lead compounds with iterative testing in biological models and detailed pharmacokinetic and toxicological analyses form the basis for drug development and subsequent testing in humans.

Protein phosphorylation is an essential component in intracellular signaling, with diverse and crucial functions including mediation of cell proliferation, survival, apoptosis, differentiation, migration and attachment. It is regulated by the balance between the opposing activities of protein kinases and protein phosphatases. Protein phosphorylation is mainly mediated by two types of protein kinases—protein tyrosine kinases and protein serine/threonine kinases. A number of protein tyrosine kinases are encoded by proto-oncogenes or viral oncogenes, and are thus strongly implicated in cancer. Protein serine/threonine kinases are known to play a role in intracellular signal transduction mediated by growth factors, cytokines, etc. inducing either cell proliferation, apoptosis or differentiation. Inhibitors of protein kinases are expected to provide efficacious therapeutic agents for the treatment of cancer.

CNS Disorders

Central and peripheral nervous system disorders also can be treated, such as primary and secondary disorders after brain injury, disorders of mood, anxiety disorders, disorders of thought and volition, disorders of sleep and wakefulness, diseases of the motor unit, such as neurogenic and myopathic disorders, neurodegenerative disorders such as Alzheimer's and Parkinson's disease, and processes of peripheral and chronic pain.

Pain that is associated with CNS disorders also can be treated by regulating the activity of human protein kinase-like protein. Pain which can be treated includes that associated with central nervous system disorders, such as multiple sclerosis, spinal cord injury, sciatica, failed back surgery syndrome, traumatic brain injury, epilepsy, Parkinson's disease, post-stroke, and vascular lesions in the brain and spinal cord (e.g., infarct, hemorrhage, vascular malformation). Non-central neuropathic pain includes that associated with post mastectomy pain, reflex sympathetic dystrophy (RSD), trigeminal neuralgiaradioculopathy, post-surgical pain, HIV/AIDS related pain, cancer pain, metabolic neuropathies (e.g., diabetic neuropathy, vasculitic neuropathy secondary to connective tissue disease), paraneoplastic polyneuropathy associated, for example, with carcinoma of lung, or leukemia, or lymphoma, or carcinoma of prostate, colon or stomach, trigeminal neuralgia, cranial neuralgias, and post-herpetic neuralgia. Pain associated with cancer and cancer treatment also can be treated, as can headache pain (for example, migraine with aura, migraine without aura, and other migraine disorders), episodic and chronic tension-type headache, tension-type like headache, cluster headache, and chronic paroxysmal hemicrania.

COPD

Chronic obstructive pulmonary (or airways) disease (COPD) is a condition defined physiologically as airflow obstruction that generally results from a mixture of emphysema and peripheral airway obstruction due to chronic bronchitis (Senior & Shapiro, *Pulmonary Diseases and Disorders,* 3d ed., New York, McGraw-Hill, 1998, pp. 659–681, 1998; Barnes, *Chest* 117, 10S–14S, 2000). Emphysema is characterized by destruction of alveolar walls leading to abnormal enlargement of the air spaces of the lung. Chronic bronchitis is defined clinically as the presence of chronic productive cough for three months in each of two successive years. In COPD, airflow obstruction is usually progressive and is only partially reversible. By far the most important risk factor for development of COPD is cigarette smoking, although the disease does occur in non-smokers.

Chronic inflammation of the airways is a key pathological feature of COPD (Senior & Shapiro, 1998). The inflammatory cell population comprises increased numbers of macrophages, neutrophils, and $CD8^+$ lymphocytes. Inhaled irritants, such as cigarette smoke, activate macrophages which are resident in the respiratory tract, as well as epithelial cells leading to release of chemokines (e.g., interleukin-8) and other chemotactic factors. These chemotactic factors act to increase the neutrophil/-monocyte trafficking from the blood into the lung tissue and airways. Neutrophils and monocytes recruited into the airways can release a variety of potentially damaging mediators such as proteolytic enzymes and reactive oxygen species. Matrix degradation and emphysema, along with airway wall thickening, surfactant dysfunction, and mucus hypersecretion, all are potential sequelae of this inflammatory response that lead to impaired airflow and gas exchange.

Obesity and overweight are defined as an excess of body fat relative to lean body mass. An increase in caloric intake or a decrease in energy expenditure or both can bring about this imbalance leading to surplus energy being stored as fat. Obesity is associated with important medical morbidities and an increase in mortality. The causes of obesity are poorly understood and may be due to genetic factors, environmental factors or a combination of the two to cause a positive energy balance. In contrast, anorexia and cachexia are characterized by an imbalance in energy intake versus energy expenditure leading to a negative energy balance and weight loss. Agents that either increase energy expenditure and/or decrease energy intake, absorption or storage would be useful for treating obesity, overweight, and associated comorbidities. Agents that either increase energy intake and/or decrease energy expenditure or increase the amount of lean tissue would be useful for treating cachexia, anorexia and wasting disorders.

This gene, translated proteins and agents which modulate this gene or portions of the gene or its products are useful for treating obesity, overweight, anorexia, cachexia, wasting disorders, appetite suppression, appetite enhancement, increases or decreases in satiety, modulation of body weight, and/or other eating disorders such as bulimia. Also this gene, translated proteins and agents which modulate this gene or portions of the gene or its products are useful for treating obesity/overweight-associated comorbidities including hypertension, type 2 diabetes, coronary artery disease, hyperlipidemia, stroke, gallbladder disease, gout, osteoarthritis, sleep apnea and respiratory problems, some types of cancer including endometrial, breast, prostate, and colon cancer, thrombolic disease, polycystic ovarian syndrome, reduced fertility, complications of pregnancy, menstrual irregularities, hirsutism, stress incontinence, and depression.

Diabetes

Diabetes mellitus is a common metabolic disorder characterized by an abnormal elevation in blood glucose, alterations in lipids and abnormalities (complications) in the cardiovascular system, eye, kidney and nervous system. Diabetes is divided into two separate diseases: type 1 diabetes (juvenile onset), which results from a loss of cells which make and secrete insulin, and type 2 diabetes (adult onset), which is caused by a defect in insulin secretion and a defect in insulin action.

Type 1 diabetes is initiated by an autoimmune reaction that attacks the insulin secreting cells (beta cells) in the pancreatic islets. Agents that prevent this reaction from occurring or that stop the reaction before destruction of the beta cells has been accomplished are potential therapies for this disease. Other agents that induce beta cell proliferation and regeneration also are potential therapies.

Type II diabetes is the most common of the two diabetic conditions (6% of the population). The defect in insulin secretion is an important cause of the diabetic condition and results from an inability of the beta cell to properly detect and respond to rises in blood glucose levels with insulin release. Therapies that increase the response by the beta cell to glucose would offer an important new treatment for this disease.

The defect in insulin action in Type II diabetic subjects is another target for therapeutic intervention. Agents that increase the activity of the insulin receptor in muscle, liver, and fat will cause a decrease in blood glucose and a normalization of plasma lipids. The receptor activity can be increased by agents that directly stimulate the receptor or that increase the intracellular signals from the receptor. Other therapies can directly activate the cellular end process, i.e. glucose transport or various enzyme systems, to generate an insulin-like effect and therefore a produce beneficial outcome. Because overweight subjects have a greater susceptibility to Type II diabetes, any agent that reduces body weight is a possible therapy.

Both Type I and Type diabetes can be treated with agents that mimic insulin action or that treat diabetic complications by reducing blood glucose levels. Likewise, agents that reduces new blood vessel growth can be used to treat the eye complications that develop in both diseases.

Cardiovascular Diseases

Cardiovascular diseases include the following disorders of the heart and the vascular system: congestive heart failure, myocardial infarction, ischemic diseases of the heart, all kinds of atrial and ventricular arrhythmias, hypertensive vascular diseases, and peripheral vascular diseases.

Heart failure is defined as a pathophysiologic state in which an abnormality of cardiac function is responsible for the failure of the heart to pump blood at a rate commensurate with the requirement of the metabolizing tissue. It includes all forms of pumping failure, such as high-output and low-output, acute and chronic, right-sided or left-sided, systolic or diastolic, independent of the underlying cause.

Myocardial infarction (MI) is generally caused by an abrupt decrease in coronary blood flow that follows a thrombotic occlusion of a coronary artery previously narrowed by arteriosclerosis. MI prophylaxis (primary and secondary prevention) is included, as well as the acute treatment of MI and the prevention of complications.

Ischemic diseases are conditions in which the coronary flow is restricted resulting in a perfusion which is inadequate to meet the myocardial requirement for oxygen. This group of diseases includes stable angina, unstable angina, and asymptomatic ischemia.

Arrhythmias include all forms of atrial and ventricular tachyarrhythmias (atrial tachycardia, atrial flutter, atrial fibrillation, atrio-ventricular reentrant tachycardia, preexcitation syndrome, ventricular tachycardia, ventricular flutter, and ventricular fibrillation), as well as bradycardic forms of arrhythmias.

Vascular diseases include primary as well as all kinds of secondary arterial hypertension (renal, endocrine, neurogenic, others). The disclosed gene and its product may be used as drug targets for the treatment of hypertension as well as for the prevention of all complications. Peripheral vascular diseases are defined as vascular diseases in which arterial and/or venous flow is reduced resulting in an imbalance between blood supply and tissue oxygen demand. It includes chronic peripheral arterial occlusive disease (PAOD), acute arterial thrombosis and embolism, inflammatory vascular disorders, Raynaud's phenomenon, and venous disorders.

This invention further pertains to the use of novel agents identified by the screening assays described above. Accordingly, it is within the scope of this invention to use a test compound identified as described herein in an appropriate animal model. For example, an agent identified as described herein (e.g., a modulating agent, an antisense nucleic acid molecule, a specific antibody, ribozyme, or a protein kinase-like polypeptide binding molecule) can be used in an animal model to determine the efficacy, toxicity, or side effects of treatment with such an agent. Alternatively, an agent identified as described herein can be used in an animal model to determine the mechanism of action of such an agent. Furthermore, this invention pertains to uses of novel agents identified by the above-described screening assays for treatments as described herein.

A reagent which affects protein kinase-like protein activity can be administered to a human cell, either in vitro or in vivo, to reduce protein kinase-like protein activity. The reagent preferably binds to an expression product of a human protein kinase-like gene. If the expression product is a protein, the reagent is preferably an antibody. For treatment of human cells ex vivo, an antibody can be added to a preparation of stem cells that have been removed from the body. The cells can then be replaced in the same or another human body, with or without clonal propagation, as is known in the art.

In one embodiment, the reagent is delivered using a liposome. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human. Preferably, the lipid composition of the liposome is capable of targeting to a specific organ of an animal, such as the lung, liver, spleen, heart brain, lymph nodes, and skin.

A liposome useful in the present invention comprises a lipid composition that is capable of fusing with the plasma membrane of the targeted cell to deliver its contents to the cell. Preferably, the transfection efficiency of a liposome is about 0.5 µg of DNA per 16 nmole of liposome delivered to about $10^6$ cells, more preferably about 1.0 µg of DNA per 16 nmole of liposome delivered to about $10^6$ cells, and even more preferably about 2.0 µg of DNA per 16 nmol of liposome delivered to about $10^6$ cells. Preferably, a liposome is between about 100 and 500 nm, more preferably between about 150 and 450 nm, and even more preferably between about 200 and 400 nm in diameter.

Suitable liposomes for use in the present invention include those liposomes standardly used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a particular cell type, such as a cell-specific ligand exposed on the outer surface of the liposome.

Complexing a liposome with a reagent such as an antisense oligonucleotide or ribozyme can be achieved using methods that are standard in the art (see, for example, U.S. Pat. No. 5,705,151). Preferably, from about 0.1 µg to about 10 µg of polynucleotide is combined with about 8 nmol of liposomes, more preferably from about 0.5 µg to about 5 µg of polynucleotides are combined with about 8 nmol liposomes, and even more preferably about 1.0 µg of polynucleotides is combined with about 8 mol liposomes.

In another embodiment, antibodies can be delivered to specific tissues in vivo using receptor-mediated targeted delivery. Receptor-mediated DNA delivery techniques are taught in, for example, Findeis et al. Trends in Biotechnol. 11, 202–05 (1993); Chiou et al., GENE THERAPEUTICS: METHODS AND APPLICATIONS OF DIRECT GENE TRANSFER (J. A. Wolff, ed.) (1994); Wu & Wu, *J. Biol. Chem.* 263, 621–24 (1988); Wu et al., *J. Biol. Chem.* 269, 542–46 (1994); Zenke et al., *Proc. Natl. Acad. Sci. U.S.A.* 87, 3655–59 (1990); Wu et al., *J. Biol. Chem.* 266, 338–42 (1991).

Determination of a Therapeutically Effective Dose

The determination of a therapeutically effective dose is well within the capability of those skilled in the art. A therapeutically effective dose refers to that amount of active ingredient which increases or decreases protein kinase-like protein activity relative to the protein kinase-like protein activity which occurs in the absence of the therapeutically effective dose.

For any compound, the therapeutically effective dose can be estimated initially either in cell culture assays or in animal models, usually mice, rabbits, dogs, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions that exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active ingredient or to maintain the desired effect. Factors that can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

If the reagent is a single-chain antibody, polynucleotides encoding the antibody can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Effective in vivo dosages of an antibody are in the range of about 5 µg to about 50 µg/kg, about 50 µg to about 5 mg/kg, about 100 µg to about 500 µg/kg of patient body weight, and about 200 to about 250 µg/kg of patient body weight. For administration of polynucleotides encoding single-chain antibodies, effective in vivo dosages are in the range of about 100 ng to about 200 ng, 500 ng to about 50 mg, about 1 µg to about 2 mg, about 5 µg to about 500 µg, and about 20 µg to about 100 µg of DNA.

If the expression product is mRNA, the reagent is preferably an antisense oligo-nucleotide or a ribozyme. Polynucleotides that express antisense oligonucleotides or ribozymes can be introduced into cells by a variety of methods, as described above.

Preferably, a reagent reduces expression of a protein kinase-like gene or the activity of a protein kinase-like polypeptide by at least about 10, preferably about 50, more preferably about 75, 90, or 100% relative to the absence of the reagent. The effectiveness of the mechanism chosen to decrease the level of expression of a protein kinase-like gene or the activity of a protein kinase-like polypeptide can be assessed using methods well known in the art, such as hybridization of nucleotide probes to protein kinase-like protein-specific mRNA, quantitative RT-PCR, immunologic detection of a protein kinase-like polypeptide, or measurement of protein kinase-like protein activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects.

Any of the therapeutic methods described above can be applied to any subject in need of such therapy, including, for example, mammals such as dogs, cats, cows, horses, rabbits, monkeys, and most preferably, humans.

Diagnostic Methods

Human protein kinase-like protein also can be used in diagnostic assays for detecting diseases and abnormalities or susceptibility to diseases and abnormalities related to the presence of mutations in the nucleic acid sequences that encode the enzyme. For example, differences can be determined between the cDNA or genomic sequence encoding protein kinase-like protein in individuals afflicted with a disease and in normal individuals. If a mutation is observed in some or all of the afflicted individuals but not in normal individuals, then the mutation is likely to be the causative agent of the disease.

Sequence differences between a reference gene and a gene having mutations can be revealed by the direct DNA sequencing method. In addition, cloned DNA segments can be employed as probes to detect specific DNA segments. The sensitivity of this method is greatly enhanced when combined with PCR. For example, a sequencing primer can be used with a double-stranded PCR product or a single-stranded template molecule generated by a modified PCR. The sequence determination is performed by conventional procedures using radiolabeled nucleotides or by automatic sequencing procedures using fluorescent tags.

Genetic testing based on DNA sequence differences can be carried out by detection of alteration in electrophoretic mobility of DNA fragments in gels with or without denaturing agents. Small sequence deletions and insertions can be visualized, for example, by high resolution gel electrophoresis. DNA fragments of different sequences can be distinguished on denaturing formamide gradient gels in which the mobilities of different DNA fragments are retarded in the gel at different positions according to their specific melting or partial melting temperatures (see, e.g., Myers et al., *Science* 230, 1242, 1985). Sequence changes at specific locations can also be revealed by nuclease protection assays, such as RNase and S1 protection or the chemical cleavage method (e.g., Cotton et al., *Proc. Natl. Acad. Sci. USA* 85, 4397–4401, 1985). Thus, the detection of a specific DNA sequence can be performed by methods such as hybridization, RNase protection, chemical cleavage, direct DNA sequencing or the use of restriction enzymes and Southern blotting of genomic DNA. In addition to direct methods such as gel-electrophoresis and DNA sequencing, mutations can also be detected by in situ analysis.

Altered levels of protein kinase-like protein also can be detected in various tissues. Assays used to detect levels of the receptor polypeptides in a body sample, such as blood or a tissue biopsy, derived from a host are well known to those of skill in the art and include radioimmunoassays, competitive binding assays, Western blot analysis, and ELISA assays.

All patents, patent applications, and references cited in this disclosure are expressly incorporated herein by reference in their entireties. The above disclosure generally describes the present invention. A more complete understanding can be obtained by reference to the following specific examples, which are provided for purposes of illustration only and are not intended to limit the scope of the invention.

EXAMPLE 1

Detection of Proteine Kinase-like Protein Activity

The polynucleotide of SEQ ID NO: 1 is inserted into the expression vector pCEV4 and the expression vector pCEV4-proteine kinase-like protein polypeptide obtained is transfected into human embryonic kidney 293 cells. From these cells extracts are obtained and proteine kinase-like protein activity is assayed by measuring the incorporation of 32Pi into calf thymus H1 histone from [gamma-32P]ATP. Cell extracts are incubated in a reaction mixture containing 20 mM Tris HCl at pH 7.5, 10 mM MgCl2, 20 µM ATP, 15–50 kBq of [gamma-32P]ATP, and 200 µg/ml H1 istone. The incubation is carried out for 5 min at 30° C., and the phosphorylated proteins are seperated by SDS/PAGE and visualized and quanitated by measuring the intensity of photostimulated luminescene (PSL) using a Bio-Imaging Analyzer. It is shown that the polypeptide of SEQ ID NO: 2 has a proteine kinase-like protein activity.

EXAMPLE 2

Expression of Recombinant Human Protein Kinase-like Protein

The *Pichia pastoris* expression vector pPICZB (Invitrogen, San Diego, Calif.) is used to produce large quantities of recombinant human protein kinase-like polypeptides in yeast. The protein kinase-like protein-encoding DNA sequence is derived from SEQ ID NOS: 1, 8 and 10. Before insertion into vector pPICZB, the DNA sequence is modified by well known methods in such a way that it contains at its 5'-end an initiation codon and at its 3'-end an enterokinase cleavage site, a His6 reporter tag and a termination codon. Moreover, at both termini recognition sequences for restriction endonucleases are added and after digestion of the multiple cloning site of pPICZ B with the corresponding restriction enzymes the modified DNA sequence is ligated into pPICZB. This expression vector is designed for inducible expression in *Pichia pastoris*, driven by a yeast promoter. The resulting pPICZ/md-His6 vector is used to transform the yeast.

The yeast is cultivated under usual conditions in 5 liter shake flasks and the recombinantly produced protein isolated from the culture by affinity chromatography (Ni-NTA-Resin) in the presence of 8 M urea. The bound polypeptide is eluted with buffer, pH 3.5, and neutralized. Separation of the polypeptide from the His6 reporter tag is accomplished by site-specific proteolysis using enterokinase (Invitrogen, San Diego, Calif.) according to manufacturer's instructions. Purified human protein kinase-like polypeptide is obtained.

EXAMPLE 3

Identification of Test Compounds that Bind to Protein Kinase-like Polypeptides

Purified protein kinase-like polypeptides comprising a glutathione-S-transferase protein and absorbed onto glutathione-derivatized wells of 96-well microtiter plates are contacted with test compounds from a small molecule library at pH 7.0 in a physiological buffer solution. Human protein kinase-like polypeptides comprise the amino acid sequence shown in SEQ ID NOS:2 and 9. The test compounds comprise a fluorescent tag. The samples are incubated for 5 minutes to one hour. Control samples are incubated in the absence of a test compound.

The buffer solution containing the test compounds is washed from the wells. Binding of a test compound to a protein kinase-like polypeptide is detected by fluorescence measurements of the contents of the wells. A test compound that increases the fluorescence in a well by at least 15% relative to fluorescence of a well in which a test compound is not incubated is identified as a compound which binds to a protein kinase-like polypeptide.

EXAMPLE 4

Identification of a Test Compound which Decreases Protein Kinase-like Gene Expression A test compound is administered to a culture of human cells transfected with a protein kinase-like protein expression construct and incubated at 37° C. for 10 to 45 minutes. A culture of the same type of cells that have not been transfected is incubated for the same time without the test compound to provide a negative control.

RNA is isolated from the two cultures as described in Chirgwin et al., *Biochem.* 18, 5294–99, 1979). Northern blots are prepared using 20 to 30 μg total RNA and hybridized with a $^{32}$P-labeled protein kinase-like protein-specific probe at 65° C. in Express-hyb (CLONTECH). The probe comprises at least 11 contiguous nucleotides selected from the complement of SEQ ID NOS: 1, 8 and 10. A test compound that decreases the protein kinase-like protein-specific signal relative to the signal obtained in the absence of the test compound is identified as an inhibitor of protein kinase-like gene expression.

EXAMPLE 5

Identification of a Test Compound which Decreases Protein Kinase-like Protein Activity A test compound is administered to a culture of human cells transfected with a protein kinase-like protein expression construct and incubated at 37° C. for 10 to 45 minutes. A culture of the same type of cells that have not been transfected is incubated for the same time without the test compound to provide a negative control. protein kinase-like protein activity is measured using the method of U.S. Pat. No. 6,194,186.

A test compound which decreases the protein kinase-like protein activity of the protein kinase-like protein relative to the protein kinase-like protein activity in the absence of the test compound is identified as an inhibitor of protein kinase-like protein activity.

EXAMPLE 6

Tissue-Specific Expression of Protein Kinase-like Protein

The qualitative expression pattern of protein kinase-like protein in various tissues is determined by Reverse Transcription-Polymerase Chain Reaction (RT-PCR).

To demonstrate that protein kinase-like protein is involved in cancer, expression is determined in the following tissues: adrenal gland, bone marrow, brain, cerebellum, colon, fetal brain, fetal liver, heart, kidney, liver, lung, mammary gland, pancreas, placenta, prostate, salivary gland, skeletal muscle, small intestine, spinal cord, spleen, stomach, testis, thymus, thyroid, trachea, uterus, and peripheral blood lymphocytes. Expression in the following cancer cell lines also is determined: DU-145 (prostate), NCI-H125 (lung), HT-29 (colon), COLO-205 (colon), A-549 (lung), NCI—H460 (lung), HT-116 (colon), DLD-1 (colon), MDA-MD-231 (breast), LS 174T (colon), ZF-75 (breast), MDA-MN-435 (breast), HT-1080, MCF-7 (breast), and U87. Matched pairs of malignant and normal tissue from the same patient also are tested.

To demonstrate that protein kinase-like protein is involved in CNS disorders, the following tissues are screened: fetal and adult brain, muscle, heart, lung, kidney, liver, thymus, testis, colon, placenta, trachea, pancreas, kidney, gastric mucosa, colon, liver, cerebellum, skin, cortex (Alzheimer's and normal), hypothalamus, cortex, amygdala, cerebellum, hippocampus, choroid, plexus, thalamus, and spinal cord.

To demonstrate that protein kinase-like protein is involved in the disease process of COPD, the initial expression panel consists of RNA samples from respiratory tissues and inflammatory cells relevant to COPD: lung (adult and fetal), trachea, freshly isolated alveolar type II cells, cultured human bronchial epithelial cells, cultured small airway epithelial cells, cultured bronchial sooth muscle cells, cultured H441 cells (Clara-like), freshly isolated neutrophils and monocytes, and cultured monocytes (macrophage-like). Body map profiling also is carried out, using total RNA panels purchased from Clontech. The tissues are adrenal gland, bone marrow, brain, colon, heart, kidney, liver, lung, mammary gland, pancreas, prostate, salivary gland, skeletal muscle, small intestine, spleen, stomach, testis, thymus, trachea, thyroid, and uterus.

To demonstrate that protein kinase-like protein is involved in the disease process of obesity, expression is determined in the following tissues: subcutaneous adipose tissue, mesenteric adipose tissue, adrenal gland, bone marrow, brain (cerebellum, spinal cord, cerebral cortex, caudate, medulla, substantia nigra, and putamen), colon, fetal brain, heart, kidney, liver, lung, mammary gland, pancreas, placenta, prostate, salivary gland, skeletal muscle small intestine, spleen, stomach, testes, thymus, thyroid trachea, and uterus. Neuroblastoma cell lines SK-Nr-Be (2), Hr, Sk-N-As, HTB-10, IMR-32, SNSY-5Y, T3, SK-N-D2, D283, DAOY, CHP-2, U87MG, BE(2)C, T986, KANTS, M059K, CHP234, C6 (rat), SK-N-Fl, SK-PU-DW, PFSK-1, BE(2) M17, and MCIXC also are tested for protein kinase-like protein expression. As a final step, the expression of protein kinase-like protein in cells derived from normal individuals with the expression of cells derived from obese individuals is compared.

To demonstrate that protein kinase-like protein is involved in the disease process of diabetes, the following whole body panel is screened to show predominant or relatively high expression: subcutaneous and mesenteric adipose tissue, adrenal gland, bone marrow, brain, colon, fetal brain, heart, hypothalamus, kidney, liver, lung, mammary gland, pancreas, placenta, prostate, salivary gland, skeletal muscle, small intestine, spleen, stomach, testis, thymus, thyroid, trachea, and uterus. Human islet cells and an islet cell library also are tested. As a final step, the expression of protein kinase-like protein in cells derived from normal individuals with the expression of cells derived from diabetic individuals is compared.

Quantitative expression profiling. Quantitative expression profiling is performed by the form of quantitative PCR analysis called "kinetic analysis" firstly described in Higuchi et al., BioTechnology 10, 413–17, 1992, and Higuchi et al., BioTechnology 11, 1026–30, 1993. The principle is that at any given cycle within the exponential phase of PCR, the amount of product is proportional to the initial number of template copies.

If the amplification is performed in the presence of an internally quenched fluorescent oligonucleotide (TaqMan probe) complementary to the target sequence, the probe is cleaved by the 5'–3' endonuclease activity of Taq DNA polymerase and a fluorescent dye released in the medium (Holland et al., Proc. Natl. Acad. Sci. U.S.A. 88, 7276–80, 1991). Because the fluorescence emission will increase in direct proportion to the amount of the specific amplified product, the exponential growth phase of PCR product can be detected and used to determine the initial template concentration (Heid et al., Genome Res. 6, 986–94, 1996, and Gibson et al., Genome Res. 6, 995–1001, 1996).

The amplification of an endogenous control can be performed to standardize the amount of sample RNA added to a reaction. In this kind of experiment, the control of choice is the 18S ribosomal RNA. Because reporter dyes with differing emission spectra are available, the target and the endogenous control can be independently quantified in the same tube if probes labeled with different dyes are used.

All "real time PCR" measurements of fluorescence are made in the ABI Prism 7700.

RNA extraction and cDNA preparation. Total RNA from the tissues listed above are used for expression quantification. RNAs labeled "from autopsy" were extracted from autoptic tissues with the TRIzol reagent (Life Technologies, MD) according to the manufacturer's protocol.

Fifty μg of each RNA were treated with DNase I for 1 hour at 37° C. in the following reaction mix: 0.2 U/μl RNase-free DNase I (Roche Diagnostics, Germany); 0.4 U/μl RNase inhibitor (PE Applied Biosystems, CA); 10 mM Tris-HCl pH 7.9; 10 mM $MgCl_2$; 50 mM NaCl; and 1 mM DTT.

After incubation, RNA is extracted once with 1 volume of phenol:chloroform:—isoamyl alcohol (24:24:1) and once with chloroform, and precipitated with ⅒ volume of 3 M NaAcetate, pH5.2, and 2 volumes of ethanol.

Fifty μg of each RNA from the autoptic tissues are DNase treated with the DNA-free kit purchased from Ambion (Ambion, Tex.). After resuspension and spectrophotometric quantification, each sample is reverse transcribed with the TaqMan Reverse Transcription Reagents (PE Applied Biosystems, CA) according to the manufacturer's protocol. The final concentration of RNA in the reaction mix is 200 ng/μL. Reverse transcription is carried out with 2.5 μM of random hexamer primers.

TaqMan quantitative analysis. Specific primers and probe are designed according to the recommendations of PE Applied Biosystems; the probe can be labeled at the 5' end FAM (6-carboxy-fluorescein) and at the 3' end with TAMRA (6-carboxy-tetramethyl-rhodamine). Quantification experiments are performed on 10 ng of reverse transcribed RNA from each sample. Each determination is done in triplicate.

Total cDNA content is normalized with the simultaneous quantification (multiplex PCR) of the 18S ribosomal RNA using the Pre-Developed TaqMan Assay Reagents (PDAR) Control Kit (PE Applied Biosystems, CA).

The assay reaction mix is as follows: 1× final TaqMan Universal PCR Master Mix (from 2× stock) (PE Applied Biosystems, CA); 1× PDAR control —18S RNA (from 20× stock); 300 nM forward primer; 900 nM reverse primer; 200 nM probe; 10 ng cDNA; and water to 25 μl.

Each of the following steps are carried out once: pre PCR, 2 minutes at 50° C., and 10 minutes at 95° C. The following steps are carried out 40 times: denaturation, 15 seconds at 95° C., annealing/extension, 1 minute at 60° C.

The experiment is performed on an ABI Prism 7700 Sequence Detector (PE Applied Biosystems, CA). At the end of the run, fluorescence data acquired during PCR are processed as described in the ABI Prism 7700 user's manual in order to achieve better background subtraction as well as signal linearity with the starting target quantity.

EXAMPLE 7

Proliferation Inhibition Assay: Antisense Oligonucleotides Suppress the Growth of Cancer Cell Lines The cell line used for testing is the human colon cancer cell line HCT116. Cells are cultured in RPMI-1640 with 10–15% fetal calf serum at a concentration of 10,000 cells per milliliter in a volume of 0.5 ml and kept at 37° C. in a 95% air/5% $CO_2$ atmosphere.

Phosphorothioate oligoribonucleotides are synthesized on an Applied Biosystems Model 380B DNA synthesizer using phosphoroamidite chemistry. A sequence of 24 bases complementary to the nucleotides at position 1 to 24 of SEQ ID NOS: 1, 8 and 10 is used as the test oligonucleotide. As a control, another (random) sequence is used: 5'-TCA ACT GAC TAG ATG TAC ATG GAC-3'. Following assembly and deprotection, oligonucleotides are ethanol-precipitated twice, dried, and suspended in phosphate buffered saline at the desired concentration. Purity of the oligonucleotides is tested by capillary gel electrophoresis and ion exchange HPLC. The purified oligonucleotides are added to the culture medium at a concentration of 10 μM once per day for seven days.

The addition of the test oligonucleotide for seven days results in significantly reduced expression of human protein kinase-like protein as determined by Western blotting. This effect is not observed with the control oligonucleotide. After 3 to 7 days, the number of cells in the cultures is counted using an automatic cell counter. The number of cells in cultures treated with the test oligonucleotide (expressed as 100%) is compared with the number of cells in cultures treated with the control oligonucleotide. The number of cells in cultures treated with the test oligonucleotide is not more than 30% of control, indicating that the inhibition of human protein kinase-like protein has an anti-proliferative effect on cancer cells.

EXAMPLE 8

In Vivo Testing of Compounds/Target Validation

1. Acute Mechanistic Assays 1.1. Reduction in Mitogenic Plasma Hormone Levels

This non-tumor assay measures the ability of a compound to reduce either the endogenous level of a circulating hormone or the level of hormone produced in response to a biologic stimulus. Rodents are administered test compound (p.o., i.p., i.v., i.m., or s.c.). At a predetermined time after administration of test compound, blood plasma is collected. Plasma is assayed for levels of the hormone of interest. If the normal circulating levels of the hormone are too low and/or variable to provide consistent results, the level of the hormone may be elevated by a pre-treatment with a biologic stimulus (i.e., LHRH may be injected i.m. into mice at a dosage of 30 ng/mouse to induce a burst of testosterone synthesis). The timing of plasma collection would be adjusted to coincide with the peak of the induced hormone response. Compound effects are compared to a vehicle-treated control group. An F-test is preformed to determine if the variance is equal or unequal followed by a Student's t-test. Significance is p value $\leq 0.05$ compared to the vehicle control group.

1.2. Hollow Fiber Mechanism of Action Assay

Hollow fibers are prepared with desired cell line(s) and implanted intraperitoneally and/or subcutaneously in rodents. Compounds are administered p.o., i.p., i.v., i.m., or s.c. Fibers are harvested in accordance with specific readout assay protocol, these may include assays for gene expression (bDNA, PCR, or Taqman), or a specific biochemical activity (i.e., cAMP levels. Results are analyzed by Student's t-test or Rank Sum test after the variance between groups is compared by an F-test, with significance at $p<0.05$ as compared to the vehicle control group.

2. Subacute Functional In Vivo Assays 2.1. Reduction in Mass of Hormone Dependent Tissues This is another non-tumor assay that measures the ability of a compound to reduce the mass of a hormone dependent tissue (i.e., seminal vesicles in males and uteri in females). Rodents are administered test compound (p.o., i.p., i.v., i.m., or s.c.) according to a predetermined schedule and for a predetermined duration (i.e., 1 week). At termination of the study, animals are weighed, the target organ is excised, any fluid is expressed, and the weight of the organ is recorded. Blood plasma may also be collected. Plasma may be assayed for levels of a hormone of interest or for levels of test agent. Organ weights may be directly compared or they may be normalized for the body weight of the animal. Compound effects are compared to a vehicle-treated control group. An F-test is preformed to determine if the variance is equal or unequal followed by a Student's t-test. Significance is p value $\leq 0.05$ compared to the vehicle control group.

2.2. Hollow Fiber Proliferation Assay

Hollow fibers are prepared with desired cell line(s) and implanted intraperitoneally and/or subcutaneously in rodents. Compounds are administered p.o., i.p., i.v., i.m., or s.c. Fibers are harvested in accordance with specific readout assay protocol. Cell proliferation is determined by measuring a marker of cell number (i.e., MTT or LDH). The cell number and change in cell number from the starting inoculum are analyzed by Student's t-test or Rank Sum test after the variance between groups is compared by an F-test, with significance at $p \leq 0.05$ as compared to the vehicle control group.

2.3 Anti-angiogenesis Models 2.3.1. Corneal Angiogenesis

Hydron pellets with or without growth factors or cells are implanted into a micropocket surgically created in the rodent cornea. Compound administration may be systemic or local (compound mixed with growth factors in the hydron pellet). Corneas are harvested at 7 days post implantation immediately following intracardiac infusion of colloidal carbon and are fixed in 10% formalin. Readout is qualitative scoring and/or image analysis. Qualitative scores are compared by Rank Sum test. Image analysis data is evaluated by measuring the area of neovascularization (in pixels) and group averages are compared by Student's t-test (2 tail). Significance is $p<0.05$ as compared to the growth factor or cells only group.

2.3.2. Matrigel Angiogenesis

Matrigel, containing cells or growth factors, is injected subcutaneously. Compounds are administered p.o., i.p., i.v., i.m., or s.c. Matrigel plugs are harvested at predetermined time point(s) and prepared for readout. Readout is an ELISA-based assay for hemoglobin concentration and/or histological examination (i.e. vessel count, special staining for endothelial surface markers: CD31, factor-8). Readouts are analyzed by Student's t-test, after the variance between groups is compared by an F-test, with significance determined at $p \leq 0.05$ as compared to the vehicle control group.

3. Primary Antitumor Efficacy 3.1. Early Therapy Models 3.1.1. Subcutaneous Tumor Tumor cells or fragments are implanted subcutaneously on Day 0. Vehicle and/or compounds are administered p.o., i.p., i.v., i.m., or s.c. according to a predetermined schedule starting at a time, usually on Day 1, prior to the ability to measure the tumor burden. Body weights and tumor measurements are recorded 2–3 times weekly. Mean net body and tumor weights are calculated for each data collection day. Anti-tumor efficacy may be initially determined by comparing the size of treated (T) and control (C) tumors on a given day by a Student's t-test, after the variance between groups is compared by an F-test, with significance determined at $p \leq 0.05$. The experiment may also be continued past the end of dosing in which case tumor measurements would continue to be recorded to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is $p<0.05$.

3.1.2. Intraperitoneal/Intracranial Tumor Models

Tumor cells are injected intraperitoneally or intracranially on Day 0. Compounds are administered p.o., i.p., i.v., i.m., or s.c. according to a predetermined schedule starting on Day 1. Observations of morbidity and/or mortality are recorded twice daily. Body weights are measured and recorded twice weekly. Morbidity/mortality data is expressed in terms of the median time of survival and the number of long-term survivors is indicated separately. Survival times are used to generate Kaplan-Meier curves. Significance is $p \leq 0.05$ by a log-rank test compared to the control group in the experiment.

3.2. Established Disease Model

Tumor cells or fragments are implanted subcutaneously and grown to the desired size for treatment to begin. Once at the predetermined size range, mice are randomized into treatment groups. Compounds are administered p.o., i.p., i.v., i.m., or s.c. according to a predetermined schedule. Tumor and body weights are measured and recorded 2–3 times weekly. Mean tumor weights of all groups over days post inoculation are graphed for comparison. An F-test is preformed to determine if the variance is equal or unequal followed by a Student's t-test to compare tumor sizes in the treated and control groups at the end of treatment. Significance is $p \leq 0.05$ as compared to the control group. Tumor measurements may be recorded after dosing has stopped to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is p value $\leq 0.05$ compared to the vehicle control group.

3.3. Orthotopic Disease Models 3.3.1. Mammary Fat Pad Assay

Tumor cells or fragments, of mammary adenocarcinoma origin, are implanted directly into a surgically exposed and reflected mammary fat pad in rodents. The fat pad is placed back in its original position and the surgical site is closed. Hormones may also be administered to the rodents to support the growth of the tumors. Compounds are administered p.o., i.p., i.v., i.m., or s.c. according to a predetermined schedule. Tumor and body weights are measured and recorded 2–3 times weekly. Mean tumor weights of all groups over days post inoculation are graphed for comparison. An F-test is preformed to determine if the variance is equal or unequal followed by a Student's t-test to compare tumor sizes in the treated and control groups at the end of treatment. Significance is $p \leq 0.05$ as compared to the control group.

Tumor measurements may be recorded after dosing has stopped to monitor tumor growth delay. Tumor growth delays are expressed as the difference in the median time for the treated and control groups to attain a predetermined size divided by the median time for the control group to attain that size. Growth delays are compared by generating Kaplan-Meier curves from the times for individual tumors to attain the evaluation size. Significance is p value $\leq 0.05$ compared to the vehicle control group. In addition, this model provides an opportunity to increase the rate of spontaneous metastasis of this type of tumor. Metastasis can be assessed at termination of the study by counting the number of visible foci per target organ, or measuring the target organ weight. The means of these endpoints are compared by Student's t-test after conducting an F-test, with significance determined at $p \leq 0.05$ compared to the control group in the experiment.

3.3.2. Intraprostatic Assay

Tumor cells or fragments, of prostatic adenocarcinoma origin, are implanted directly into a surgically exposed dorsal lobe of the prostate in rodents. The prostate is externalized through an abdominal incision so that the tumor can be implanted specifically in the dorsal lobe while verifying that the implant does not enter the seminal vesicles. The successfully inoculated prostate is replaced in the abdomen and the incisions through the abdomen and skin are closed. Hormones may also be administered to the rodents to support the growth of the tumors. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is $p \leq 0.05$ as compared to the control group. This model provides an opportunity to increase the rate of spontaneous metastasis of this type of tumor. Metastasis can be assessed at termination of the study by counting the number of visible foci per target organ (i.e., the lungs), or measuring the target organ weight (i.e., the regional lymph nodes). The means of these endpoints are compared by Student's t-test after conducting an F-test, with significance determined at $p \leq 0.05$ compared to the control group in the experiment.

3.3.3. Intrabronchial Assay

Tumor cells of pulmonary origin may be implanted intrabronchially by making an incision through the skin and exposing the trachea. The trachea is pierced with the beveled end of a 25 gauge needle and the tumor cells are inoculated into the main bronchus using a flat-ended 27 gauge needle with a 90° bend. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is $p \leq 0.05$ as compared to the control group. This model provides an opportunity to increase the rate of spontaneous metastasis of this type of tumor. Metastasis can be assessed at termination of the study by counting the number of visible foci per target organ (i.e., the contralateral lung), or measuring the target organ weight. The means of these endpoints are compared by Student's t-test after conducting an F-test, with significance determined at $p < 0.05$ compared to the control group in the experiment.

3.3.4. Intracecal Assay

Tumor cells of gastrointestinal origin may be implanted intracecally by making an abdominal incision through the skin and externalizing the intestine. Tumor cells are inoculated into the cecal wall without penetrating the lumen of the intestine using a 27 or 30 gauge needle. Compounds are administered p.o., i.p., i.v., i.m., or s.c. according to a predetermined schedule. Body weights are measured and recorded 2–3 times weekly. At a predetermined time, the experiment is terminated and the animal is dissected. The size of the primary tumor is measured in three dimensions using either a caliper or an ocular micrometer attached to a dissecting scope. An F-test is preformed to determine if the variance is equal or unequal followed by a Student's t-test to compare tumor sizes in the treated and control groups at the end of treatment. Significance is $p \leq 0.05$ as compared to the control group. This model provides an opportunity to increase the rate of spontaneous metastasis of this type of tumor. Metastasis can be assessed at termination of the study by counting the number of visible foci per target organ (i.e., the liver), or measuring the target organ weight. The means of these endpoints are compared by Student's t-test after conducting an F-test, with significance determined at $p \leq 0.05$ compared to the control group in the experiment.

4. Secondary (Metastatic) Antitumor Efficacy 4.1. Spontaneous Metastasis

Tumor cells are inoculated s.c. and the tumors allowed to grow to a predetermined range for spontaneous metastasis studies to the lung or liver. These primary tumors are then excised. Compounds are administered p.o., i.p., i.v., i.m., or s.c. according to a predetermined schedule which may include the period leading up to the excision of the primary tumor to evaluate therapies directed at inhibiting the early stages of tumor metastasis. Observations of morbidity and/or mortality are recorded daily. Body weights are measured and recorded twice weekly. Potential endpoints include survival time, numbers of visible foci per target organ, or target organ weight. When survival time is used as the endpoint the other values are not determined. Survival data is used to generate Kaplan-Meier curves. Significance is $p \leq 0.05$ by a log-rank test compared to the control group in the experiment. The mean number of visible tumor foci, as determined under a dissecting microscope, and the mean target organ weights are compared by Student's t-test after conducting an F-test, with significance determined at $p \leq 0.05$ compared to the control group in the experiment for both of these endpoints.

4.2. Forced Metastasis

Tumor cells are injected into the tail vein, portal vein, or the left ventricle of the heart in experimental (forced) lung, liver, and bone metastasis studies, respectively. Compounds are administered p.o., i.p., i.v., i.m., or s.c. according to a predetermined schedule. Observations of morbidity and/or mortality are recorded daily. Body weights are measured and recorded twice weekly. Potential endpoints include survival time, numbers of visible foci per target organ, or target organ weight. When survival time is used as the endpoint the other values are not determined. Survival data is used to generate Kaplan-Meier curves. Significance is $p \leq 0.05$ by a log-rank test compared to the control group in the experiment. The mean number of visible tumor foci, as determined under a dissecting microscope, and the mean target organ weights are compared by Student's t-test after conducting an F-test, with significance at $p \leq 0.05$ compared to the vehicle control group in the experiment for both endpoints.

EXAMPLE 9

In Vivo Testing of Compounds/Target Validation

1. Pain

Acute Pain

Acute pain is measured on a hot plate mainly in rats. Two variants of hot plate testing are used: In the classical variant animals are put on a hot surface (52 to 56° C.) and the latency time is measured until the animals show nocifensive behavior, such as stepping or foot licking. The other variant is an increasing temperature hot plate where the experimental animals are put on a surface of neutral temperature. Subsequently this surface is slowly but constantly heated until the animals begin to lick a hind paw. The temperature which is reached when hind paw licking begins is a measure for pain threshold.

Compounds are tested against a vehicle treated control group. Substance application is performed at different time points via different application routes (i.v., i.p., p.o., i.t., i.c.v., s.c., intradermal, transdermal) prior to pain testing.

Persistent Pain

Persistent pain is measured with the formalin or capsaicin test, mainly in rats. A solution of 1 to 5% formalin or 10 to 100 μg capsaicin is injected into one hind paw of the experimental animal. After formalin or capsaicin application the animals show nocifensive reactions like flinching, licking and biting of the affected paw. The number of nocifensive reactions within a time frame of up to 90 minutes is a measure for intensity of pain.

Compounds are tested against a vehicle treated control group. Substance application is performed at different time points via different application routes (i.v., i.p., p.o., i.t., i.c.v., s.c., intradermal, transdermal) prior to formalin or capsaicin administration.

Neuropathic Pain

Neuropathic pain is induced by different variants of unilateral sciatic nerve injury mainly in rats. The operation is performed under anesthesia. The first variant of sciatic nerve injury is produced by placing loosely constrictive ligatures around the common sciatic nerve. The second variant is the tight ligation of about the half of the diameter of the common sciatic nerve. In the next variant, a group of models is used in which tight ligations or transections are made of either the L5 and L6 spinal nerves, or the L % spinal nerve only. The fourth variant involves an axotomy of two of the three terminal branches of the sciatic nerve (tibial and common peroneal nerves) leaving the remaining sural nerve intact whereas the last variant comprises the axotomy of only the tibial branch leaving the sural and common nerves uninjured. Control animals are treated with a sham operation.

Postoperatively, the nerve injured animals develop a chronic mechanical allodynia, cold allodynioa, as well as a thermal hyperalgesia. Mechanical allodynia is measured by means of a pressure transducer (electronic von Frey Anesthesiometer, IITC Inc.-Life Science Instruments, Woodland Hills, SA, USA; Electronic von Frey System, Somedic Sales AB, Hörby, Sweden). Thermal hyperalgesia is measured by means of a radiant heat source (Plantar Test, Ugo Basile, Comerio, Italy), or by means of a cold plate of 5 to 10° C. where the nocifensive reactions of the affected hind paw are counted as a measure of pain intensity. A further test for cold induced pain is the counting of nocifensive reactions, or duration of nocifensive responses after plantar administration of acetone to the affected hind limb. Chronic pain in general is assessed by registering the circadanian rhythms in activity (Suijo and Arndt, Universität zu Köln, Cologne, Germany), and by scoring differences in gait (foot print patterns; FOOTPRINTS program, Klapdor et al., 1997. A low cost method to analyze footprint patterns. J. Neurosci. Methods 75, 49–54).

Compounds are tested against sham operated and vehicle treated control groups. Substance application is performed at different time points via different application routes (i.v., i.p., p.o., i.t., i.c.v., s.c., intradermal, transdermal) prior to pain testing.

Inflammatory Pain

Inflammatory pain is induced mainly in rats by injection of 0.75 mg carrageenan or complete Freund's adjuvant into one hind paw. The animal develop an edema with mechanical allodynia as well as thermal hyperalgesia.

Mechanical allodynia is measured by means of a pressure transducer (electronic von Frey Anesthesiometer, IITC Inc.-Life Science Instruments, Woodland Hills, SA, USA). Thermal hyperalgesia is measured by means of a radiant heat source (Plantar Test, Ugo Basile, Comerio, Italy, Paw thermal stimulator, G. Ozaki, University of California, USA). For edema measurement two methods are being used. In the first method, the animals are sacrificed and the affected hindpaws sectioned and weighed. The second method comprises differences in paw volume by measuring water displacement in a plethysmometer (Ugo Basile, Comerio, Italy).

Compounds are tested against uninflamed as well as vehicle treated control groups. Substance application is performed at different time points via different application routes (i.v., i.p., p.o., i.t., i.c.v., s.c., intradermal, transdermal) prior to pain testing.

Diabetic Neuropathic Pain

Rats treated with a single intraperitoneal injection of 50 to 80 mg/kg streptozotocin develop a profound hyperglycemia and mechanical allodynia within 1 to 3 weeks. Mechanical allodynia is measured by means of a pressure transducer (electronic von Frey Anesthesiometer, IITC Inc.-Life Science Instruments, Woodland Hills, SA, USA).

Compounds are tested against diabetic and non-diabetic vehicle treated control groups. Substance application is performed at different time points via different application routes (i.v., i.p., p.o., i.t., i.c.v., s.c., intradermal, transdermal) prior to pain testing.

2. Parkinson's Disease

6-Hydroxydopamine (6-OH-DA) Lesion

Degeneration of the dopaminergic nigrostriatal and striatopallidal pathways is the central pathological event in Parkinson's disease. This disorder has been mimicked experimentally in rats using single/sequential unilateral stereotaxic injections of 6-OH-DA into the medium forebrain bundle (MFB).

Male Wistar rats (Harlan Winkelmann, Germany), weighing 200±250 g at the beginning of the experiment, are used. The rats are maintained in a temperature- and humidity-controlled environment under a 12 h light/dark cycle with free access to food and water when not in experimental sessions. The following in vivo protocols are approved by the governmental authorities. All efforts are made to minimize animal suffering, to reduce the number of animals used, and to utilize alternatives to in vivo techniques.

Animals are administered pargyline on the day of surgery (Sigma, St. Louis, Mo., USA; 50 mg/kg i.p.) in order to inhibit metabolism of 6-OHDA by monoamine oxidase and desmethylimipramine HCl (Sigma; 25 mg/kg i.p.) in order to prevent uptake of 6-OHDA by noradrenergic terminals. Thirty minutes later the rats are anesthetized with sodium pentobarbital (50 mg/kg) and placed in a stereotaxic frame. In order to lesion the DA nigrostriatal pathway 4 µl of 0.01% ascorbic acid-saline containing 8 µg of 6-OHDA HBr (Sigma) are injected into the left medial fore-brain bundle at a rate of 1 µl/min (2.4 mm anterior, 1.49 mm lateral, −2.7 mm ventral to Bregma and the skull surface). The needle is left in place an additional 5 min to allow diffusion to occur.

Stepping Test

Forelimb akinesia is assessed three weeks following lesion placement using a modified stepping test protocol. In brief, the animals are held by the experimenter with one hand fixing the hindlimbs and slightly raising the hind part above the surface. One paw is touching the table, and is then moved slowly sideways (5 s for 1 m), first in the forehand and then in the backhand direction. The number of adjusting steps is counted for both paws in the backhand and forehand direction of movement. The sequence of testing is right paw forehand and backhand adjusting stepping, followed by left paw forehand and backhand directions. The test is repeated three times on three consecutive days, after an initial training period of three days prior to the first testing. Forehand adjusted stepping reveals no consistent differences between lesioned and healthy control animals. Analysis is therefore restricted to backhand adjusted stepping.

Balance Test

Balance adjustments following postural challenge are also measured during the stepping test sessions. The rats are held in the same position as described in the stepping test and, instead of being moved sideways, tilted by the experimenter towards the side of the paw touching the table. This maneuver results in loss of balance and the ability of the rats to regain balance by forelimb movements is scored on a scale ranging from 0 to 3. Score 0 is given for a normal forelimb placement. When the forelimb movement is delayed but recovery of postural balance detected, score 1 is given. Score 2 represents a clear, yet insufficient, forelimb reaction, as evidenced by muscle contraction, but lack of success in recovering balance, and score 3 is given for no reaction of movement. The test is repeated three times a day on each side for three consecutive days after an initial training period of three days prior to the first testing.

Staircase Test (Paw Reaching)

A modified version of the staircase test is used for evaluation of paw reaching behavior three weeks following primary and secondary lesion placement. Plexiglass test boxes with a central platform and a removable staircase on each side are used. The apparatus is designed such that only the paw on the same side at each staircase can be used, thus providing a measure of independent forelimb use. For each test the animals are left in the test boxes for 15 min. The double staircase is filled with 7×3 chow pellets (Precision food pellets, formula: P, purified rodent diet, size 45 mg; Sandown Scientific) on each side. After each test the number of pellets eaten (successfully retrieved pellets) and the number of pellets taken (touched but dropped) for each paw and the success rate (pellets eaten/pellets taken) are counted separately. After three days of food deprivation (12 g per animal per day) the animals are tested for 11 days. Full analysis is conducted only for the last five days.

MPTP Treatment

The neurotoxin 1-methyl-4-phenyl-1,2,3,6-tetrahydro-pyridine (MPTP) causes degeneration of mesencephalic dopaminergic (DAergic) neurons in rodents, non-human primates, and humans and, in so doing, reproduces many of the symptoms of Parkinson's disease. MPTP leads to a marked decrease in the levels of dopamine and its metabolites, and in the number of dopaminergic terminals in the striatum as well as severe loss of the tyrosine hydroxylase (TH)-immunoreactive cell bodies in the substantia nigra, pars compacta.

In order to obtain severe and long-lasting lesions, and to reduce mortality, animals receive single injections of MPTP, and are then tested for severity of lesion 7–10 days later. Successive MPTP injections are administered on days 1, 2 and 3. Animals receive application of 4 mg/kg MPTP hydrochloride (Sigma) in saline once daily. All injections are intraperitoneal (i.p.) and the MPTP stock solution is frozen between injections. Animals are decapitated on day 11.

Immunohistology

At the completion of behavioral experiments, all animals are anaesthetized with 3 ml thiopental (1 g/40 ml i.p., Tyrol Pharma). The mice are perfused transcardially with 0.01 M PBS (pH 7.4) for 2 min, followed by 4% paraformaldehyde (Merck) in PBS for 15 min. The brains are removed and placed in 4% paraformaldehyde for 24 h at 4° C. For dehydration they are then transferred to a 20% sucrose (Merck) solution in 0.1 M PBS at 4° C. until they sink. The brains are frozen in methylbutan at −20° C. for 2 min and stored at −70° C. Using a sledge microtome (mod. 3800-Frigocut, Leica), 25 µm sections are taken from the genu of the corpus callosum (AP 1.7 mm) to the hippocarnpus (AP 21.8 mm) and from AP 24.16 to AP 26.72. Forty-six sections are cut and stored in assorters in 0.25 M Tris buffer (pH 7.4) for immunohistochemistry.

A series of sections is processed for free-floating tyrosine hydroxylase (TH) immunohistochemistry. Following three rinses in 0.1 M PBS, endogenous peroxidase activity is quenched for 10 min in 0.3% $H_2O_2$+PBS. After rinsing in PBS, sections are preincubated in 10% normal bovine serum (Sigma) for 5 min as blocking agent and transferred to either primary anti-rat TH rabbit antiserum (dilution 1:2000).

Following overnight incubation at room temperature, sections for TH immunoreactivity are rinsed in PBS (2×10 min) and incubated in biotinylated anti-rabbit immunoglobulin G raised in goat (dilution 1:200) (Vector) for 90 min, rinsed repeatedly and transferred to Vectastain ABC (Vector) solution for 1 h. 3,.3'-Diaminobenzidine tetrahydrochloride (DAB; Sigma) in 0.1 M PBS, supplemented with 0.005% $H_2O_2$, serves as chromogen in the subsequent visualization reaction. Sections are mounted on to gelatin-coated slides, left to dry overnight, counter-stained with hematoxylin dehydrated in ascending alcohol concentrations and cleared in butylacetate. Coverslips are mounted on entellan.

Rotarod Test

We use a modification of the procedure described by Rozas and Labandeira-Garcia (1997), with a CR-1 Rotamex system (Columbus Instruments, Columbus, Ohio) comprising an IBM-compatible personal computer, a CIO-24 data acquisition card, a control unit, and a four-lane rotarod unit. The rotarod unit consists of a rotating spindle (diameter 7.3 cm) and individual compartments for each mouse. The system software allows preprogramming of session protocols with varying rotational speeds (0–80 rpm). Infrared beams are used to detect when a mouse has fallen onto the base grid beneath the rotarod. The system logs the fall as the end of the experiment for that mouse, and the total time on the rotarod, as well as the time of the fall and all the set-up parameters, are recorded. The system also allows a weak current to be passed through the base grid, to aid training.

3. Dementia

The Object Recognition Task

The object recognition task has been designed to assess the effects of experimental manipulations on the cognitive performance of rodents. A rat is placed in an open field, in which two identical objects are present. The rats inspects both objects during the first trial of the object recognition task. In a second trial, after a retention interval of for example 24 hours, one of the two objects used in the first trial, the 'familiar' object, and a novel object are placed in the open field. The inspection time at each of the objects is registered. The basic measures in the OR task is the time spent by a rat exploring the two object the second trial. Good retention is reflected by higher exploration times towards the novel than the 'familiar' object.

Administration of the putative cognition enhancer prior to the first trial predominantly allows assessment of the effects on acquisition, and eventually on consolidation processes. Administration of the testing compound after the first trial allows to assess the effects on consolidation processes, whereas administration before the second trial allows to measure effects on retrieval processes.

The Passive Avoidance Task

The passive avoidance task assesses memory performance in rats and mice. The inhibitory avoidance apparatus consists of a two-compartment box with a light compartment and a dark compartment. The two compartments are separated by a guillotine door that can be operated by the experimenter. A threshold of 2 cm separates the two compartments when the guillotine door is raised. When the door is open, the illumination in the dark compartment is about 2 lux. The light intensity is about 500 lux at the center of the floor of the light compartment.

Two habituation sessions, one shock session, and a retention session are given, separated by inter-session intervals of 24 hours. In the habituation sessions and the retention session the rat is allowed to explore the apparatus for 300 sec. The rat is placed in the light compartment, facing the wall opposite to the guillotine door. After an accommodation period of 15 sec. the guillotine door is opened so that all parts of the apparatus can be visited freely. Rats normally avoid brightly lit areas and will enter the dark compartment within a few seconds.

In the shock session the guillotine door between the compartments is lowered as soon as the rat has entered the dark compartment with its four paws, and a scrambled 1 mA footshock is administered for 2 sec. The rat is removed from the apparatus and put back into its home cage. The procedure during the retention session is identical to that of the habituation sessions.

The step-through latency, that is the first latency of entering the dark compartment (in sec.) during the retention session is an index of the memory performance of the animal; the longer the latency to enter the dark compartment, the better the retention is. A testing compound in given half an hour before the shock session, together with 1 mg*kg$^{-1}$ scopolamine. Scopolamine impairs the memory performance during the retention session 24 hours later. If the test compound increases the enter latency compared with the scopolamine-treated controls, is likely to possess cognition enhancing potential.

The Morris Water Escape Task

The Morris water escape task measures spatial orientation learning in rodents. It is a test system that has extensively been used to investigate the effects of putative therapeutic on the cognitive functions of rats and mice. The performance of an animal is assessed in a circular water tank with an escape platform that is submerged about 1 cm below the surface of the water. The escape platform is not visible for an animal swimming in the water tank. Abundant extra-maze cues are provided by the furniture in the room, including desks, computer equipment, a second water tank, the presence of the experimenter, and by a radio on a shelf that is playing softly.

The animals receive four trials during five daily acquisition sessions. A trial is started by placing an animal into the pool, facing the wall of the tank. Each of four starting positions in the quadrants north, east, south, and west is used once in a series of four trials; their order is randomized. The escape platform is always in the same position. A trial is terminated as soon as the animal had climbs onto the escape platform or when 90 seconds have elapsed, whichever event occurs first. The animal is allowed to stay on the platform for 30 seconds. Then it is taken from the platform and the next trial is started. If an animal did not find the platform within 90 seconds it is put on the platform by the experimenter and is allowed to stay there for 30 seconds. After the fourth trial of the fifth daily session, an additional trial is given as a probe trial: the platform is removed, and the time the animal spends in the four quadrants is measured for 30 or 60 seconds. In the probe trial, all animals start from the same start position, opposite to the quadrant where the escape platform had been positioned during acquisition.

Four different measures are taken to evaluate the performance of an animal during acquisition training: escape latency, traveled distance, distance to platform, and swimming speed. The following measures are evaluated for the probe trial: time (s) in quadrants and traveled distance (cm) in the four quadrants. The probe trial provides additional information about how well an animal learned the position of the escape platform. If an animal spends more time and swims a longer distance in the quadrant where the platform had been positioned during the acquisition sessions than in any other quadrant, one concludes that the platform position has been learned well.

In order to assess the effects of putative cognition enhancing compounds, rats or mice with specific brain lesions which impair cognitive functions, or animals treated with compounds such as scopolamine or MK-801, which interfere with normal learning, or aged animals which suffer from cognitive deficits, are used.

The T-Maze Spontaneous Alternation Task

The T-maze spontaneous alternation task (TeMCAT) assesses the spatial memory performance in mice. The start arm and the two goal arms of the T-maze are provided with guillotine doors which can be operated manually by the experimenter. A mouse is put into the start arm at the beginning of training. The guillotine door is closed. In the first trial, the 'forced trial', either the left or right goal arm is blocked by lowering the guillotine door. After the mouse has been released from the start arm, it will negotiate the maze, eventually enter the open goal arm, and return to the start position, where it will be confined for 5 seconds, by lowering the guillotine door. Then, the animal can choose freely between the left and right goal arm (all guillotine-doors opened) during 14 'free choice' trials. As soon a the mouse has entered one goal arm, the other one is closed. The mouse eventually returns to the start arm and is free to visit whichever go alarm it wants after having been confined to the start arm for 5 seconds. After completion of 14 free choice trials in one session, the animal is removed from the maze. During training, the animal is never handled.

The percent alternations out of 14 trials is calculated. This percentage and the total time needed to complete the first forced trial and the subsequent 14 free choice trials (in s) is analyzed. Cognitive deficits are usually induced by an injection of scopolamine, 30 min before the start of the training session. Scopolamine reduced the per-cent alternations to chance level, or below. A cognition enhancer, which is always administered before the training session, will at least partially, antagonize the scopolamine-induced reduction in the spontaneous alternation rate.

EXAMPLE 10

Expression of Human Protein Kinase-like Protein

Total RNA used for Taqman quantitative analysis were either purchased (Clontech,CA) or extracted from tissues using TRIzol reagent (Life Technologies, MD) according to a modified vendor protocol which utilizes the Rneasy protocol (Qiagen, CA).

One hundred µg of each RNA were treated with DNase I using RNase free- DNase (Qiagen, CA) for use with RNeasy or QiaAmp columns.

After elution and quantitation with Ribogreen (Molecular Probes Inc., OR), each sample was reverse transcribed using the GibcoBRL Superscript II First Strand Synthesis System for RT-PCR according to vendor protocol (Life Technologies, MD). The final concentration of RNA in the reaction mix was 50 ng/µL. Reverse transcription was performed with 50 ng of random hexamers.

Specific primers and probe were designed according to PE Applied Biosystems' Primer Express program recommendations and are listed below:

```
forward primer:    5'-(CTGTGACCTGAAGTCGGACAAC)-3' reverse primer:    5'-(GGAATGACTGCCTCGAAATCC)-3' probe:             SYBR Green
```

Quantitation experiments were performed on 25 ng of reverse transcribed RNA from each sample. 18S ribosomal RNA was measured as a control using the Pre-Developed TaqMan Assay Reagents (PDAR)(PE Applied Biosystems, CA). The assay reaction mix was as follows:

|  | final |
|---|---|
| TaqMan SYBR Green PCR Master Mix (2x) (PE Applied Biosystems, CA) | 1x |
| Forward primer | 300 nM |
| Reverse primer | 300 nM |
| cDNA | 25 ng |
| Water to | 25 uL |

PCR Conditions:

| Once: | 2' minutes at 50° C. |
|---|---|
|  | 10 minutes at 95° C. |
| 40cycles: | 15 sec. at 95° C. |
|  | 1 minute at 60° C. |

The experiment was performed on an ABI Prism 7700 Sequence Detector (PE Applied Biosystems, CA). At the end of the run, fluorescence data acquired during PCR were processed as described in the ABI Prism 7700 user's manual. Fold change was calculated using the delta-delta CT method with normalization to the 18S values. Relative expression was calculated by normalizing to 18s (D Ct), then making the highest expressing tissue 100 and everything else relative to it. Copy number conversion was performed without normalization using the formula $Cn=10(Ct-40.007)/-3.623$.

Figure 14:
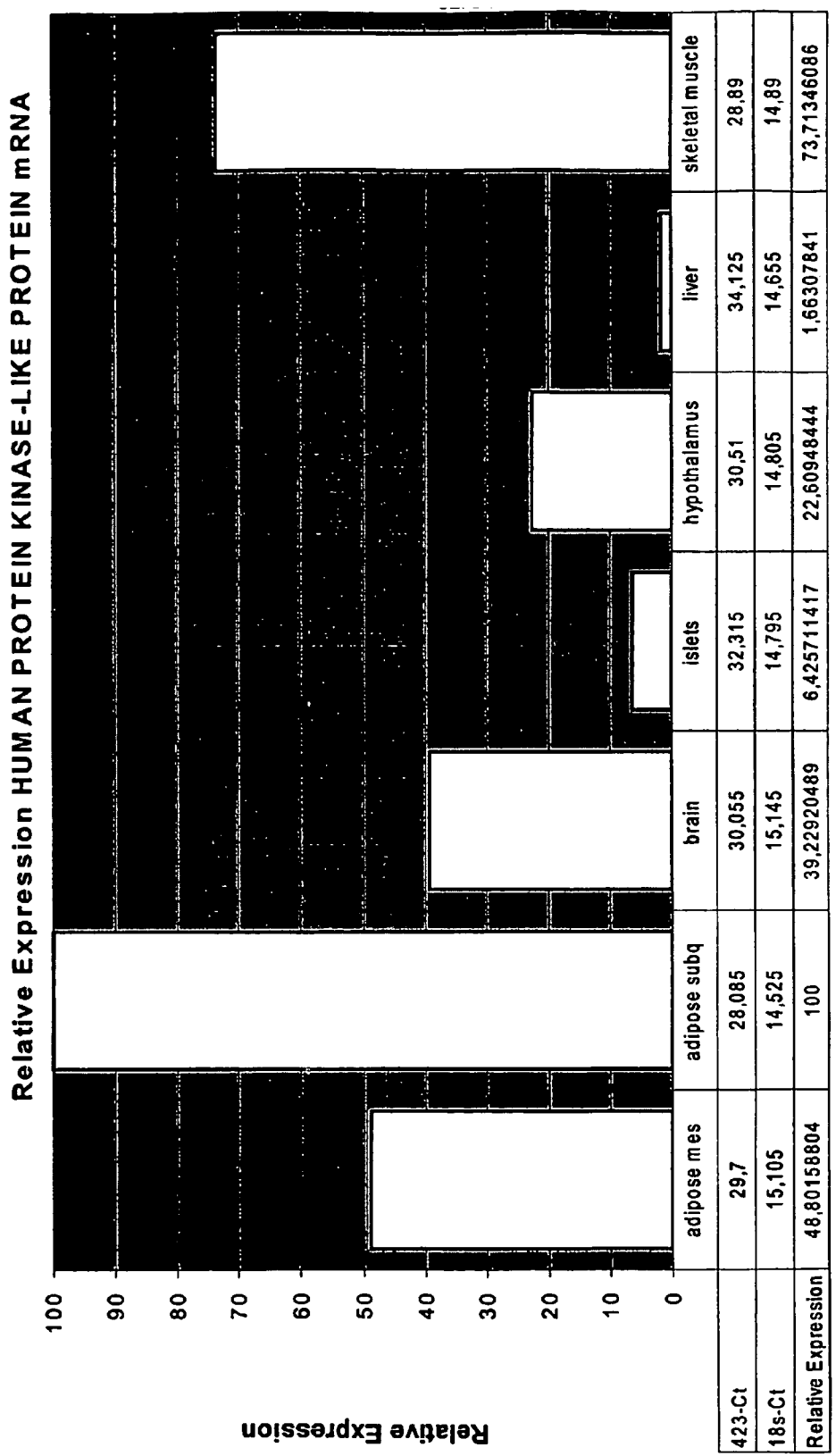
FIG. 14 shows the relative expression of protein kinase-like protein mRNA in tissue relevant for obesity and diabetes.
Figure 15:
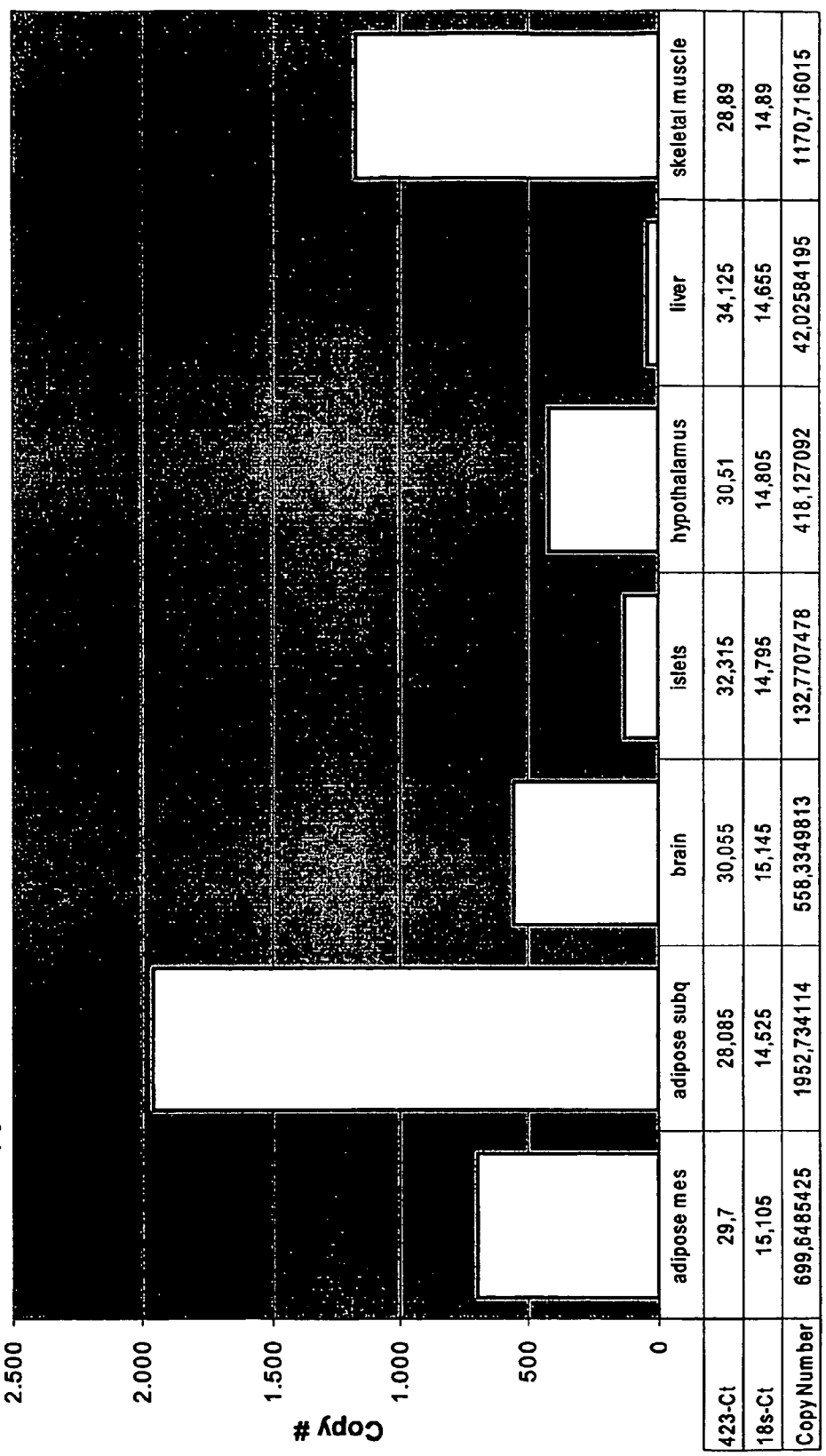
FIG. 15 shows the copy number of protein kinase-like protein mRNA in tissue relevant for obesity and diabetes.
Figure 16:
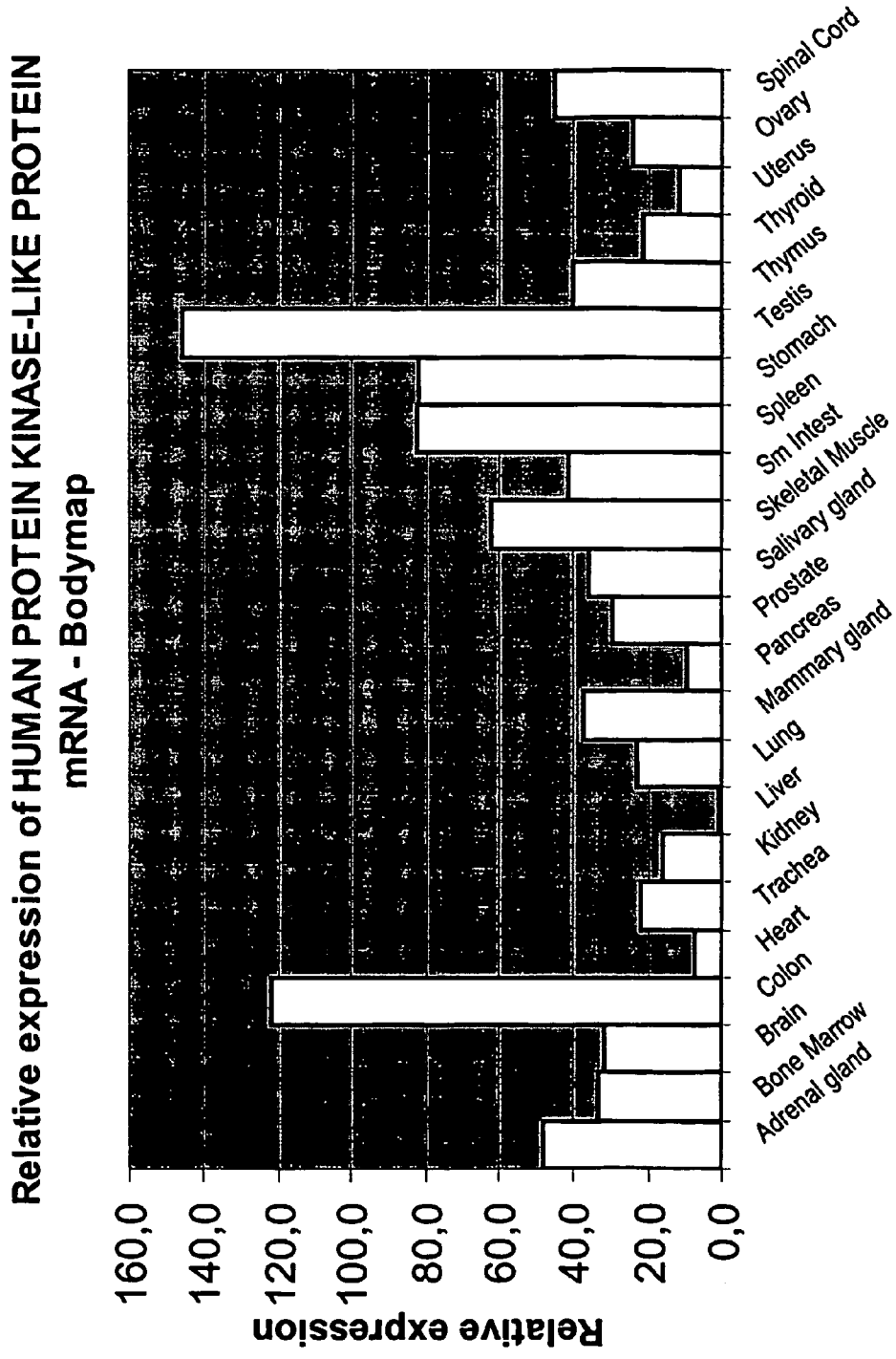
FIG. 16 shows the relative expression profile of protein kinase-like protein mRNA in various human tissues (bodymap).

The results are shown in FIGS. 13, 14, 15 and 16.

Protein kinase-like protein expression in adipose and skeletal muscle could be regulated to increase insulin sensitivity.

References

1. Protein kinases 6. The eukaryotic protein kinase superfamily: kinase (catalytic) domain structure and classification. FASEB J 1995 May;9(8):576–96
2. Protein kinase catalytic domain sequence database: identification of conserved features of primary structure and classification of family members. Methods Enzymol 1991;200:38–62

The invention claimed is:

1. An isolated and purified protein consisting of the amino acid sequence shown in SEQ ID NO:2.

2. An isolated and purified protein consisting an amino acid sequence which is at least 90% identical to the amino acid sequence shown in SEQ ID NO:2 and which has a kinase activity.

3. An isolated and purified polynucleotide comprising at least one strand which consists of a coding sequence for the amino acid sequence shown in SEQ ID NO:2.

4. The polynucleotide of claim 3 wherein the coding sequence is the nucleotide sequence shown in SEQ ID NO: 1.

5. The polynucleotide of claim 3 which is a cDNA.

6. An isolated and purified single-stranded polynucleotide consisting of at least 8 contiguous nucleotides of the nucleotide sequence shown in SEQ ID NO: 1 or its complement.

7. An expression construct, comprising;
the polynucleotide comprising at least one strand which consists of a coding sequence for the amino acid sequence shown in SEQ ID NO:2; and
a promoter which is located upstream from the coding sequence and which controls expression of the coding sequence.

8. The expression construct of claim 7 wherein the coding sequence consists of the nucleotide sequence shown in SEQ ID NO: 1.

9. A host cell comprising an expression construct, wherein the expression construct comprises:
a polynucleotide comprising at least one strand which consists of a coding sequence for the amino acid sequence shown in SEQ ID NO:2; and
a promoter which is located upstream from the coding sequence and which controls expression of the coding sequence.

10. The host cell of claim 9 which is prokaryotic.

11. The host cell of claim 9 which is eukaryotic.

12. A method of producing a protein, comprising the steps of:
culturing a host cell in a culture medium, wherein the host cell comprises an expression construct comprising (a) a polynucleotide comprising at least one strand which consists of a coding sequence for the amino acid sequence shown in SEQ ID NO:2 and (b) a promoter which is located upstream from the coding sequence and which controls expression of the coding sequence, wherein the step of culturing is carried out under conditions whereby the protein is expressed; and
recovering the protein.

13. A composition comprising:
a protein consisting of the amino acid sequence shown in SEQ ID NO:2; and
a pharmaceutically acceptable carrier.

14. A composition comprising:
a polynucleotide comprising at least one strand which consists of a coding sequence for the amino acid sequence shown in SEQ ID NO:2; and
a pharmaceutically acceptable carrier.

15. The composition of claim 14 wherein the polynucleotide consists of the nucleotide sequence shown in SEQ ID NO: 1.

16. The isolated and purified protein of claim 2 which is at least 96% identical.

17. The isolated and purified protein of claim 2 which is at least 98% identical.

18. The isolated and purified protein of claim 2 which is at least 99% identical.

* * * * *

SEQUENCE LISTING

<160> NUMBER OF SEQ ID NOS: 12

<210> SEQ ID NO 1
<211> LENGTH: 858
<212> TYPE: DNA
<213> ORGANISM: Homo sapiens

<400> SEQUENCE: 1

```
atgaccgact tcccggccag gctcttcctg gagaacagca agctggagca cagcgaggac      60
gagggcagcg tcctgggcca gggcggcagt ggcaccgtca tctaccgggc ccggtaccag     120
ggccagcctg tggccgtcaa gcgcttccac atcaaaaaat tcaagaactt tgctaacgta     180
ccggcagaca ccatgctgag gcacctgcgg gccaccgatg ccatgaagaa cttctccgag     240
ttccggcagg aggccagcat gctgcacgcg ctgcagcacc cctgcatcgt ggcgctcatc     300
ggcatcagca tccacccgct gctcttcgcc ctggagctcg cgccgctcag cagcctcaac     360
accgtgctgt ccgagaacgc cagagattct tcctttatac ccctgggaca catgctcacc     420
caaaaaatag cctaccagat cgcctcgggc ctggcctacc tgcacaagaa aaacatcatc     480
ttctgtgacc tgaagtcgga caacattctg gtgtggtccc ttgacgtcaa ggagcacatc     540
aacatcaagc tatctgacta cgggatttcg aggcagtcat ccatgaggg cgccctaggc      600
gtggagggca ctcctggcta ccaggcccca gagatcaggc ctcgcattgt atatgatgag     660
aaggtagata tgttctccta tggaatggtg ctctacgagt tgctgtcagg acagcgccct     720
gcactgggcc accaccagct ccagattgcc aagaagctgt ccaagggcat ccgcccggtt     780
ctggggcagc cggaggaagt gcagttccgg cgactgcagg cgctcatgat ggagtgctgg     840
gacactaagc cagagaag                                                    858
```

<210> SEQ ID NO 2
<211> LENGTH: 286
<212> TYPE: PRT
<213> ORGANISM: Homo sapiens

<400> SEQUENCE: 2

```
Met Thr Asp Phe Pro Ala Arg Leu Phe Leu Glu Asn Ser Lys Leu Glu
1               5                   10                  15

His Ser Glu Asp Glu Gly Ser Val Leu Gly Gln Gly Gly Ser Gly Thr
            20                  25                  30

Val Ile Tyr Arg Ala Arg Tyr Gln Gly Gln Pro Val Ala Val Lys Arg
        35                  40                  45

Phe His Ile Lys Lys Phe Lys Asn Phe Ala Asn Val Pro Ala Asp Thr
    50                  55                  60

Met Leu Arg His Leu Arg Ala Thr Asp Ala Met Lys Asn Phe Ser Glu
65                  70                  75                  80

Phe Arg Gln Glu Ala Ser Met Leu His Ala Leu Gln His Pro Cys Ile
                85                  90                  95

Val Ala Leu Ile Gly Ile Ser Ile His Pro Leu Cys Phe Ala Leu Glu
            100                 105                 110

Leu Ala Pro Leu Ser Ser Leu Asn Thr Val Leu Ser Glu Asn Ala Arg
        115                 120                 125

Asp Ser Ser Phe Ile Pro Leu Gly His Met Leu Thr Gln Lys Ile Ala
    130                 135                 140

Tyr Gln Ile Ala Ser Gly Leu Ala Tyr Leu His Lys Lys Asn Ile Ile
145                 150                 155                 160
```

```
Phe Cys Asp Leu Lys Ser Asp Asn Ile Leu Val Trp Ser Leu Asp Val
            165                 170                 175

Lys Glu His Ile Asn Ile Lys Leu Ser Asp Tyr Gly Ile Ser Arg Gln
            180                 185                 190

Ser Phe His Glu Gly Ala Leu Gly Val Glu Gly Thr Pro Gly Tyr Gln
            195                 200                 205

Ala Pro Glu Ile Arg Pro Arg Ile Val Tyr Asp Glu Lys Val Asp Met
    210                 215                 220

Phe Ser Tyr Gly Met Val Leu Tyr Glu Leu Leu Ser Gly Gln Arg Pro
225                 230                 235                 240

Ala Leu Gly His His Gln Leu Gln Ile Ala Lys Lys Leu Ser Lys Gly
            245                 250                 255

Ile Arg Pro Val Leu Gly Gln Pro Glu Val Gln Phe Arg Arg Leu
            260                 265                 270

Gln Ala Leu Met Met Glu Cys Trp Asp Thr Lys Pro Glu Lys
    275                 280                 285

<210> SEQ ID NO 3
<211> LENGTH: 394
<212> TYPE: PRT
<213> ORGANISM: Homo sapiens

<400> SEQUENCE: 3

Ala Glu Leu Thr Leu Glu Glu Ile Ile Gly Ile Gly Gly Phe Gly Lys
1               5                   10                  15

Val Tyr Arg Ala Phe Trp Ile Gly Asp Glu Val Ala Val Lys Ala Ala
            20                  25                  30

Arg His Asp Pro Asp Glu Asp Ile Ser Gln Thr Ile Glu Asn Val Arg
        35                  40                  45

Gln Glu Ala Lys Leu Phe Ala Met Leu Lys His Pro Asn Ile Ile Ala
    50                  55                  60

Leu Arg Gly Val Cys Leu Lys Glu Pro Asn Leu Cys Leu Val Met Glu
65                  70                  75                  80

Phe Ala Arg Gly Gly Pro Leu Asn Arg Val Leu Ser Gly Lys Arg Ile
                85                  90                  95

Pro Pro Asp Ile Leu Val Asn Trp Ala Val Gln Ile Ala Arg Gly Met
            100                 105                 110

Asn Tyr Leu His Asp Glu Ala Ile Val Pro Ile Ile His Arg Asp Leu
        115                 120                 125

Lys Ser Ser Asn Ile Leu Ile Leu Gln Lys Val Glu Asn Gly Asp Leu
    130                 135                 140

Ser Asn Lys Ile Leu Lys Ile Thr Asp Phe Gly Leu Ala Arg Glu Trp
145                 150                 155                 160

His Arg Thr Thr Lys Met Ser Ala Ala Gly Thr Tyr Ala Trp Met Ala
                165                 170                 175

Pro Glu Val Ile Arg Ala Ser Met Phe Ser Lys Gly Ser Asp Val Trp
            180                 185                 190

Ser Tyr Gly Val Leu Leu Trp Glu Leu Leu Thr Gly Glu Val Pro Phe
        195                 200                 205

Arg Gly Ile Asp Gly Leu Arg Val Ala Tyr Gly Val Ala Met Asn Lys
    210                 215                 220

Leu Ala Leu Pro Ile Pro Ser Thr Cys Pro Glu Pro Phe Ala Lys Leu
225                 230                 235                 240

Met Glu Asp Cys Trp Asn Pro Asp Pro His Ser Arg Pro Ser Phe Thr
```

```
                    245                 250                 255
Asn Ile Leu Asp Gln Leu Thr Thr Ile Glu Glu Ser Gly Phe Glu
            260                 265                 270

Met Pro Lys Asp Ser Phe His Cys Leu Gln Asp Asn Trp Lys His Glu
        275                 280                 285

Ile Gln Glu Met Phe Asp Gln Leu Arg Ala Lys Glu Lys Glu Leu Arg
        290                 295                 300

Thr Trp Glu Glu Leu Thr Arg Ala Ala Leu Gln Gln Lys Asn Gln
305                 310                 315                 320

Glu Glu Leu Leu Arg Arg Arg Glu Gln Glu Leu Ala Glu Arg Glu Ile
                325                 330                 335

Asp Ile Leu Glu Arg Glu Leu Asn Ile Ile Ile His Gln Leu Cys Gln
            340                 345                 350

Glu Lys Pro Arg Val Lys Lys Arg Lys Gly Lys Phe Arg Lys Ser Arg
        355                 360                 365

Leu Ala Gln Pro Val Leu Pro Phe Pro His Gly His Ser Arg Cys Pro
    370                 375                 380

Gly Gly Thr Gly Ser Ser Trp Gly Gly Gln
385                 390

<210> SEQ ID NO 4
<211> LENGTH: 473
<212> TYPE: DNA
<213> ORGANISM: Homo sapiens

<400> SEQUENCE: 4
cacgaggctg gtccctgaac tgttcatgac cgacttcccg gccaggctct tcctggagaa    60
cagcaagctg gagcacagcg aggacgaggg cagcgtcctg ggccagggcg gcagtggcac   120
cgtcatctac cgggcccggt accagggcca gcctgtggcc gtcaagcgct ccacatcaa    180 aaaattcaag aactttgcta acgtaccggc agacaccatg ctgaggcacc tgcgggccac   240
cgatgccatg aagaacttct ccgagttccg gcaggaggcc agcatgctgc acgcgctgca   300
gcacccctgc atcgtggcgc tcatcggcat cagcatccac ccgctctgct tcgccctgga   360
gctcgcgccg ctcagcagcc tcaacaccgt gctgtccgag aacgccagag attcttcctt   420
tatacccctg ggacacatgc tcacccaaaa aatagcctac cagatcgcct cgg          473

<210> SEQ ID NO 5
<211> LENGTH: 454
<212> TYPE: DNA
<213> ORGANISM: Homo sapiens

<400> SEQUENCE: 5
cacgaggctg gtccctgaac tgttcatgac cgacttcccg gccaggctct tcctggagaa    60
cagcaagctg gagcacagcg aggacgaggg cagcgtcctg ggccagggcg gcagtggcac   120
cgtcatctac cgggcccggt accagggcca gcctgtggcc gtcaagcgct ccacatcaa    180 aaaattcaag aactttgcta acgtaccggc agacaccatg ctgaggcacc tgcgggccac   240
cgatgccatg aagaacttct ccgagttccg gcaggaggcc agcatgctgc acgcgctgca   300
gcacccctgc atcgtggcgc tcatcggcat cagcatccac ccgctctgct tcgccctgga   360
gctcgcgccg ctcagcagcc tcaacaccgt gctgtccgag aacgccagag attcttcctt   420
tatacccctg ggacacatgc tcacccaaaa aata                                454

<210> SEQ ID NO 6
```

```
<211> LENGTH: 1066
<212> TYPE: DNA
<213> ORGANISM: Homo sapiens

<400> SEQUENCE: 6
ctcttcctgt gagaacagca agctggagca cagcgaggac gagggcagcg tcctgggcca      60
cggcggcagt ggcaccgtca tctaccgggc ccggtaccag ggccagcctg tggccgtcaa     120
gcgcttccac atcaaaaaat tcaagaactt tgctaacgta ccggcagaca ccatgctgag     180
gcacctgcgg gccaccgatg ccatgaagaa cttctccgag ttccggcagg aggccagcat     240
gctgcacgcg ctgcagcacc cctgcatcgt ggcgctcatc ggcatcagca tccacccgac     300
tctgcttcgc cctggagctc gcgccgctca gcagcctcaa caccgtgctg tccgagaacg     360
ccagagattc ttcctttata cccctgggac acatgctcac ccaaaaaata gcctaccaga     420
tcgcctcggg cctggcctac ctgcacaaga aaaacatcat cttctgtgac ctgaagtcgg     480
acaacattct ggtgtggtcc cttgacgtca aggagcacat caacatcaag ctatctgact     540
acgggatttc gaggcagtca ttccatgagg gcgccctagg cgtggagggc actcctggct     600
accaggcccc agagatcagg cctcgcattg tatatgatga aaggtagca tatgtctcct      660 atggaatggt gctctacgag ttgctgtcag acaggggcc tgcattgggc caccaacagc      720
ttccgattgc caagaggtgt ccaaggcatc cgcccggtac tgaggacagc cggaaggaac     780
tgcaatccgg cgatgcatgg ctcattattg agatgctggg aaactataat caagcgaacg     840
gagcactgtg gccctatacg taggtagccc caattagacg accctcacat tatgaaccaa     900
tcggtaataa acgtgtacgt gcgggactag cagccaccta taacacacag ccacggccac     960
ctgggctgtg atgcatacaa gacgctcaaa cacgcgggtc acagaaagcc tcatcgagtc    1020
gcatccaccc gagagagtag cgccgccgaa ctagtataga cggtat                   1066

<210> SEQ ID NO 7
<211> LENGTH: 471
<212> TYPE: DNA
<213> ORGANISM: Homo sapiens
<220> FEATURE:
<221> NAME/KEY: misc_feature
<222> LOCATION: (452)..(452)
<223> OTHER INFORMATION: n=a, c, g or t

<400> SEQUENCE: 7
cacgaggaaa aaattcaaga actttgctaa cgtaccggca gacaccatgc tgaggcacct      60
gcgggccacc gatgccatga agaacttctc cgagttccgg caggaggcca gcatgctgca    120
cgcgctgcag caccctgca tcgtggcgct catcggcatc agcatccacc cgctctgctt     180
cgccctggag ctcgcgccgc tcagcagcct caacaccgtg ctgtccgaga acgcagaga    240 ttcttccttt ataccctgg gacacatgct cacccaaaaa atagcctacc agatcgcctc     300
gggcctggcc tacctgcaca agaaaaacat catcttctgt gacctgaagt cggacaacat    360
tctggtgtgg tcccttgacg tcaaggagca catcaacatc aagctatctg actacgggat    420
ttcgaggcag tcattccatg agggcgccct angcgtggag ggcactcctg g             471

<210> SEQ ID NO 8
<211> LENGTH: 5475
<212> TYPE: DNA
<213> ORGANISM: Homo sapiens

<400> SEQUENCE: 8 cccttaatg attttgcaca ggccccaaag caatgctgtc ttacctgcgt gctcagctgc       60
```

```
ggaaagcgga aaagtgcaag ctgatgaaga tgatcatcgt gggtcccccg cgccagggca      120
agtccaccct cctggagatc ttacagacgg ggagggcccc caggtggtg catggagagg       180
ccaccatcag gaccaccaag tgggagctcc agaggccggc tggctcaaga gccaaggttg      240
agtccgtgga gttcaacgtc tgggacatcg ggggaccggc cagcatggcc actgtcaacc     300
agtgcttctt cacggacaag gccctgtacg tggtggtctg gaacctggcg ctgggggagg      360
aggccgtggc caacctccag ttctggctgc tcaacatcga ggccaaggcc caaacgccg       420
tggtgctggg ggtcgggacg cacctggatt taattgaagc caagttccgt gtggaaagga      480
ttgcaacgct gcgtgcctat gtgctggcac tctgccgctc ccctccggc tccagggcca      540
caggcttccc agacatcacc ttcaaacact tacatgagat ttcctgcaag agcctggaag     600
gtcaggaagg gctgcgacag ctgattttcc acgtcacgtg cagcatgaag gacgtgggca     660
gcaccatcgg ctgccagcga ctggcagggc ggctgatccc caggagctac ctgagcctgc     720
aggaggccgt gctggcagag cagcagcgcc gcagccggga cgacgacgtg cagtacctga     780
cggacaggca gctggagcag ctggtggagc agacgcccga caacgacatc aaggactacg      840
aggacctgca gtcagccatc agcttcctca tagaaaccgg caccctgctc catttcccgg     900
acaccagcca cggcctgagg aacctctact tcctcgaccc tatttggctc tccgaatgtc     960
tgcagaggat ctttaatatt aagggctctc ggtcagtggc caagaatggg gtgatcagag      1020
cagaagacct caggatgctg ctggtgggga ctggcttcac gcagcagacg gaagagcagt     1080
acttccagtt cctggccaag tttgagatcg ccctgcccgt cgccaatgac agctacctcc     1140
tgccccatct ccttccatct aaacctggcc tggacaccca cggtatgcgg cacccccacag   1200
ccaacaccat tcagagggta tttaagatga gcttcgttcc cgttggcttc tggcaaaggt     1260
ttatagcacg gatgctgatc agcctggcgg agatggacct gcagcttttt gaaaacaaga     1320
agaatactaa aagcaggaac aggaaagtca ccatttacag ttttacagga aaccagagaa     1380
atcgctgtag cacattcaga gtgaaaagaa atcagaccat ctattggcag gaagggctcc     1440
tggtcacttt tgatggggc tacctcagtg tggaatcttc cgacgtgaac tggaaaaaga     1500
agaaaagcgg aggaatgaaa attgtttgcc aatcagaagt gagggacttc tcagccatgg     1560
ctttcatcac ggaccacgtc aattccttga ttgatcagtg gttccccgcc ctgacgcca      1620
cagagagcga cgggacgcca ctcatggagc agtacgtgcc ctgcccggtc tgcgagacag     1680
cctgggccca gcacacggac cccagtgaga atcagaggg tgtgcagtac ttcgacatgg      1740
aagactgtgt cctgacggcc atcgagcggg acttcatctc ctgccccaga caccggacc      1800
tccccgtgcc gctgcaggag ctggtccctg aactgttcat gaccgacttc ccggccaggc     1860
tcttcctgga gaacagcaag ctggagcaca gcgaggacga gggcagcgtc ctgggccagg     1920
gcggcagtgg caccgtcatc taccgggccc ggtaccaggg ccagcctgtg ccgtcaagc      1980
gcttccacat caaaaaattc aagaactttg ctaacgtacc ggcagacacc atgctgaggc     2040
acctgcgggc caccgatgcc atgaagaact tctccgagtt ccggcaggag gccagcatgc     2100
tgcacgcgct gcagcacccc tgcatcgtgg cgctcatcgg catcagcatc cacccgctct     2160
gcttcgccct ggagctcgcg ccgctcagca gcctcaacac cgtgctgtcc gagaacgcca     2220
gagattcttc ctttataccc ctgggacaca tgctcaccca aaaaatagcc taccagatcg     2280
cctcgggcct ggcctacctg cacaagaaaa acatcatctt ctgtgacctg aagtcggaca     2340
acattctggt gtggtccctt gacgtcaagg agcacatcaa catcaagcta tctgactacg     2400
```

-continued

```
ggatttcgag gcagtcattc catgagggcg ccctaggcgt ggagggcact cctggctacc    2460
aggccccaga gatcaggcct cgcattgtat atgatgagaa ggtagatatg ttctcctatg    2520
gaatggtgct ctacgagttg ctgtcaggac agcgccctgc actgggccac caccagctcc    2580
agattgccaa gaagctgtcc aagggcatcc gcccggttct ggggcagccg gaggaagtgc    2640
agttccggcg actgcaggcg ctcatgatgg agtgctggga cactaagcca gagaagcgac    2700
cgctggccct gtcggtggtg agccagatga aggacccgac ttttgccacc ttcatgtatg    2760
aactgtgctg tgggaagcag acagccttct tctcatccca gggccaggag tacaccgtgg    2820
tgttttggga tggaaaagag gagtccagga actacacggt ggtgaacaca gagaagggcc    2880
tcatggaggt gcagaggatg tgctgccctg ggatgaaggt gagctgccag ctccaggtcc    2940
agagatccct gtggacagcc accgaggacc agaaaatcta catctacacc ctcaagggca    3000
tgtgcccctt aaacacaccc caacaggcct tggatactcc agctgtcgtc acctgcttct    3060
tggccgtgcc tgttattaaa aagaattcct acctggtctt agcgggcctc gccgatgggc    3120
ttgtggctgt gtttcccgtg gtgcggggca ccccaaagga cagctgctcc tacctgtgct    3180
cacacacagc caacaggtcc aagttcagca tcgcggatga agacgcacgg cagaacccct    3240
acccagtgaa ggccatggag gtggtcaaca gcggtctgga ggtctggtac agcaatgggc    3300
cgggcctcct tgtcatcgac tgtgcctccc tggagatctg caggcggctg gagccctaca    3360
tggcccccctc catggttacg tcagtcgtgt gcagctctga gggcagaggg gaggaggtcg    3420
tctggtgcct ggatgacaag gccaactcct tggtgatgta ccactccacc acctaccagc    3480
tgtgtgcccg gtacttctgc ggggtcccca gccccctcag ggacatgttt cccgtgcggc    3540
ccttggacac ggaaccccccg gcagccagcc acacggccaa cccaaaggtg cctgagggggg    3600
actccatcgc ggacgtgagc atcatgtaca gtgaggagct gggcacgcag atcctgatcc    3660
accaggaatc actcactgac tactgctcca tgtcctccta ctcctcatcc ccaccccgcc    3720
aggctgccag gtccccctca agcctcccca gctccccagc aagttcttcc agtgtgcctt    3780
tctccaccga ctgcgaggac tcagacatgc tacatacgcc cggtgctgcc tccgacaggt    3840
ctgagcatga cctgaccccc atggacgggg agaccttcag ccagcacctg caggccgtga    3900
agatcctcgc cgtcagagac ctcatttggg tccccaggcg cggtggagat gttatcgtca    3960
ttggcctgga gaaggattct gaagcccagc ggggccgagt cattgccgtc ttaaaagccc    4020
gagagctgac tccgcatggg gtgctggtgg atgctgccgt ggtggcaaag gacactgttg    4080
tgtgcacctt tgaaaatgaa aacacagagt ggtgcctggc cgtctggagg ggctggggcg    4140
ccagggagtt cgacattttc taccagtcct acgaggagct gggccggctg gaggcttgca    4200
ctcgcaagag aaggtaattc ctgtggaatg actgtcacac atcagagctg gctggcccgg    4260
ggctgcagcc tgacccctct gccatcggcc tctagttctc caaggaccta agacagat     4320
ggagttctcc cctgaactcc ttgctgctaa gaagtgctga gaagttactc gcctggcggt    4380
ggctccaggg ttctctggtt ctctggagca gagttctctg aatacccccat ccccaactg    4440
ctgattttac agccccaggg aagacagtgg tatcaggctg ggagcggcct cctctggcct    4500
cccccatcag tttgcaggag cagggtgca ggatcctgtt ctgagctggg tcaaacaaag    4560
cagggccggg ccttcctgcc atccccaggt ctcagatgga attacactag aggccctccg    4620
ctgggaagca cttgaggtag ggcaggaggg gggctgtgac ccctgccctt tccccgccag    4680
agacctcggg ctctcagcac attccacagg ctcctgagtc cccgaggcct gggccagctt    4740
gggcaagcca agatcagatg tctctgtgtt cgggaaggtc tccgtgtggg aaagcccttg    4800
```

-continued

```
ggggatcccg ggtgaggagt gttgccccat ccagagaatg aatgagttcc tttaagtgcc    4860
accgccagca agcccagagg cacacagtcc gagtgcaccc gcttagcctt tacattcctc    4920
tccaccgaca aaaggaaggg gaaactcaat cagcaggact tcagaaaggg ccttgtgttt    4980
atagctttgt caagtaaatt tggacgcagc tggagcacag gccctgtttg tttgcacata    5040
ataatcttgt ttatcacttt aaaaaattca gtaatatctc agcagtcagg cttctggttg    5100
tgaaatcaca ttgtatggga tttataccaa attatgtatt tgctaaacat tcactgcaca    5160
cgtgtacagc ggagtacgaa aaggaacgtt gtccacaggg gatttatgga tacaacagca    5220
aacattttat aaactatgca catgcattac acacatgcac acacatatgc acacacatgt    5280
gcaaacatag ccacttttt gtcaagagtt acccttgggg gctccttaaa ccagaatggg     5340
agtttgaaag agagatcata ctccagctga gtttgttga ccctttcta aaattaaaaa      5400 gatcaaattt agtatttgct ggatatgcag ggagatgaga ctctttaat ctcaaaataa     5460 acagattctt tcaag                                                     5475
```

<210> SEQ ID NO 9
<211> LENGTH: 1394
<212> TYPE: PRT
<213> ORGANISM: Homo sapiens

<400> SEQUENCE: 9

```
Met Leu Ser Tyr Leu Arg Ala Gln Leu Arg Lys Ala Glu Lys Cys Lys
1               5                   10                  15

Leu Met Lys Met Ile Ile Val Gly Pro Pro Arg Gln Gly Lys Ser Thr
                20                  25                  30

Leu Leu Glu Ile Leu Gln Thr Gly Arg Ala Pro Gln Val Val His Gly
            35                  40                  45

Glu Ala Thr Ile Arg Thr Thr Lys Trp Glu Leu Gln Arg Pro Ala Gly
        50                  55                  60

Ser Arg Ala Lys Val Glu Ser Val Glu Phe Asn Val Trp Asp Ile Gly
65                  70                  75                  80

Gly Pro Ala Ser Met Ala Thr Val Asn Gln Cys Phe Phe Thr Asp Lys
                85                  90                  95

Ala Leu Tyr Val Val Val Trp Asn Leu Ala Leu Gly Glu Glu Ala Val
                100                 105                 110

Ala Asn Leu Gln Phe Trp Leu Leu Asn Ile Glu Ala Lys Ala Pro Asn
            115                 120                 125

Ala Val Val Leu Val Val Gly Thr His Leu Asp Leu Ile Glu Ala Lys
        130                 135                 140

Phe Arg Val Glu Arg Ile Ala Thr Leu Arg Ala Tyr Val Leu Ala Leu
145                 150                 155                 160

Cys Arg Ser Pro Ser Gly Ser Arg Ala Thr Gly Phe Pro Asp Ile Thr
                165                 170                 175

Phe Lys His Leu His Glu Ile Ser Cys Lys Ser Leu Glu Gly Gln Glu
            180                 185                 190

Gly Leu Arg Gln Leu Ile Phe His Val Thr Cys Ser Met Lys Asp Val
        195                 200                 205

Gly Ser Thr Ile Gly Cys Gln Arg Leu Ala Gly Arg Leu Ile Pro Arg
    210                 215                 220

Ser Tyr Leu Ser Leu Gln Glu Ala Val Leu Ala Glu Gln Gln Arg Arg
225                 230                 235                 240

Ser Arg Asp Asp Asp Val Gln Tyr Leu Thr Asp Arg Gln Leu Glu Gln
```

-continued

```
                245                 250                 255
Leu Val Glu Gln Thr Pro Asp Asn Asp Ile Lys Asp Tyr Glu Asp Leu
            260                 265                 270
Gln Ser Ala Ile Ser Phe Leu Ile Glu Thr Gly Thr Leu Leu His Phe
        275                 280                 285
Pro Asp Thr Ser His Gly Leu Arg Asn Leu Tyr Phe Leu Asp Pro Ile
    290                 295                 300
Trp Leu Ser Glu Cys Leu Gln Arg Ile Phe Asn Ile Lys Gly Ser Arg
305                 310                 315                 320
Ser Val Ala Lys Asn Gly Val Ile Arg Ala Glu Asp Leu Arg Met Leu
                325                 330                 335
Leu Val Gly Thr Gly Phe Thr Gln Gln Thr Glu Glu Gln Tyr Phe Gln
            340                 345                 350
Phe Leu Ala Lys Phe Glu Ile Ala Leu Pro Val Ala Asn Asp Ser Tyr
        355                 360                 365
Leu Leu Pro His Leu Leu Pro Ser Lys Pro Gly Leu Asp Thr His Gly
    370                 375                 380
Met Arg His Pro Thr Ala Asn Thr Ile Gln Arg Val Phe Lys Met Ser
385                 390                 395                 400
Phe Val Pro Val Gly Phe Trp Gln Arg Phe Ile Ala Arg Met Leu Ile
                405                 410                 415
Ser Leu Ala Glu Met Asp Leu Gln Leu Phe Glu Asn Lys Lys Asn Thr
            420                 425                 430
Lys Ser Arg Asn Arg Lys Val Thr Ile Tyr Ser Phe Thr Gly Asn Gln
        435                 440                 445
Arg Asn Arg Cys Ser Thr Phe Arg Val Lys Arg Asn Gln Thr Ile Tyr
    450                 455                 460
Trp Gln Glu Gly Leu Leu Val Thr Phe Asp Gly Gly Tyr Leu Ser Val
465                 470                 475                 480
Glu Ser Ser Asp Val Asn Trp Lys Lys Lys Ser Gly Gly Met Lys
                485                 490                 495
Ile Val Cys Gln Ser Glu Val Arg Asp Phe Ser Ala Met Ala Phe Ile
            500                 505                 510
Thr Asp His Val Asn Ser Leu Ile Asp Gln Trp Phe Pro Ala Leu Thr
        515                 520                 525
Ala Thr Glu Ser Asp Gly Thr Pro Leu Met Glu Gln Tyr Val Pro Cys
    530                 535                 540
Pro Val Cys Glu Thr Ala Trp Ala Gln His Thr Asp Pro Ser Glu Lys
545                 550                 555                 560
Ser Glu Asp Val Gln Tyr Phe Asp Met Glu Asp Cys Val Leu Thr Ala
                565                 570                 575
Ile Glu Arg Asp Phe Ile Ser Cys Pro Arg His Pro Asp Leu Pro Val
            580                 585                 590
Pro Leu Gln Glu Leu Val Pro Glu Leu Phe Met Thr Asp Phe Pro Ala
        595                 600                 605
Arg Leu Phe Leu Glu Asn Ser Lys Leu Glu His Ser Glu Asp Glu Gly
    610                 615                 620
Ser Val Leu Gly Gln Gly Gly Ser Gly Thr Val Ile Tyr Arg Ala Arg
625                 630                 635                 640
Tyr Gln Gly Gln Pro Val Ala Val Lys Arg Phe His Ile Lys Lys Phe
                645                 650                 655
Lys Asn Phe Ala Asn Val Pro Ala Asp Thr Met Leu Arg His Leu Arg
            660                 665                 670
```

```
Ala Thr Asp Ala Met Lys Asn Phe Ser Glu Phe Arg Gln Glu Ala Ser
            675                 680                 685

Met Leu His Ala Leu Gln His Pro Cys Ile Val Ala Leu Ile Gly Ile
        690                 695                 700

Ser Ile His Pro Leu Cys Phe Ala Leu Glu Leu Ala Pro Leu Ser Ser
705                 710                 715                 720

Leu Asn Thr Val Leu Ser Glu Asn Ala Arg Asp Ser Ser Phe Ile Pro
                725                 730                 735

Leu Gly His Met Leu Thr Gln Lys Ile Ala Tyr Gln Ile Ala Ser Gly
            740                 745                 750

Leu Ala Tyr Leu His Lys Lys Asn Ile Ile Phe Cys Asp Leu Lys Ser
        755                 760                 765

Asp Asn Ile Leu Val Trp Ser Leu Asp Val Lys Glu His Ile Asn Ile
770                 775                 780

Lys Leu Ser Asp Tyr Gly Ile Ser Arg Gln Ser Phe His Glu Gly Ala
785                 790                 795                 800

Leu Gly Val Glu Gly Thr Pro Gly Tyr Gln Ala Pro Glu Ile Arg Pro
            805                 810                 815

Arg Ile Val Tyr Asp Glu Lys Val Asp Met Phe Ser Tyr Gly Met Val
        820                 825                 830

Leu Tyr Glu Leu Leu Ser Gly Gln Arg Pro Ala Leu Gly His His Gln
        835                 840                 845

Leu Gln Ile Ala Lys Lys Leu Ser Lys Gly Ile Arg Pro Val Leu Gly
        850                 855                 860

Gln Pro Glu Glu Val Gln Phe Arg Arg Leu Gln Ala Leu Met Met Glu
865                 870                 875                 880

Cys Trp Asp Thr Lys Pro Glu Lys Arg Pro Leu Ala Leu Ser Val Val
                885                 890                 895

Ser Gln Met Lys Asp Pro Thr Phe Ala Thr Phe Met Tyr Glu Leu Cys
            900                 905                 910

Cys Gly Lys Gln Thr Ala Phe Phe Ser Ser Gln Gly Gln Glu Tyr Thr
        915                 920                 925

Val Val Phe Trp Asp Gly Lys Glu Glu Ser Arg Asn Tyr Thr Val Val
930                 935                 940

Asn Thr Glu Lys Gly Leu Met Glu Val Gln Arg Met Cys Cys Pro Gly
945                 950                 955                 960

Met Lys Val Ser Cys Gln Leu Gln Val Gln Arg Ser Leu Trp Thr Ala
            965                 970                 975

Thr Glu Asp Gln Lys Ile Tyr Ile Tyr Thr Leu Lys Gly Met Cys Pro
        980                 985                 990

Leu Asn Thr Pro Gln Gln Ala Leu  Asp Thr Pro Ala Val  Val Thr Cys
        995                 1000                1005

Phe Leu  Ala Val Pro Val Ile  Lys Lys Asn Ser Tyr  Leu Val Leu
    1010                1015                1020

Ala Gly  Leu Ala Asp Gly Leu  Val Ala Val Phe Pro  Val Val Arg
    1025                1030                1035

Gly Thr  Pro Lys Asp Ser Cys  Ser Tyr Leu Cys Ser  His Thr Ala
    1040                1045                1050

Asn Arg  Ser Lys Phe Ser Ile  Ala Asp Glu Asp Ala  Arg Gln Asn
    1055                1060                1065

Pro Tyr  Pro Val Lys Ala Met  Glu Val Val Asn Ser  Gly Ser Glu
    1070                1075                1080
```

```
Val Trp Tyr Ser Asn Gly Pro Gly Leu Leu Val Ile Asp Cys Ala
1085             1090            1095

Ser Leu Glu Ile Cys Arg Arg Leu Glu Pro Tyr Met Ala Pro Ser
1100             1105            1110

Met Val Thr Ser Val Val Cys Ser Ser Glu Gly Arg Gly Glu Glu
1115             1120            1125

Val Val Trp Cys Leu Asp Asp Lys Ala Asn Ser Leu Val Met Tyr
1130             1135            1140

His Ser Thr Thr Tyr Gln Leu Cys Ala Arg Tyr Phe Cys Gly Val
1145             1150            1155

Pro Ser Pro Leu Arg Asp Met Phe Pro Val Arg Pro Leu Asp Thr
1160             1165            1170

Glu Pro Pro Ala Ala Ser His Thr Ala Asn Pro Lys Val Pro Glu
1175             1180            1185

Gly Asp Ser Ile Ala Asp Val Ser Ile Met Tyr Ser Glu Glu Leu
1190             1195            1200

Gly Thr Gln Ile Leu Ile His Gln Glu Ser Leu Thr Asp Tyr Cys
1205             1210            1215

Ser Met Ser Ser Tyr Ser Ser Ser Pro Pro Arg Gln Ala Ala Arg
1220             1225            1230

Ser Pro Ser Ser Leu Pro Ser Ser Pro Ala Ser Ser Ser Ser Val
1235             1240            1245

Pro Phe Ser Thr Asp Cys Glu Asp Ser Asp Met Leu His Thr Pro
1250             1255            1260

Gly Ala Ala Ser Asp Arg Ser Glu His Asp Leu Thr Pro Met Asp
1265             1270            1275

Gly Glu Thr Phe Ser Gln His Leu Gln Ala Val Lys Ile Leu Ala
1280             1285            1290

Val Arg Asp Leu Ile Trp Val Pro Arg Arg Gly Gly Asp Val Ile
1295             1300            1305

Val Ile Gly Leu Glu Lys Asp Ser Glu Ala Gln Arg Gly Arg Val
1310             1315            1320

Ile Ala Val Leu Lys Ala Arg Glu Leu Thr Pro His Gly Val Leu
1325             1330            1335

Val Asp Ala Ala Val Val Ala Lys Asp Thr Val Val Cys Thr Phe
1340             1345            1350

Glu Asn Glu Asn Thr Glu Trp Cys Leu Ala Val Trp Arg Gly Trp
1355             1360            1365

Gly Ala Arg Glu Phe Asp Ile Phe Tyr Gln Ser Tyr Glu Glu Leu
1370             1375            1380

Gly Arg Leu Glu Ala Cys Thr Arg Lys Arg Arg
1385             1390
```

<210> SEQ ID NO 10
<211> LENGTH: 4216
<212> TYPE: DNA
<213> ORGANISM: Homo sapiens

<400> SEQUENCE: 10

```
caaagcaatg ctgtcttacc tgcgtgctca gctgcggaaa gcggaaaagt gcaagctgat      60
gaagatgatc atcgtgggtc ccccgcgcca gggcaagtcc accctcctgg agatcttaca    120
gacggggagg gcccccccagg tggtgcatgg agaggccacc atcaggacca ccaagtggga    180
gctccagagg ccggctggct caagagccaa ggttgagtcc gtggagttca acgtctggga    240
```

-continued

```
catcggggga ccggccagca tggccactgt caaccagtgc ttcttcacgg acaaggccct    300
gtacgtggtg gtctggaacc tggcgctggg ggaggaggcc gtggccaacc tccagttctg    360
gctgctcaac atcgaggcca aggccccaaa cgccgtggtg ctggtggtcg ggacgcacct    420
ggatttaatt gaagccaagt tccgtgtgga aaggattgca acgctgcgtg cctatgtgct    480
ggcactctgc cgctcccct ccggctccag ggccacaggc ttcccagaca tcaccttcaa    540
acacttacat gagatttcct gcaagagcct ggaaggtcag gaagggctgc gacagctgat    600
tttccacgtc acgtgcagca tgaaggacgt gggcagcacc atcggctgcc agcgactggc    660
agggcggctg atccccagga gctacctgag cctgcaggag gccgtgctgg cagagcagca    720
gcgccgcagc cgggacgacg acgtgcagta cctgacggac aggcagctgg agcagctggt    780
ggagcagacg cccgacaacg acatcaagga ctacgaggcc ctgcagtcag ccatcagctt    840
cctcatagaa accggcaccc tgctccattt cccggacacc agccacggcc tgaggaacct    900
ctacttcctc gaccctattt ggctctccga atgtctgcag aggatcttta atattaaggg    960
ctctcggtca gtggccaaga tggggtgat cagagcagaa gacctcagga tgctgctggt    1020
ggggactggc ttcacgcagc agacggaaga gcagtacttc cagttcctgg ccaagtttga    1080
gatcgccctg cccgtcgcca tgacagcta cctcctgccc catctccttc catctaaacc    1140
tggcctggac acccacggta tgcggcaccc cacagccaac accattcaga gggtatttaa    1200
gatgagcttc gttccgttg gcttctggca aaggtttata gcacggatgc tgatcagcct    1260
ggcggagatg gacctgcagc tttttgaaaa caagaagaat actaaaagca ggaacaggaa    1320
agtcaccatt tacagtttta caggaaaacca gagaaatcgc tgtagcacat tcagagtgaa    1380
aagaaatcag accatctatt ggcaggaagg gctcctggtc acttttgatg ggggctacct    1440
cagtgtggaa tcttccgacg tgaactggaa aaagaagaaa agcggaggaa tgaaaattgt    1500
ttgccaatca gaagtgaggg acttctcagc catggctttc atcacggacc acgtcaattc    1560
cttgattgat cagtggtttc cgccctgac agccacagag agcgacggga cgccactcat    1620
ggagcagtac gtgccctgcc cggtctgcga cacagcctgg gcccagcaca cggaccccag    1680
tgagaaatca gaggatgtgc agtacttcga catggaagac tgtgtcctga cggccatcga    1740
gcggacttc atctcctgcc ccagacaccc ggacctcccc gtgccgctgc aggagctggt    1800
ccctgaactg ttcatgaccg acttcccggc caggctcttc ctggagaaca gcaagctgga    1860
gcacagcgag gacgagggca gcgtcctggg ccagggcggc agtggcaccg tcatctaccg    1920
ggcccggtac cagggccagc ctgtggccgt caagcgcttc cacatcaaaa aattcaagaa    1980
ctttgctaac gtaccggcag acaccatgct gaggcacctg cgggccaccg atgccatgaa    2040
gaacttctcc gagttccggc aggaggccag catgctgcac gcgctgcagc cccctgcat    2100
cgtggcgctc atcggcatca gcatccaccc gctctgcttc gccctggagc tcgcgccgct    2160
cagcagcctc aacaccgtgc tgtccgagaa cgccagagat tcttcctta tacccctggg    2220
acacatgctc acccaaaaaa tagcctacca gatcgcctcg ggcctggcct acctgcacaa    2280
gaaaaacatc atcttctgtg acctgaagtc ggacaacatt ctggtgtggt cccttgacgt    2340
caaggagcac atcaacatca gctatctga ctacgggatt tcgaggcagt cattccatga    2400
gggcgcccta ggcgtggagg gcactcctgg ctaccaggcc ccagagatca ggcctcgcat    2460
tgtatatgat gagaaggtag atatgttctc ctatggaatg gtgctctacg agttgctgtc    2520
aggacagcgc cctgcactgg gccaccacca gctccagatt gccaagaagc tgtccaaggg    2580
catccgcccg gttctggggc agccggagga agtgcagttc cggcgactgc aggcgctcat    2640
```

```
gatggagtgc tgggacacta agccagagaa gcgaccgctg ccctgtcgg tggtgagcca      2700 gatgaaggac ccgacttttg ccaccttcat gtatgaactg tgctgtggga agcagacagc      2760
cttcttctca tcccagggcc aggagtacac cgtggtgttt tgggatggaa aagaggagtc      2820
caggaactac acggtggtga acacagagaa gggcctcatg gaggtgcaga ggatgtgctg      2880
ccctgggatg aaggtgagct gccagctcca ggtccagaga tccctgtgga cagccaccga      2940
ggaccagaaa atctacatct acaccctcaa gggcatgtgc cccttaaaca caccccaaca      3000
ggccttggat actccagctg tcgtcacctg cttcttggcc gtgcctgtta ttaaaaagaa      3060
ttcctacctg gtcttagcgg gcctcgccga tgggcttgtg gctgtgtttc ccgtggtgcg      3120
gggcacccca aggacagct gctcctacct gtgctcacac acagccaaca ggtccaagtt      3180
cagcatcgcg gatgaagacg cacggcagaa cccctaccca gtgaaggcca tggaggtggt      3240
caacagcggc tctgaggtct ggtacagcaa tgggccgggc ctccttgtca tcgactgtgc      3300
ctccctggag atctgcaggc ggctggagcc ctacatggcc ccctccatgg ttacgtcagt      3360
cgtgtgcagc tctgagggca gagggggagga ggtcgtctgg tgcctggatg acaaggccaa      3420
ctccttggtg atgtaccact ccaccaccta ccagctgtgt gcccggtact tctgcggggt      3480
ccccagcccc ctcagggaca tgttttcccgt gcggccttg gacacggaac cccccggcagc      3540 cagccacacg gccaacccaa aggtgcctga gggggactcc atcgcggacg tgagcatcat      3600
gtacagtgag gagctgggca cgcagatcct gatccaccag gaatcactca ctgactactg      3660
ctccatgtcc tcctactcct catccccacc ccgccaggct gccaggtccc cctcaagcct      3720
ccccagctcc ccagcaagtt cttccagtgt gcctttctcc accgactgcg aggactcaga      3780
catgctacat acgcccggtg ctgcctccga caggtctgag catgacctga cccccatgga      3840
cggggagacc ttcagccagc acctgcaggc cgtgaagatc ctcgccgtca gagacctcat      3900
ttgggtcccc aggcgcggtg gagatgttat cgtcattggc ctggagaagg attctgaagc      3960
ccagcggggc cgagtcattg ccgtcttaaa agcccgagag ctgactccgc atggggtgct      4020
ggtggatgct gccgtggtgg caaaggacac tgttgtgtgc acctttgaaa atgaaaacac      4080
agagtggtgc ctggccgtct ggaggggctg gggcgccagg gagttcgaca tttttctacca      4140 gtcctacgag gagctgggcc ggctggaggc ttgcactcgc aagagaaggt aattcctgtg      4200
gaatgactgt cacaca                                                    4216

<210> SEQ ID NO 11
<211> LENGTH: 22
<212> TYPE: DNA
<213> ORGANISM: Artificial
<220> FEATURE:
<221> NAME/KEY: misc_feature
<223> OTHER INFORMATION: forward primer

<400> SEQUENCE: 11
ctgtgacctg aagtcggaca ac                                                22

<210> SEQ ID NO 12
<211> LENGTH: 21
<212> TYPE: DNA
<213> ORGANISM: Homo sapiens
<220> FEATURE:
<221> NAME/KEY: misc_feature
```

```
<223> OTHER INFORMATION: reverse primer

<400> SEQUENCE: 12
ggaatgactg cctcgaaatc c                                                    21
```